United States Patent
Hilpert et al.

(10) Patent No.: US 10,112,938 B2
(45) Date of Patent: Oct. 30, 2018

(54) INDOLIN-2-ONE AND 1,3-DIHYDRO-PYRROLO[3,2-C]PYRIDIN-2-ONE DERIVATIVES

(71) Applicant: Hoffmann-La Roche Inc., Little Falls, NJ (US)

(72) Inventors: Hans Hilpert, Muenchenstein (CH); Sabine Kolczewski, Loerrach (DE); Anja Limberg, Basel (CH); Theodor Stoll, Binningen (CH)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/353,355

(22) Filed: Nov. 16, 2016

(65) Prior Publication Data
US 2017/0057960 A1    Mar. 2, 2017

Related U.S. Application Data

(63) Continuation of application No. PCT/EP2015/060937, filed on May 19, 2015.

(30) Foreign Application Priority Data

May 22, 2014   (EP) .................................... 14169477

(51) Int. Cl.
| | | |
|---|---|---|
| C07D 401/14 | (2006.01) | |
| C07D 471/04 | (2006.01) | |
| C07D 403/04 | (2006.01) | |
| C07D 403/14 | (2006.01) | |
| C07D 405/14 | (2006.01) | |
| C07D 411/12 | (2006.01) | |
| C07D 413/14 | (2006.01) | |
| C07D 417/14 | (2006.01) | |
| A61K 31/4178 | (2006.01) | |
| A61K 31/4439 | (2006.01) | |
| A61K 31/444 | (2006.01) | |
| A61K 31/506 | (2006.01) | |
| A61K 45/06 | (2006.01) | |

(52) U.S. Cl.
CPC ........ *C07D 471/04* (2013.01); *A61K 31/4178* (2013.01); *A61K 31/444* (2013.01); *A61K 31/4439* (2013.01); *A61K 31/506* (2013.01); *A61K 45/06* (2013.01); *C07D 401/14* (2013.01); *C07D 403/04* (2013.01); *C07D 403/14* (2013.01); *C07D 405/14* (2013.01); *C07D 411/12* (2013.01); *C07D 413/14* (2013.01); *C07D 417/14* (2013.01)

(58) Field of Classification Search
CPC .. C07D 471/04; C07D 401/14; C07D 403/04; C07D 403/14; C07D 405/14; C07D 411/12; C07D 413/14; C07D 417/14
See application file for complete search history.

(56) References Cited

U.S. PATENT DOCUMENTS 8,772,288 B2   7/2014   Eastwood et al.

FOREIGN PATENT DOCUMENTS

| EP | 2 108 641 A1 | 10/2009 |
|---|---|---|
| JP | 2011-516512 A | 5/2011 |
| TW | 201504223 A | 2/2015 |
| WO | 86/03749 A1 | 7/1986 |
| WO | 91/06545 A1 | 5/1991 |
| WO | 2013/000994 A1 | 1/2013 |
| WO | 2014/040969 A1 | 3/2014 |

OTHER PUBLICATIONS

ISR for PCT/EP2015/060937.

*Primary Examiner* — Sahar Javanmard
(74) *Attorney, Agent, or Firm* — Brian L. Buckwalter

(57) ABSTRACT

The present invention is concerned with indolin-2-one and 1,3-dihydro-pyrrolo[3,2-c]pyridin-2-one derivatives of general formula I wherein $Ar^1$, $A^2$, $R^1$, $R^2$, $R^3$, X and n are as described herein and pharmaceutically acceptable salts thereof for treatment of central nervous system disorders 13 Claims, 1 Drawing Sheet

INDOLIN-2-ONE AND 1,3-DIHYDRO-PYRROLO[3,2-C]PYRIDIN-2-ONE DERIVATIVES

CROSS REFERENCE TO RELATED APPLICATIONS

This application is a continuation of International Application No. PCT/EP2015/060937 having an international filing date of May 19, 2015 and which claims benefit under 35 U.S.C. § 119 to International Application EP 14169477.8 filed May 22, 2014. The entire contents of both are incorporated herein by reference.

FIELD OF THE INVENTION

The present invention relates to novel compounds of formula I, wherein $Ar^1$, $Ar^2$, $R^1$, $R^2$, $R^3$, X and n are as described herein, having pharmaceutical activity, their manufacture, pharmaceutical compositions containing them and their potential use as medicaments.

BACKGROUND OF THE INVENTION

Schizophrenia is a complex mental disorder typically appearing in late adolescence or early adulthood with a world-wide prevalence of approximately 1% of the adult population, which has enormous social and economic impact. The criteria of the Association of European Psychiatrists (ICD) and the American Psychiatric Association (DSM) for the diagnosis of schizophrenia require two or more characteristic symptoms to be present: delusions, hallucinations, disorganized speech, grossly disorganized or catatonic behavior (positive symptoms), or negative symptoms (alogia, affective flattening, lack of motivation, anhedonia). As a group, people with schizophrenia have functional impairments that may begin in childhood, continue throughout adult life and make most patients unable to maintain normal employment or otherwise have normal social function. They also have a shortened lifespan compared to the general population, and suffer from an increased prevalence of a wide variety of other neuropsychiatric syndromes, including substance abuse, obsessive-compulsive symptoms and abnormal involuntary movements prior to antipsychotic treatment. Schizophrenia is also associated with a wide range of cognitive impairments, bipolar disorders, major depression and anxiety disorders, the severity of which limits the functioning of patients, even when psychotic symptoms are well controlled. The primary treatment of schizophrenia is antipsychotic medications. Antipsychotics, for example risperidone, olanzapine, however, fail to significantly ameliorate the negative symptoms and cognitive dysfunction.

Antipsychotic drugs have shown clinical efficacy for the treatment of the following diseases:
Fibromyalgia, which is a syndrome characterized by chronic generalized pain associated with different somatic symptoms, such as sleep disturbances, fatigue, stiffness, balance problems, hypersensitivity to physical and psychological environmental stimuli, depression and anxiety (*CNS Drugs*, 2012 26(2):135-53).
Schizoaffective disorders: includes psychotic and affective symptoms, this disorder falls on a spectrum between bipolar disorders (with depressive and manic episodes, alcohol and drug addiction, substance abuse) and schizophrenia. (*J. Clin. Psychiatry*, 2010, 71, Suppl. 2, 14-9; *Pediatr. Drugs* 2011 13 (5), 291-302).
Major depression: *BMC Psychiatry* 2011 11; 86.
Treatment resistent depression: *Journal of Psychopharmacology* 2012 26(5)587.
Anxiety: *European Neuropsychopharmacology* 2011 21:429-449.
Bipolar disorders: *Encephale, International J. of Neuropsychopharmacology* 2011 14:1029-104, *International J. of Neuropsychopharmacology*, 2012 p. 1-12, 1 of Neuropsychopharmacology, 2011 0(0), 1-15.
Mood disorders: *J. Psychopharmacol* 2012, Jan. 11, *CNS Drugs* 2010 Feb. 24(2):131-61.
Autism: *Current opinion in pediatrics* 2011 23:621-627; *J. Clin. Psychiatry* 2011 72(9), 1270-1276.
Alzheimer's disease: *J. Clin. Psychiatry* 2012 73(1), 121-128.
Parkinson's disease: *Movement Disorders* 2011 Vol. 26, No. 6.
Chronic fatigue syndrome: *European Neuropsychopharmacology* 2011 21:282-286.
Borderline Personality disorder: *J. Clin. Psychiatry* 2011 72 (10), 1363-1365.
*J. Clin. Psychiatry* 2011 72(10):1353-1362.
Anti-inflammatory effects in arthritis: *European J. of Pharmacology* 2012 678:55-60.

BRIEF SUMMARY OF THE INVENTIONS

The present invention is concerned with indole-2-one and 1,4-dihydro-pyrrolo[3,2-c]pyridine-2-one derivatives of general formula

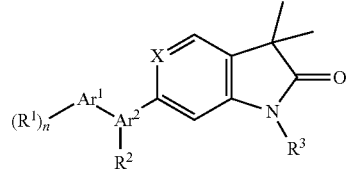

wherein
$Ar^1$ is phenyl, pyridinyl or pyrimidinyl;
$Ar^2$ is a 5 or 6 membered heteroaryl group, containing 2 or 3 heteroatoms, selected from N, O or S;
$R^1$ is hydrogen, $C_{1-7}$-alkyl, halogen or $C_{1-7}$-alkoxy;
$R^2$ is hydrogen or $C_{1-7}$-alkyl;
$R^3$ is hydrogen, $C_{1-7}$-alkyl, $C_{1-7}$-alkyl substituted by hydroxy, cycloalkyl, oxetan-3-yl, pyridinyl, imidazolyl, pyrazolyl, pyrimidinyl, which rings may optionally substituted by $C_{1-7}$-alkyl, or is —$(CH_2)_3$—$S(O)_2$-cyclopropyl;
X is CH or N;
n is 1 or 2;
or a pharmaceutically acceptable salt thereof, a racemic mixture, an enantiomer, an optical isomer, a stereoisomer thereof.
mixture, or with its corresponding enantiomer and/or optical isomer and/or stereoisomer thereof.

The present invention further relates to central nervous system disorders with compounds of formula I, compositions containing compounds of formula I and methods of the preparation of compounds of formula I.

DETAILED DESCRIPTION OF THE INVENTION

Figure 1:
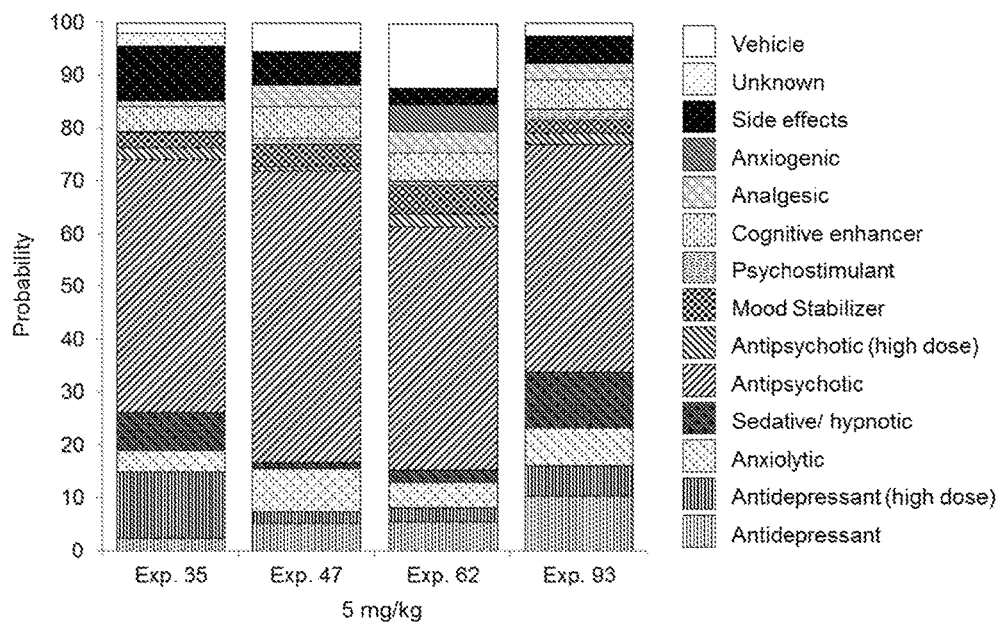
FIG. 1 depicts the SmartCube® signatures of compounds 13, 54, 58 and 71 (at 25 mg/kg) which are similar to those of atypical antipsychotics.

The present invention is concerned with indolin-2-one and 1,3-dihydro-pyrrolo[3,2-c]pyridin-2-one derivatives of general formula

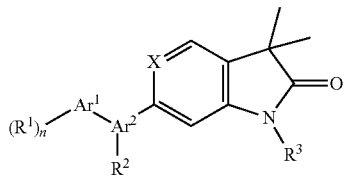

I wherein
$Ar^1$ is phenyl, pyridinyl or pyrimidinyl;
$Ar^2$ is a 5 or 6 membered heteroaryl group, containing 2 or 3 heteroatoms, selected from N, O or S;
$R^1$ is hydrogen, lower alkyl, halogen or lower alkoxy;
$R^2$ is hydrogen or lower alkyl;
$R^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —$(CH_2)_3$—$S(O)_2$-cyclopropyl;
X is CH or N;
n is 1 or 2;
as well as with a pharmaceutically acceptable salts thereof, with a racemic mixture, or with its corresponding enantiomer and/or optical isomer and/or stereoisomer thereof, for use in the treatment of certain central nervous system disorders which are positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems.

WO9106545 describes a very close structure containing a phenyl substituted imidazole moity for $Ar^2$ for prevention of clumping of both erythrocytes and thrombocytes. EP2108641 and WO2008046083 disclose a very broad scope of similar compounds which are inhibitors of the p38 nitrogen activated protein kinase for the treatment of inflammation diseases and benign prostatic pyperplasia, respectively.

Now it has been found that the compounds of formula I may be used for the treatment of CNS diseases. The described compounds have been shown to reverse the L-687,414 ((3R,4R)-3 amino-1-hydroxy-4-methyl-pyrrolidin-2-one, a NMDA glycine site antagonist) induced hyperlocomotion, a behavioral pharmacodynamic mouse model for schizophrenia, described by D. Alberati et al. in *Pharmacology, Biochemistry and Behavior*, 97 (2010), 185-191. The authors described that hyperlocomotion induced by L-687,414 was inhibited by a series of known antipsychotic drugs. The compounds of formula I demonstrate marked activity in this model. These findings predict antipsychotic activity for the present compounds, making them useful for the treatment of positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems. The results are shown in Table 1.

In addition to the reversal of L-687,414 induced hyperlocomotion experiment as described above, some compounds of the present invention have been tested in SmartCube®, an automated system in which the behaviors of compound-treated mice in response to multiple challenges are captured by digital video and analyzed with computer algorithms (Roberds et al., Frontiers in Neuroscience, 2011, Vol. 5, Art. 103, 1-4). In this way, the neuro-pharmacological effects of a test compound can be predicted by similarity to major classes of compounds, such as antipsychotics, anxiolytics and antidepressants. Examples 35, 47, 62 and 93 show similarity to atypical antipsychotics. The results are shown in Table 2.

Objects of the present invention are compounds of formula I for use in the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems. Further objects of the present invention are novel compounds, medicaments containing such novel compounds as well as methods for preparation of compounds of formula I, a combination of compounds of formula I with marketed antipsychotics, antidepressants, anxiolytics or mood stabilizers, and methods for the treatment of CNS disorders as mentioned above.

Compounds of formula I for use in the treatment of the above mentioned CNS diseases are the followings:
1-Cyclopropyl-6-(5-(4-fluorophenyl)-1H-imidazol-2-yl)-3,3-dimethylindolin-2-one
1,3,3-Trimethyl-6-(5-phenyl-1H-imidazol-2-yl)indolin-2-one
1,3,3-Trimethyl-6-(2-(pyridin-4-yl)-1H-imidazol-5-yl)indolin-2-one
1-Cyclopropyl-3,3-dimethyl-6-(3-(pyridin-4-yl)-1,2,4-oxadiazol-5-yl)indolin-2-one
1-Cyclopropyl-3,3-dimethyl-6-(5-(pyridin-4-yl)-1,2,4-oxadiazol-3-yl)indolin-2-one
3,3-Dimethyl-1-oxetan-3-yl-6-(3-pyridin-4-yl-[1,2,4]oxadiazol-5-yl)-1,3-dihydro-indol-2-one
1,3,3-Trimethyl-6-(2-(pyridin-3-yl)oxazol-5-yl)indolin-2-one
1-Cyclopropyl-3,3-dimethyl-6-(2-(pyridin-3-yl)oxazol-5-yl)indolin-2-one
1-Cyclopropyl-3,3-dimethyl-6-(5-(pyridin-3-yl)oxazol-2-yl)indolin-2-one
1-Cyclopropyl-3,3-dimethyl-6-(2-(pyridin-4-yl)oxazol-5-yl)indolin-2-one
3,3-Dimethyl-1-(oxetan-3-yl)-6-(5-(pyridin-4-yl)-1,3,4-oxadiazol-2-yl)indolin-2-one
1-Cyclopropyl-3,3-dimethyl-6-(2-(2-methylpyridin-4-yl)oxazol-5-yl)indolin-2-one 1,3,3-Trimethyl-6-(5-(pyridin-4-yl)-1,3,4-oxadiazol-2-yl)indolin-2-one
1-Cyclopropyl-3,3-dimethyl-6-(2-(2-methylpyridin-4-yl)thiazol-5-yl)indolin-2-one
1-Cyclopropyl-3,3-dimethyl-6-(4-(pyridin-3-yl)oxazol-2-yl)indolin-2-one
1-Cyclopropyl-3,3-dimethyl-6-(4-(pyridin-4-yl)oxazol-2-yl)indolin-2-one
1-Cyclopropyl-3,3-dimethyl-6-(4-(2-methylpyridin-4-yl)oxazol-2-yl)indolin-2-one
1,3,3-Trimethyl-6-(2-(2-methylpyridin-4-yl)thiazol-5-yl)indolin-2-one
1-Cyclopropyl-3,3-dimethyl-6-(5-(2-methylpyridin-4-yl)oxazol-2-yl)indolin-2-one
1,3,3-Trimethyl-6-(4-(pyridin-4-yl)-1H-imidazol-1-yl)indolin-2-one
1,3,3-Trimethyl-6-(4-(pyridin-3-yl)oxazol-2-yl)indolin-2-one
1,3,3-Trimethyl-6-(2-(2-methylpyridin-4-yl)oxazol-5-yl)indolin-2-one
3,3-Dimethyl-1-(oxetan-3-yl)-6-(2-(pyridin-3-yl)oxazol-5-yl)indolin-2-one
3,3-Dimethyl-6-(2-(6-methylpyridin-3-yl)oxazol-5-yl)-1-(oxetan-3-yl)indolin-2-one
3,3-Dimethyl-6-(2-(pyridin-3-yl)oxazol-5-yl)indolin-2-one
3,3-Dimethyl-6-(2-(2-methylpyridin-4-yl)oxazol-5-yl)-1-(oxetan-3-yl)indolin-2-one
3,3-Dimethyl-6-(2-(6-methylpyridin-3-yl)oxazol-5-yl)indolin-2-one
1-(2-Hydroxyethyl)-3,3-dimethyl-6-(5-(pyridin-4-yl)-1,3,4-oxadiazol-2-yl)indolin-2-one
1,3,3-Trimethyl-6-(4-(pyridin-3-yl)-1H-imidazol-1-yl)indolin-2-one
3,3-Dimethyl-1-(oxetan-3-yl)-6-(4-(pyridin-3-yl)-1H-imidazol-1-yl)indolin-2-one
1,3,3-Trimethyl-6-(4-methyl-2-(pyridin-3-yl)oxazol-5-yl)indolin-2-one
3,3-Dimethyl-6-(4-(pyridin-3-yl)-1H-imidazol-1-yl)indolin-2-one
1-Cyclopropyl-3,3-dimethyl-6-(2-(6-methylpyridin-3-yl)oxazol-5-yl)indolin-2-one
3,3-Dimethyl-1-(oxetan-3-yl)-6-(4-(pyridin-4-yl)-1H-imidazol-1-yl)indolin-2-one
3,3-Dimethyl-6-(2-(2-methylpyridin-4-yl)oxazol-5-yl)indolin-2-one
1,3,3-Trimethyl-6-(4-methyl-2-(6-methylpyridin-3-yl)oxazol-5-yl)indolin-2-one
1-Cyclopropyl-3,3-dimethyl-6-(4-methyl-2-(6-methylpyridin-3-yl)oxazol-5-yl)indolin-2-one
1,3,3-Trimethyl-6-(4-methyl-2-(2-methylpyridin-4-yl)oxazol-5-yl)indolin-2-one
1-Cyclopropyl-3,3-dimethyl-6-(4-methyl-2-(2-methylpyridin-4-yl)oxazol-5-yl)indolin-2-one
1,3,3-Trimethyl-6-(4-(pyridin-4-yl)-1H-pyrazol-1-yl)indolin-2-one
1,3,3-Trimethyl-6-(4-(pyridin-3-yl)-1H-pyrazol-1-yl)indolin-2-one
1,3,3-Trimethyl-6-(3-pyridin-4-yl-isoxazol-5-yl)-1,3-dihydro-indol-2-one
3,3-Dimethyl-1-(oxetan-3-yl)-6-(4-(pyridin-3-yl)-1H-pyrazol-1-yl)indolin-2-one
1,3,3-Trimethyl-6-(2-(pyridin-3-yl)oxazol-4-yl)indolin-2-one
1,3,3-Trimethyl-6-(1-(pyridin-3-yl)-1H-pyrazol-4-yl)indolin-2-one
3,3-Dimethyl-6-(4-(pyridin-4-yl)-1H-imidazol-1-yl)indolin-2-one
1-Cyclopropyl-3,3-dimethyl-6-(4-(pyridin-3-yl)-1H-imidazol-1-yl)indolin-2-one
3,3-Dimethyl-6-(5-(2-methylpyridin-4-yl)-1,3,4-oxadiazol-2-yl)-1-(oxetan-3-yl)indolin-2-one
1,3,3-Trimethyl-6-(1-(pyridin-3-yl)-1H-pyrazol-4-yl)indolin-2-one
3,3-Dimethyl-6-(4-(pyridin-3-yl)-1H-pyrazol-1-yl)indolin-2-one
1-Cyclopropyl-3,3-dimethyl-6-(4-(pyridin-3-yl)-1H-pyrazol-1-yl)indolin-2-one
1-Cyclopropyl-3,3-dimethyl-6-(4-(pyridin-4-yl)-1H-imidazol-1-yl)indolin-2-one
1,3,3-Trimethyl-6-(4-(2-methylpyridin-4-yl)-1H-pyrazol-1-yl)indolin-2-one
1-Cyclopropyl-3,3-dimethyl-6-(4-(2-methylpyridin-4-yl)-1H-pyrazol-1-yl)indolin-2-one
1,3,3-Trimethyl-6-(5-(pyridin-4-yl)-1H-pyrazol-3-yl)indolin-2-one
1,3,3-Trimethyl-6-(4-(pyridin-4-yl)-1H-1,2,3-triazol-1-yl)indolin-2-one
3,3-Dimethyl-6-(4-(2-methylpyridin-4-yl)-1H-pyrazol-1-yl)indolin-2-one
1,3,3-Trimethyl-6-(1-(pyridin-3-yl)-1H-imidazol-4-yl)indolin-2-one
1,3,3-Trimethyl-6-(1-(pyridin-4-yl)-1H-imidazol-4-yl)indolin-2-one
1,3,3-Trimethyl-6-(5-(2-methylpyridin-4-yl)-1H-pyrazol-3-yl)indolin-2-one
1,3,3-Trimethyl-6-(1-(2-methylpyridin-4-yl)-1H-imidazol-4-yl)indolin-2-one
6-(2-(3-Methoxypyridin-4-yl)oxazol-5-yl)-3,3-dimethylindolin-2-one
1,3,3-Trimethyl-6-(3-(2-methylpyridin-4-yl)isoxazol-5-yl)indolin-2-one
1,3,3-Trimethyl-6-(5-(pyridin-3-yl)-1H-pyrazol-3-yl)indolin-2-one
1-Ethyl-3,3-dimethyl-6-(4-(2-methylpyridin-4-yl)-1H-pyrazol-1-yl)indolin-2-one
6-[1-(2-Fluoropyridin-4-yl)imidazol-4-yl]-1,3,3-trimethyl-indol-2-one
1,3,3-Trimethyl-6-(4-(6-methylpyridin-3-yl)-1H-pyrazol-1-yl)indolin-2-one
1-Cyclopropyl-3,3-dimethyl-6-(4-(6-methylpyridin-3-yl)-1H-pyrazol-1-yl)indolin-2-one
3,3-Dimethyl-6-(4-(2-methylpyridin-4-yl)-1H-pyrazol-1-yl)-1-(oxetan-3-yl)indolin-2-one
1-Cyclopropyl-3,3-dimethyl-6-(1-(pyridin-3-yl)-1H-imidazol-4-yl)indolin-2-one
1-Cyclopropyl-3,3-dimethyl-6-(1-(pyridin-4-yl)-1H-imidazol-4-yl)indolin-2-one
6-(1-(3-Fluoropyridin-4-yl)-1H-imidazol-4-yl)-1,3,3-trimethylindolin-2-one
1-Cyclopropyl-3,3-dimethyl-6-(1-(2-methylpyridin-4-yl)-1H-imidazol-4-yl)indolin-2-one
1-Cyclopropyl-3,3-dimethyl-6-(3-(2-methylpyridin-4-yl)isoxazol-5-yl)indolin-2-one
1-Cyclopropyl-6-(1-(3-fluoropyridin-4-yl)-1H-imidazol-4-yl)-3,3-dimethylindolin-2-one
1,3,3-Trimethyl-6-(2-methyl-1-(pyridin-4-yl)-1H-imidazol-4-yl)indolin-2-one
1,3,3-Trimethyl-6-(2-methyl-1-(2-methylpyridin-4-yl)-1H-imidazol-4-yl)indolin-2-one
6-(1-(3-Fluoropyridin-4-yl)-2-methyl-1H-imidazol-4-yl)-1,3,3-trimethylindolin-2-one
1,3,3-Trimethyl-6-(5-(6-methylpyridin-3-yl)-1H-pyrazol-3-yl)indolin-2-one 1,3,3-Trimethyl-6-(1-methyl-5-(2-methylpyridin-4-yl)-1H-pyrazol-3-yl)indolin-2-one
1,3,3-Trimethyl-6-(2-(2-methylpyridin-4-yl)pyrimidin-4-yl)indolin-2-one
1,3,3-Trimethyl-6-(2-(6-methylpyridin-3-yl)pyrimidin-4-yl)indolin-2-one
1,3,3-Trimethyl-6-(4-methyl-3-(2-methylpyridin-4-yl)-1H-pyrazol-5-yl)indolin-2-one
3,3-Dimethyl-6-(2-(6-methylpyridin-3-yl)pyrimidin-4-yl)-1-(oxetan-3-yl)indolin-2-one
1-Cyclopropyl-3,3-dimethyl-6-(2-methyl-1-(2-methylpyridin-4-yl)-1H-imidazol-4-yl)indolin-2-one
1-Cyclopropyl-6-(1-(3-fluoropyridin-4-yl)-2-methyl-1H-imidazol-4-yl)-3,3-dimethylindolin-2-one
1,3,3-Trimethyl-6-(1-(3-methylpyridin-4-yl)-1H-imidazol-4-yl)indolin-2-one
1-Cyclopropyl-3,3-dimethyl-6-(1-(3-methylpyridin-4-yl)-1H-imidazol-4-yl)indolin-2-one
1-Cyclopropyl-3,3-dimethyl-6-(1-(2-methylpyridin-4-yl)-1H-imidazol-4-yl)-1H-pyrrolo[3,2-c]pyridin-2(3H)-one
1-Cyclopropyl-6-(1-(3-fluoropyridin-4-yl)-1H-imidazol-4-yl)-3,3-dimethyl-1H-pyrrolo[3,2-c]pyridin-2(3H)-one
3,3-Dimethyl-6-(1-(2-methylpyridin-4-yl)-1H-imidazol-4-yl)indolin-2-one
3,3-Dimethyl-6-(1-(pyridin-3-yl)-1H-imidazol-4-yl)indolin-2-one
1-Cyclopropyl-3,3-dimethyl-6-[2-(2-methyl-pyridin-4-yl)-oxazol-5-yl]-1,3-dihydro-pyrrolo[3,2-c]pyridin-2-one
6-(1-(5-Fluoro-2-methylpyridin-4-yl)-1H-imidazol-4-yl)-1,3,3-trimethylindolin-2-one
6-(2-(5-Fluoro-2-methylpyridin-4-yl)oxazol-5-yl)-1,3,3-trimethylindolin-2-one
3,3-Dimethyl-6-[5-(2-methyl-pyridin-4-yl)-[1,3,4]oxadiazol-2-yl]-1-oxetan-3-yl-1,3-dihydro-pyrrolo[3,2-c]pyridin-2-one
6-(1-(2-Fluoro-5-methylpyridin-4-yl)-1H-imidazol-4-yl)-1,3,3-trimethylindolin-2-one
6-(2-(2-Fluoro-5-methylpyridin-4-yl)oxazol-5-yl)-1,3,3-trimethylindolin-2-one
6-(5-(5-Fluoro-2-methylpyridin-4-yl)-1,3,4-oxadiazol-2-yl)-1,3,3-trimethylindolin-2-one
1,3,3-Trimethyl-6-(2-(6-methylpyridin-3-yl)pyrimidin-5-yl)indolin-2-one
6-[1-(3-Fluoro-4-pyridyl)imidazol-4-yl]-3,3-dimethyl-1-(6-methyl-3-pyridyl)indolin-2-one
6-[1-(3-Fluoro-4-pyridyl)imidazol-4-yl]-3,3-dimethyl-1-(2-methyl-4-pyridyl)indolin-2-one
3,3-Dimethyl-1-(6-methyl-3-pyridyl)-6-[1-(2-methyl-4-pyridyl)imidazol-4-yl]indolin-2-one
3,3-Dimethyl-1-(6-methyl-3-pyridyl)-6-[1-(3-methyl-4-pyridyl)imidazol-4-yl]indolin-2-one
3,3-Dimethyl-1-(2-methyl-4-pyridyl)-6-[1-(3-methyl-4-pyridyl)imidazol-4-yl]indolin-2-one
3,3-Dimethyl-1-(2-methylpyridin-4-yl)-6-(1-(2-methylpyridin-4-yl)-1H-imidazol-4-yl)indolin-2-one
6-(1-(3-Fluoropyridin-4-yl)-1H-imidazol-4-yl)-3,3-dimethyl-1-(1-methyl-1H-imidazol-4-yl)indolin-2-one
6-(1-(3-Fluoropyridin-4-yl)-1H-imidazol-4-yl)-3,3-dimethyl-1-(1-methyl-1H-pyrazol-3-yl)indolin-2-one
6-[1-(3-Fluoro-4-pyridyl)imidazol-4-yl]-3,3-dimethyl-1-(2-methylpyrimidin-5-yl)indolin-2-one
3,3-Dimethyl-1-(1-methylimidazol-4-yl)-6-[1-(2-methyl-4-pyridyl)imidazol-4-yl]indolin-2-one
3,3-Dimethyl-1-(1-methylpyrazol-3-yl)-6-[1-(2-methyl-4-pyridyl)imidazol-4-yl]indolin-2-one
3,3-Dimethyl-6-[1-(2-methyl-4-pyridyl)imidazol-4-yl]-1-(2-methylpyrimidin-5-yl)indolin-2-one
3,3-Dimethyl-1-(1-methylimidazol-4-yl)-6-[1-(3-methyl-4-pyridyl)imidazol-4-yl]indolin-2-one
3,3-Dimethyl-1-(1-methylpyrazol-3-yl)-6-[1-(3-methyl-4-pyridyl)imidazol-4-yl]indolin-2-one
3,3-Dimethyl-6-[1-(3-methyl-4-pyridyl)imidazol-4-yl]-1-(2-methylpyrimidin-5-yl)indolin-2-one
1-Cyclopropyl-3,3-dimethyl-6-(1-(2-methylpyrimidin-5-yl)-1H-imidazol-4-yl)indolin-2-one
1-Cyclopropyl-3,3-dimethyl-6-(1-(5-methylpyrimidin-2-yl)-1H-imidazol-4-yl)indolin-2-one
1,3,3-Trimethyl-6-(1-(5-methylpyrimidin-2-yl)-1H-imidazol-4-yl)indolin-2-one
1,3,3-Trimethyl-6-(1-(2-methylpyrimidin-5-yl)-1H-imidazol-4-yl)indolin-2-one
3,3-Dimethyl-6-(1-(2-methylpyrimidin-5-yl)-1H-imidazol-4-yl)indolin-2-one
3,3-Dimethyl-6-(1-(5-methylpyrimidin-2-yl)-1H-imidazol-4-yl)indolin-2-one
3,3-Dimethyl-6-(1-(6-methylpyridin-2-yl)-1H-imidazol-4-yl)indolin-2-one
6-[4-(5-Fluoro-2-methyl-4-pyridyl)imidazol-1-yl]-1,3,3-trimethyl-indolin-2-one
1,3,3-Trimethyl-6-[5-(3-methyl-4-pyridyl)isoxazol-3-yl]indolin-2-one
1,3,3-Trimethyl-6-[4-(3-methyl-4-pyridyl)imidazol-1-yl]indolin-2-one
1,3,3-Trimethyl-6-[4-(2-methyl-4-pyridyl)imidazol-1-yl]indolin-2-one
6-[4-(2-Fluoro-4-pyridyl)imidazol-1-yl]-1,3,3-trimethyl-indolin-2-one
1-(3-Cyclopropylsulfonylpropyl)-6-[1-(3-fluoro-4-pyridyl)imidazol-4-yl]-3,3-dimethyl-indolin-2-one
6-[1-(3-Fluoro-4-pyridyl)imidazol-4-yl]-1-(2-hydroxyethyl)-3,3-dimethyl-indolin-2-one
1-(3-Cyclopropylsulfonylpropyl)-6-[1-(5-fluoro-2-methyl-4-pyridyl)imidazol-4-yl]-3,3-dimethyl-indolin-2-one or
6-[1-(5-Fluoro-2-methyl-4-pyridyl)imidazol-4-yl]-3,3-dimethyl-indolin-2-one.

One object of the present invention are novel compounds of general formula

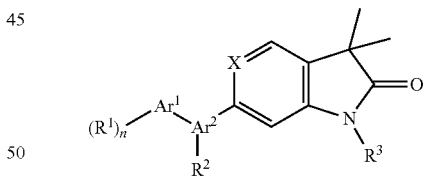

I wherein
Ar$^1$ is phenyl, pyridinyl or pyrimidinyl;
Ar$^2$ is a 5 or 6 membered heteroaryl group, containing 2 or 3 heteroatoms, selected from N, O or S;
R$^1$ is hydrogen, lower alkyl, halogen or lower alkoxy;
R$^2$ is hydrogen or lower alkyl;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;
X is CH or N;
n is 1 or 2;
as well as pharmaceutically acceptable salts thereof, racemic mixtures, or corresponding enantiomers and/or optical isomers and/or stereoisomers thereof, with the exception, that Ar² is not

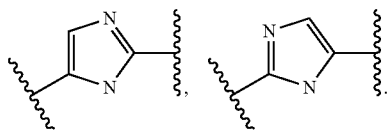 [SMILES: *c1cnc(*)[nH]1 ; *c1cnc(*)[nH]1]

For example the following compounds are with the scope of the invention:
1-Cyclopropyl-3,3-dimethyl-6-(3-(pyridin-4-yl)-1,2,4-oxadiazol-5-yl)indolin-2-one
1-Cyclopropyl-3,3-dimethyl-6-(5-(pyridin-4-yl)-1,2,4-oxadiazol-3-yl)indolin-2-one
3,3-Dimethyl-1-oxetan-3-yl-6-(3-pyridin-4-yl-[1,2,4]oxadiazol-5-yl)-1,3-dihydro-indol-2-one
1,3,3-Trimethyl-6-(2-(pyridin-3-yl)oxazol-5-yl)indolin-2-one
1-Cyclopropyl-3,3-dimethyl-6-(2-(pyridin-3-yl)oxazol-5-yl)indolin-2-one
1-Cyclopropyl-3,3-dimethyl-6-(5-(pyridin-3-yl)oxazol-2-yl)indolin-2-one
1-Cyclopropyl-3,3-dimethyl-6-(2-(pyridin-4-yl)oxazol-5-yl)indolin-2-one
3,3-Dimethyl-1-(oxetan-3-yl)-6-(5-(pyridin-4-yl)-1,3,4-oxadiazol-2-yl)indolin-2-one
1-Cyclopropyl-3,3-dimethyl-6-(2-(2-methylpyridin-4-yl)oxazol-5-yl)indolin-2-one
1,3,3-Trimethyl-6-(5-(pyridin-4-yl)-1,3,4-oxadiazol-2-yl)indolin-2-one
1-Cyclopropyl-3,3-dimethyl-6-(2-(2-methylpyridin-4-yl)thiazol-5-yl)indolin-2-one
1-Cyclopropyl-3,3-dimethyl-6-(4-(pyridin-3-yl)oxazol-2-yl)indolin-2-one
1-Cyclopropyl-3,3-dimethyl-6-(4-(pyridin-4-yl)oxazol-2-yl)indolin-2-one
1-Cyclopropyl-3,3-dimethyl-6-(4-(2-methylpyridin-4-yl)oxazol-2-yl)indolin-2-one
1,3,3-Trimethyl-6-(2-(2-methylpyridin-4-yl)thiazol-5-yl)indolin-2-one
1-Cyclopropyl-3,3-dimethyl-6-(5-(2-methylpyridin-4-yl)oxazol-2-yl)indolin-2-one
1,3,3-Trimethyl-6-(4-(pyridin-4-yl)-1H-imidazol-1-yl)indolin-2-one
1,3,3-Trimethyl-6-(4-(pyridin-3-yl)oxazol-2-yl)indolin-2-one
1,3,3-Trimethyl-6-(2-(2-methylpyridin-4-yl)oxazol-5-yl)indolin-2-one
3,3-Dimethyl-1-(oxetan-3-yl)-6-(2-(pyridin-3-yl)oxazol-5-yl)indolin-2-one
3,3-Dimethyl-6-(2-(6-methylpyridin-3-yl)oxazol-5-yl)-1-(oxetan-3-yl)indolin-2-one
3,3-Dimethyl-6-(2-(pyridin-3-yl)oxazol-5-yl)indolin-2-one
3,3-Dimethyl-6-(2-(2-methylpyridin-4-yl)oxazol-5-yl)-1-(oxetan-3-yl)indolin-2-one
3,3-Dimethyl-6-(2-(6-methylpyridin-3-yl)oxazol-5-yl)indolin-2-one
1-(2-Hydroxyethyl)-3,3-dimethyl-6-(5-(pyridin-4-yl)-1,3,4-oxadiazol-2-yl)indolin-2-one
1,3,3-Trimethyl-6-(4-(pyridin-3-yl)-1H-imidazol-1-yl)indolin-2-one
3,3-Dimethyl-1-(oxetan-3-yl)-6-(4-(pyridin-3-yl)-1H-imidazol-1-yl)indolin-2-one
1,3,3-Trimethyl-6-(4-methyl-2-(pyridin-3-yl)oxazol-5-yl)indolin-2-one
3,3-Dimethyl-6-(4-(pyridin-3-yl)-1H-imidazol-1-yl)indolin-2-one
1-Cyclopropyl-3,3-dimethyl-6-(2-(6-methylpyridin-3-yl)oxazol-5-yl)indolin-2-one
3,3-Dimethyl-1-(oxetan-3-yl)-6-(4-(pyridin-4-yl)-1H-imidazol-1-yl)indolin-2-one
3,3-Dimethyl-6-(2-(2-methylpyridin-4-yl)oxazol-5-yl)indolin-2-one
1,3,3-Trimethyl-6-(4-methyl-2-(6-methylpyridin-3-yl)oxazol-5-yl)indolin-2-one
1-Cyclopropyl-3,3-dimethyl-6-(4-methyl-2-(6-methylpyridin-3-yl)oxazol-5-yl)indolin-2-one
1,3,3-Trimethyl-6-(4-methyl-2-(2-methylpyridin-4-yl)oxazol-5-yl)indolin-2-one
1-Cyclopropyl-3,3-dimethyl-6-(4-methyl-2-(2-methylpyridin-4-yl)oxazol-5-yl)indolin-2-one
1,3,3-Trimethyl-6-(4-(pyridin-4-yl)-1H-pyrazol-1-yl)indolin-2-one
1,3,3-Trimethyl-6-(4-(pyridin-3-yl)-1H-pyrazol-1-yl)indolin-2-one
1,3,3-Trimethyl-6-(3-pyridin-4-yl-isoxazol-5-yl)-1,3-dihydro-indol-2-one
3,3-Dimethyl-1-(oxetan-3-yl)-6-(4-(pyridin-3-yl)-1H-pyrazol-1-yl)indolin-2-one
1,3,3-Trimethyl-6-(2-(pyridin-3-yl)oxazol-4-yl)indolin-2-one
3,3-Dimethyl-1-(oxetan-3-yl)-6-(4-(pyridin-4-yl)-1H-pyrazol-1-yl)indolin-2-one
1,3,3-Trimethyl-6-(1-(pyridin-4-yl)-1H-pyrazol-4-yl)indolin-2-one
3,3-Dimethyl-6-(4-(pyridin-4-yl)-1H-imidazol-1-yl)indolin-2-one
1-Cyclopropyl-3,3-dimethyl-6-(4-(pyridin-3-yl)-1H-imidazol-1-yl)indolin-2-one
3,3-Dimethyl-6-(5-(2-methylpyridin-4-yl)-1,3,4-oxadiazol-2-yl)-1-(oxetan-3-yl)indolin-2-one
1,3,3-Trimethyl-6-(1-(pyridin-3-yl)-1H-pyrazol-4-yl)indolin-2-one
3,3-Dimethyl-6-(4-(pyridin-3-yl)-1H-pyrazol-1-yl)indolin-2-one
1-Cyclopropyl-3,3-dimethyl-6-(4-(pyridin-3-yl)-1H-pyrazol-1-yl)indolin-2-one
1-Cyclopropyl-3,3-dimethyl-6-(4-(pyridin-4-yl)-1H-imidazol-1-yl)indolin-2-one
1,3,3-Trimethyl-6-(4-(2-methylpyridin-4-yl)-1H-pyrazol-1-yl)indolin-2-one
1-Cyclopropyl-3,3-dimethyl-6-(4-(2-methylpyridin-4-yl)-1H-pyrazol-1-yl)indolin-2-one
1,3,3-Trimethyl-6-(5-(pyridin-4-yl)-1H-pyrazol-3-yl)indolin-2-one
1,3,3-Trimethyl-6-(4-(pyridin-4-yl)-1H-1,2,3-triazol-1-yl)indolin-2-one
3,3-Dimethyl-6-(4-(2-methylpyridin-4-yl)-1H-pyrazol-1-yl)indolin-2-one
1,3,3-Trimethyl-6-(1-(pyridin-3-yl)-1H-imidazol-4-yl)indolin-2-one
1,3,3-Trimethyl-6-(1-(pyridin-4-yl)-1H-imidazol-4-yl)indolin-2-one
1,3,3-Trimethyl-6-(5-(2-methylpyridin-4-yl)-1H-pyrazol-3-yl)indolin-2-one
1,3,3-Trimethyl-6-(1-(2-methylpyridin-4-yl)-1H-imidazol-4-yl)indolin-2-one
6-(2-(3-Methoxypyridin-4-yl)oxazol-5-yl)-3,3-dimethylindolin-2-one 1,3,3-Trimethyl-6-(3-(2-methylpyridin-4-yl)isoxazol-5-yl)indolin-2-one
1,3,3-Trimethyl-6-(5-(pyridin-3-yl)-1H-pyrazol-3-yl)indolin-2-one
1-Ethyl-3,3-dimethyl-6-(4-(2-methylpyridin-4-yl)-1H-pyrazol-1-yl)indolin-2-one
6-[1-(2-Fluoropyridin-4-yl)imidazol-4-yl]-1,3,3-trimethyl-indol-2-one
1,3,3-Trimethyl-6-(4-(6-methylpyridin-3-yl)-1H-pyrazol-1-yl)indolin-2-one
1-Cyclopropyl-3,3-dimethyl-6-(4-(6-methylpyridin-3-yl)-1H-pyrazol-1-yl)indolin-2-one
3,3-Dimethyl-6-(4-(2-methylpyridin-4-yl)-1H-pyrazol-1-yl)-1-(oxetan-3-yl)indolin-2-one
1-Cyclopropyl-3,3-dimethyl-6-(1-(pyridin-3-yl)-1H-imidazol-4-yl)indolin-2-one
1-Cyclopropyl-3,3-dimethyl-6-(1-(pyridin-4-yl)-1H-imidazol-4-yl)indolin-2-one
6-(1-(3-Fluoropyridin-4-yl)-1H-imidazol-4-yl)-1,3,3-trimethylindolin-2-one
1-Cyclopropyl-3,3-dimethyl-6-(1-(2-methylpyridin-4-yl)-1H-imidazol-4-yl)indolin-2-one
1-Cyclopropyl-3,3-dimethyl-6-(3-(2-methylpyridin-4-yl)isoxazol-5-yl)indolin-2-one
1-Cyclopropyl-6-(1-(3-fluoropyridin-4-yl)-1H-imidazol-4-yl)-3,3-dimethylindolin-2-one
1,3,3-Trimethyl-6-(2-methyl-1-(pyridin-4-yl)-1H-imidazol-4-yl)indolin-2-one
1,3,3-Trimethyl-6-(2-methyl-1-(2-methylpyridin-4-yl)-1H-imidazol-4-yl)indolin-2-one
6-(1-(3-Fluoropyridin-4-yl)-2-methyl-1H-imidazol-4-yl)-1,3,3-trimethylindolin-2-one
1,3,3-Trimethyl-6-(5-(6-methylpyridin-3-yl)-1H-pyrazol-3-yl)indolin-2-one
1,3,3-Trimethyl-6-(1-methyl-5-(2-methylpyridin-4-yl)-1H-pyrazol-3-yl)indolin-2-one
1,3,3-Trimethyl-6-(2-(2-methylpyridin-4-yl)pyrimidin-4-yl)indolin-2-one
1,3,3-Trimethyl-6-(2-(6-methylpyridin-3-yl)pyrimidin-4-yl)indolin-2-one
1,3,3-Trimethyl-6-(4-methyl-3-(2-methylpyridin-4-yl)-1H-pyrazol-5-yl)indolin-2-one
3,3-Dimethyl-6-(2-(6-methylpyridin-3-yl)pyrimidin-4-yl)-1-(oxetan-3-yl)indolin-2-one
1-Cyclopropyl-3,3-dimethyl-6-(2-methyl-1-(2-methylpyridin-4-yl)-1H-imidazol-4-yl)indolin-2-one
1-Cyclopropyl-6-(1-(3-fluoropyridin-4-yl)-2-methyl-1H-imidazol-4-yl)-3,3-dimethylindolin-2-one
1,3,3-Trimethyl-6-(1-(3-methylpyridin-4-yl)-1H-imidazol-4-yl)indolin-2-one
1-Cyclopropyl-3,3-dimethyl-6-(1-(3-methylpyridin-4-yl)-1H-imidazol-4-yl)indolin-2-one
1-Cyclopropyl-3,3-dimethyl-6-(1-(2-methylpyridin-4-yl)-1H-imidazol-4-yl)-1H-pyrrolo[3,2-c]pyridin-2(3H)-one
1-Cyclopropyl-6-(1-(3-fluoropyridin-4-yl)-1H-imidazol-4-yl)-3,3-dimethyl-1H-pyrrolo[3,2-c]pyridin-2(3H)-one
3,3-Dimethyl-6-(1-(2-methylpyridin-4-yl)-1H-imidazol-4-yl)indolin-2-one
3,3-Dimethyl-6-(1-(pyridin-3-yl)-1H-imidazol-4-yl)indolin-2-one
1-Cyclopropyl-3,3-dimethyl-6-[2-(2-methyl-pyridin-4-yl)-oxazol-5-yl]-1,3-dihydro-pyrrolo[3,2-c]pyridin-2-one
6-(1-(5-Fluoro-2-methylpyridin-4-yl)-1H-imidazol-4-yl)-1,3,3-trimethylindolin-2-one
6-(2-(5-Fluoro-2-methylpyridin-4-yl)oxazol-5-yl)-1,3,3-trimethylindolin-2-one 3,3-Dimethyl-6-[5-(2-methyl-pyridin-4-yl)-[1,3,4]oxadiazol-2-yl]-1-oxetan-3-yl-1,3-dihydro-pyrrolo[3,2-c]pyridin-2-one
6-(1-(2-Fluoro-5-methylpyridin-4-yl)-1H-imidazol-4-yl)-1,3,3-trimethylindolin-2-one
6-(2-(2-Fluoro-5-methylpyridin-4-yl)oxazol-5-yl)-1,3,3-trimethylindolin-2-one
6-(5-(5-Fluoro-2-methylpyridin-4-yl)-1,3,4-oxadiazol-2-yl)-1,3,3-trimethylindolin-2-one
1,3,3-Trimethyl-6-(2-(6-methylpyridin-3-yl)pyrimidin-5-yl)indolin-2-one
6-[1-(3-Fluoro-4-pyridyl)imidazol-4-yl]-3,3-dimethyl-1-(6-methyl-3-pyridyl)indolin-2-one
6-[1-(3-Fluoro-4-pyridyl)imidazol-4-yl]-3,3-dimethyl-1-(2-methyl-4-pyridyl)indolin-2-one
3,3-Dimethyl-1-(6-methyl-3-pyridyl)-6-[1-(2-methyl-4-pyridyl)imidazol-4-yl]indolin-2-one
3,3-Dimethyl-1-(6-methyl-3-pyridyl)-6-[1-(3-methyl-4-pyridyl)imidazol-4-yl]indolin-2-one
3,3-Dimethyl-1-(2-methyl-4-pyridyl)-6-[1-(3-methyl-4-pyridyl)imidazol-4-yl]indolin-2-one
3,3-Dimethyl-1-(2-methylpyridin-4-yl)-6-(1-(2-methylpyridin-4-yl)-1H-imidazol-4-yl)indolin-2-one
6-(1-(3-Fluoropyridin-4-yl)-1H-imidazol-4-yl)-3,3-dimethyl-1-(1-methyl-1H-imidazol-4-yl)indolin-2-one
6-(1-(3-Fluoropyridin-4-yl)-1H-imidazol-4-yl)-3,3-dimethyl-1-(1-methyl-1H-pyrazol-3-yl)indolin-2-one
6-[1-(3-Fluoro-4-pyridyl)imidazol-4-yl]-3,3-dimethyl-1-(2-methylpyrimidin-5-yl)indolin-2-one
3,3-Dimethyl-1-(1-methylimidazol-4-yl)-6-[1-(2-methyl-4-pyridyl)imidazol-4-yl]indolin-2-one
3,3-Dimethyl-1-(1-methylpyrazol-3-yl)-6-[1-(2-methyl-4-pyridyl)imidazol-4-yl]indolin-2-one
3,3-Dimethyl-6-[1-(2-methyl-4-pyridyl)imidazol-4-yl]-1-(2-methylpyrimidin-5-yl)indolin-2-one
3,3-Dimethyl-1-(1-methylimidazol-4-yl)-6-[1-(3-methyl-4-pyridyl)imidazol-4-yl]indolin-2-one
3,3-Dimethyl-1-(1-methylpyrazol-3-yl)-6-[1-(3-methyl-4-pyridyl)imidazol-4-yl]indolin-2-one
3,3-Dimethyl-6-[1-(3-methyl-4-pyridyl)imidazol-4-yl]-1-(2-methylpyrimidin-5-yl)indolin-2-one
1-Cyclopropyl-3,3-dimethyl-6-(1-(2-methylpyrimidin-5-yl)-1H-imidazol-4-yl)indolin-2-one
1-Cyclopropyl-3,3-dimethyl-6-(1-(5-methylpyrimidin-2-yl)-1H-imidazol-4-yl)indolin-2-one
1,3,3-Trimethyl-6-(1-(5-methylpyrimidin-2-yl)-1H-imidazol-4-yl)indolin-2-one
1,3,3-Trimethyl-6-(1-(2-methylpyrimidin-5-yl)-1H-imidazol-4-yl)indolin-2-one
3,3-Dimethyl-6-(1-(2-methylpyrimidin-5-yl)-1H-imidazol-4-yl)indolin-2-one
3,3-Dimethyl-6-(1-(5-methylpyrimidin-2-yl)-1H-imidazol-4-yl)indolin-2-one
3,3-Dimethyl-6-(1-(6-methylpyrimidin-2-yl)-1H-imidazol-4-yl)indolin-2-one
6-[4-(5-Fluoro-2-methyl-4-pyridyl)imidazol-1-yl]-1,3,3-trimethyl-indolin-2-one
1,3,3-Trimethyl-6-[5-(3-methyl-4-pyridyl)isoxazol-3-yl]indolin-2-one
1,3,3-Trimethyl-6-[4-(3-methyl-4-pyridyl)imidazol-1-yl]indolin-2-one
1,3,3-Trimethyl-6-[4-(2-methyl-4-pyridyl)imidazol-1-yl]indolin-2-one
6-[4-(2-Fluoro-4-pyridyl)imidazol-1-yl]-1,3,3-trimethyl-indolin-2-one
1-(3-Cyclopropylsulfonylpropyl)-6-[1-(3-fluoro-4-pyridyl)imidazol-4-yl]-3,3-dimethyl-indolin-2-one 6-[1-(3-Fluoro-4-pyridyl)imidazol-4-yl]-1-(2-hydroxy-ethyl)-3,3-dimethyl-indolin-2-one 1-(3-Cyclopropylsulfonylpropyl)-6-[1-(5-fluoro-2-methyl-4-pyridyl)imidazol-4-yl]-3,3-dimethyl-indolin-2-one or 6-[1-(5-Fluoro-2-methyl-4-pyridyl)imidazol-4-yl]-3,3-dimethyl-indolin-2-one.

One further object of the present invention are compounds of formula Ic

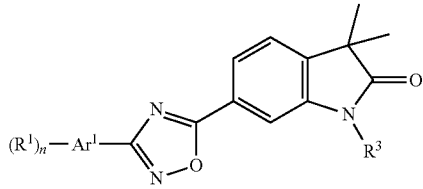

Ic wherein
Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;
n is 1 or 2;
as well as a pharmaceutically acceptable salt thereof, a racemic mixture, or its corresponding enantiomer and/or optical isomer and/or stereoisomer thereof.

One further object of the present invention are compounds of formula Id

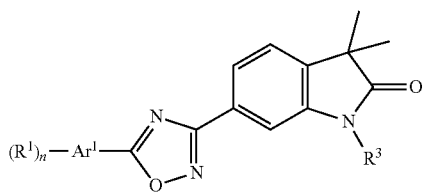

Id wherein
Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;
n is 1 or 2;
as well as a pharmaceutically acceptable salt thereof, a racemic mixture, or its corresponding enantiomer and/or optical isomer and/or stereoisomer thereof.

One further object of the present invention are compounds of formula Ie

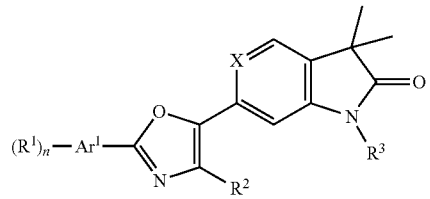

Ie wherein
Ar$^1$ is phenyl, pyridinyl or pyrimidinyl;
R$^1$ is hydrogen, lower alkyl, halogen or lower alkoxy;
R$^2$ is hydrogen or lower alkyl;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;
n is 1 or 2;
as well as a pharmaceutically acceptable salt thereof, a racemic mixture, or its corresponding enantiomer and/or optical isomer and/or stereoisomer thereof.

One further object of the present invention are compounds of formula If

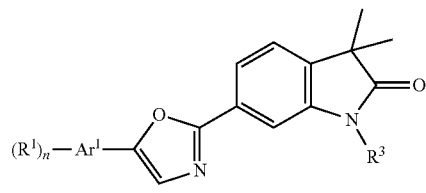

If

Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;
n is 1 or 2;
as well as a pharmaceutically acceptable salt thereof, a racemic mixture, or its corresponding enantiomer and/or optical isomer and/or stereoisomer thereof.

One further object of the present invention are compounds of formula Ig

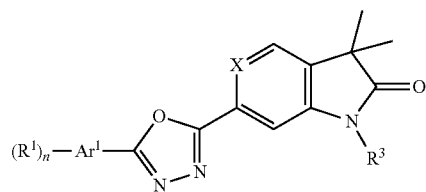

Ig

Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Ih

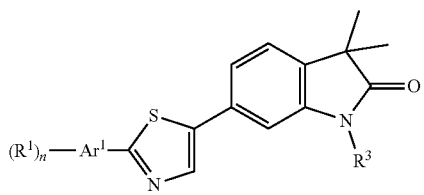

Ih

Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Ik

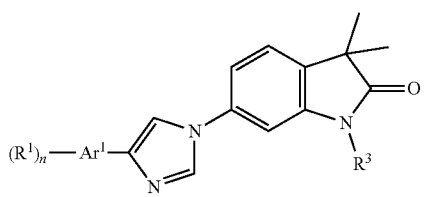

Ik

Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Ii

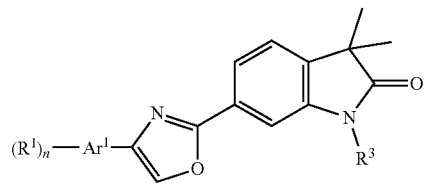

Ii

Ar$^1$ is phenyl, pyridinyl or pyrimidinyl;
R$^1$ is hydrogen, lower alkyl, halogen or lower alkoxy;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Il

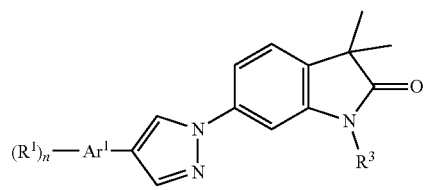

Il

Ar$^1$ is phenyl, pyridinyl or pyrimidinyl;
R$^1$ is hydrogen, lower alkyl, halogen or lower alkoxy;
R$^2$ is hydrogen or lower alkyl;
R$^3$ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Im

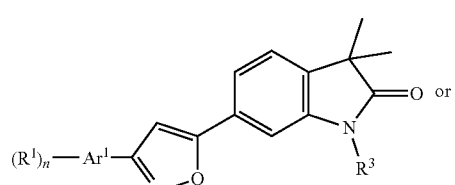

Im or

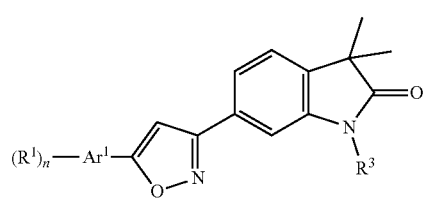

Im'

Ar¹ is phenyl, pyridinyl or pyrimidinyl;

R¹ is hydrogen, lower alkyl, halogen or lower alkoxy;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula In

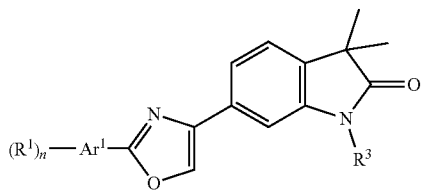

In

Ar¹ is phenyl, pyridinyl or pyrimidinyl;

R¹ is hydrogen, lower alkyl, halogen or lower alkoxy;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Io

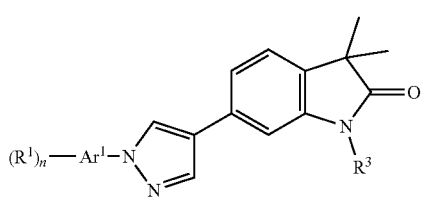

Io

Ar¹ is phenyl, pyridinyl or pyrimidinyl;

R¹ is hydrogen, lower alkyl, halogen or lower alkoxy;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Ip

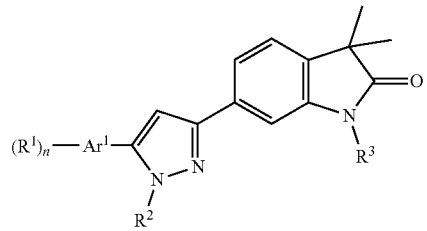

Ip

Ar¹ is phenyl, pyridinyl or pyrimidinyl;

R¹ is hydrogen, lower alkyl, halogen or lower alkoxy;

R² is hydrogen or lower alkyl;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Iq

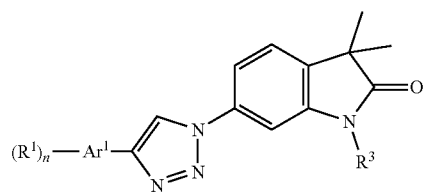

Iq

Ar¹ is phenyl, pyridinyl or pyrimidinyl;

R¹ is hydrogen, lower alkyl, halogen or lower alkoxy;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH$_2$)$_3$—S(O)$_2$-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Ir

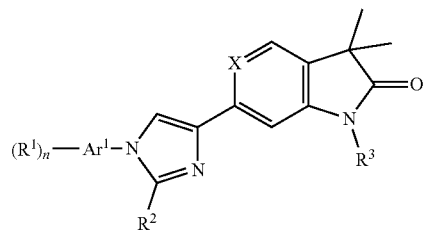

Ir

Ar¹ is phenyl, pyridinyl or pyrimidinyl;

R¹ is hydrogen, lower alkyl, halogen or lower alkoxy;

R² is hydrogen or lower alkyl;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH₂)₃—S(O)₂-cyclopropyl;

n is 1 or 2;

as well as a pharmaceutically acceptable salt thereof, a racemic mixture, or its corresponding enantiomer and/or optical isomer and/or stereoisomer thereof.

One further object of the present invention are compounds of formula Is

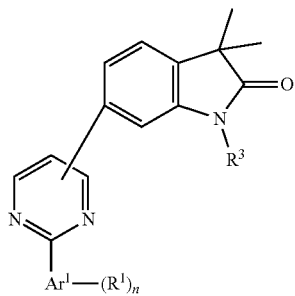

Ar¹ is phenyl, pyridinyl or pyrimidinyl;

R¹ is hydrogen, lower alkyl, halogen or lower alkoxy;

R³ is hydrogen, lower alkyl, lower alkyl substituted by hydroxy, cycloalkyl, oxetan-3-yl, pyridinyl, imidazolyl, pyrazolyl, pyrimidinyl, which rings may optionally substituted by lower alkyl, or is —(CH₂)₃—S(O)₂-cyclopropyl;

n is 1 or 2;

as well as a pharmaceutically acceptable salt thereof, a racemic mixture, or its corresponding enantiomer and/or optical isomer and/or stereoisomer thereof.

Encompassed by the present invention are corresponding prodrugs of compounds of formula I.

A common antipsychotic drug for the treatment of schizophrenia is olanzapine. Olanzapine (Zyprexa) belongs to a drug class known as atypical antipsychotics. Other members of this class include for example clozapine (Clozaril), risperidone (Risperdal), aripiprazole (Abilify) and ziprasidone (Geodon).

Olanzapine is approved for the treatment of psychotic disorders, long term treatment of bipolar disorders and in combination with fluoxetine for the treatment of depressive episodes associated with bipolar disorders and for the treatment of resistant depression.

The compounds of the present invention may be combined with antipsychotic drugs like olanzapine (Zyprexa), clozapine (Clozaril), risperidone (Risperdal), aripiprazole (Abilify), amisulpride (Solian), asenapine (Saphris), blonanserin (Lonasen), clotiapine (Entumine), iloperidone (Fanapt), lurasidone (Latuda), mosapramine (Cremin), paliperidone (Invega), perospirone (Lullan), quetiapine (Seroquel), remoxipride (Roxiam), sertindole (Serdolect), sulpiride (Sulpirid, Eglonyl), ziprasidone (Geodon, Zeldox), zotepine (Nipolept), haloperidol (Haldol, Serenace), droperidol (Droleptan), chlorpromazine (Thorazine, Largactil), fluphenazine (Prolixin), perphenazine (Trilafon), prochlorperazine (Compazine), thioridazine (Mellaril, Melleril), trifluoperazine (Stelazine), triflupromazine (Vesprin), levomepromazine (Nozinan), promethazine (Phenergan), pimozide (Orap) and cyamemazine (Tercian).

One preferred embodiment of the invention is a combination, wherein the marketed antipsychotic drug is olanzapine (Zyprexa), clozapine (Clozaril), risperidone (Risperdal), aripiprazole (Abilify) or ziprasidone.

Furthermore, the compounds of the present invention can be combined with antidepressants such as selective serotonin reuptake inhibitors [Citalopram (Celexa), Escitalopram (Lexapro, Cipralex), Paroxetine (Paxil, Seroxat), Fluoxetine (Prozac), Fluvoxamine (Luvox), Sertraline (Zoloft, Lustral)], serotonin-norepinephrine reuptake inhibitors [Duloxetine (Cymbalta), Milnacipran (Ixel, Savella), Venlafaxine (Effexor), Desvenlafaxine (Pristiq), Tramadol (Tramal, Ultram), Sibutramine (Meridia, Reductil)], serotonin antagonist and reuptake inhibitors [Etoperidone (Axiomin, Etonin), Lubazodone (YM-992, YM-35,995), Nefazodone (Serzone, Nefadar), Trazodone (Desyrel)], norepinephrine reuptake inhibitors [Reboxetine (Edronax), Viloxazine (Vivalan), Atomoxetine (Strattera)], norepinephrine-dopamine reuptake inhibitors [Bupropion (Wellbutrin, Zyban), Dexmethylphenidate (Focalin), Methylphenidate (Ritalin, Concerta)], norepinephrine-dopamine releasing agents [Amphetamine (Adderall), Dextroamphetamine (Dexedrine), Dextromethamphetamine (Desoxyn), Lisdexamfetamine (Vyvanse)], tricyclic antidepressants [Amitriptyline (Elavil, Endep), Clomipramine (Anafranil), Desipramine (Norpramin, Pertofrane), Dosulepin [Dothiepin] (Prothiaden), Doxepin (Adapin, Sinequan), Imipramine (Tofranil), Lofepramine (Feprapax, Gamanil, Lomont), Nortriptyline (Pamelor), Protriptyline (Vivactil), Trimipramine (Surmontil)], tetracyclic antidepressants [Amoxapine (Asendin), Maprotiline (Ludiomil), Mianserin (Bolvidon, Norval, Tolvon), Mirtazapine (Remeron)], monoamine oxidase inhibitors [Isocarboxazid (Marplan), Moclobemide (Aurorix, Manerix), Phenelzine (Nardil), Selegiline [L-Deprenyl] (Eldepryl, Zelapar, Emsam), Tranylcypromine (Parnate), Pirlindole (Pirazidol)], 5-HT1A Receptor Agonists [Buspirone (Buspar), Tandospirone (Sediel), Vilazodone (Viibryd)], 5-HT2 Receptor Antagonists [Agomelatine (Valdoxan), Nefazodone (Nefadar, Serzone), selective Serotonin Reuptake Enhancers [Tianeptine].

A preferred embodiment of this invention is a combination, wherein the marketed anti-depressive drug is citalopram (Celexa), escitalopram (Lexapro, Cipralex), paroxetine (Paxil, Seroxat), fluoxetine (Prozac), sertraline (Zoloft, Lustral) duloxetine (Cymbalta), milnacipran (Ixel, Savella), venlafaxine (Effexor), or mirtazapine (Remeron).

Compounds can also be combined with anxiolytics such as Alprazolam (Helex, Xanax, Xanor, Onax, Alprox, Restyl, Tafil, Paxal), Bretazenil, Bromazepam (Lectopam, Lexotanil, Lexotan, Bromam), Brotizolam (Lendormin, Dormex, Sintonal, Noctilan), Chlordiazepoxide (Librium, Risolid, Elenium), Cinolazepam (Gerodorm), Clonazepam (Rivotril, Klonopin, Iktorivil, Paxam), Clorazepate (Tranxene, Tranxilium), Clotiazepam (Veratran, Clozan, Rize), Cloxazolam (Sepazon, Olcadil), Delorazepam (Dadumir), Diazepam (Antenex, Apaurin, Apzepam, Apozepam, Hexalid, Pax, Stesolid, Stedon, Valium, Vival, Valaxona), Estazolam (ProSom), Etizolam (Etilaam, Pasaden, Depas), Flunitrazepam (Rohypnol, Fluscand, Flunipam, Ronal, Rohydorm), Flurazepam (Dalmadorm, Dalmane), Flutoprazepam (Restas), Halazepam (Paxipam), Ketazolam (Anxon), Loprazolam (Dormonoct), Lorazepam (Ativan, Temesta, Tavor, Lorabenz), Lormetazepam (Loramet, Noctamid, Pronoctan), Medazepam (Nobrium), Midazolam (Dormicum, Versed, Hypnovel, Dormonid), Nimetazepam (Erimin), Nitrazepam (Mogadon, Alodorm, Pacisyn, Dumolid, Nitrazadon), Nordazepam (Madar, Stilny), Oxazepam (Seresta, Serax, Serenid, Serepax, Sobril, Oxabenz, Oxapax), Phenazepam (Phenazepam), Pinazepam (Domar), Prazepam (Lysanxia, Centrax), Premazepam, Quazepam (Doral), Temazepam (Restoril, Normison, Euhypnos, Temaze, Tenox), Tetrazepam (Mylostan), Triazolam (Halcion, Rilamir), Clobazam (Frisium, Urbanol), Eszopiclone (Lunesta), Zaleplon (Sonata, Starnoc), Zolpidem (Ambien, Nytamel, Stilnoct, Stilnox, Zoldem, Zolnod), Zopiclone (Imovane, Rhovane, Ximovan; Zileze; Zimoclone; Zimovane; Zopitan; Zorclone), Pregabalin (Lyrica) and Gabapentin (Fanatrex, Gabarone, Gralise, Neurontin, Nupentin).

One preferred embodiment of the invention is a combination, wherein the marketed anxiolytic drug is alprazolam (Helex, Xanax, Xanor, Onax, Alprox, Restyl, Tafil, Paxal), chlordiazepoxide (Librium, Risolid, Elenium), clonazepam (Rivotril, Klonopin, Iktorivil, Paxam), diazepam (Antenex, Apaurin, Apzepam, Apozepam, Hexalid, Pax, Stesolid, Stedon, Valium, Vival, Valaxona), Estazolam (ProSom), eszopiclone (Lunesta), zaleplon (Sonata, Starnoc), zolpidem (Ambien, Nytamel, Stilnoct, Stilnox, Zoldem, Zolnod), pregabalin (Lyrica) or gabapentin (Fanatrex, Gabarone, Gralise, Neurontin, Nupentin).

A further object of the invention is a combination with mood stabilizers such as Carbamazepine (Tegretol), Lamotrigine (Lamictal), Lithium (Eskalith, Lithane, Lithobid), and Valproic Acid (Depakote).

Compounds can also be combined with procognitive compounds such as donepezil (Aricept), galantamine (Razadyne), rivastigmine (Exelon) and memantine (Namenda).

The preferred indications using the compounds of the present invention are psychotic diseases like schizophrenia.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as defined above, which alkyl group is bonded via an O atom.

As used herein, the term "lower alkyl substituted by hydroxy" denotes a group wherein the alkyl residue is as defined above, wherein at least one hydrogen atom is replaced by a hydroxy group.

The term "cycloalkyl" denotes an alkyl ring with 3-6 carbon ring atoms.

The term "halogen" denotes chlorine, iodine, fluorine and bromine.

The term "5 or 6 membered heteroaryl group, containing 2 or 3 heteroatoms, selected from N, O or S" denotes an aromatic ring, for example the following groups:

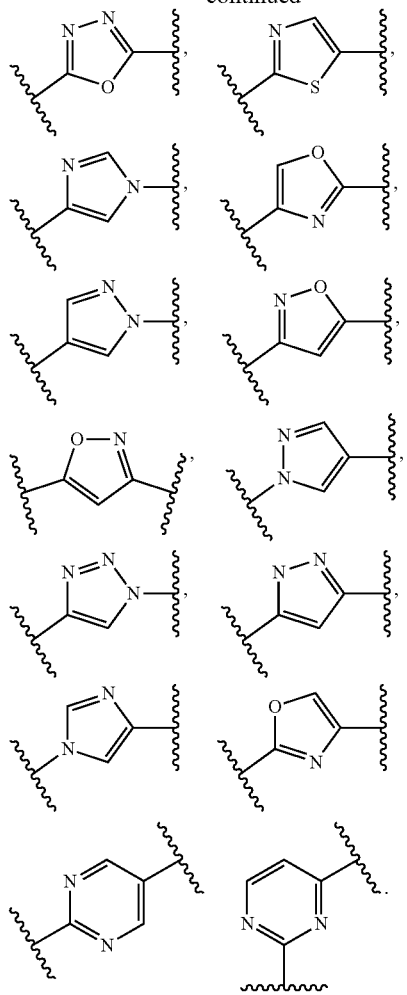

or

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The present compounds of formula I and their pharmaceutically acceptable salts can be prepared by methods known in the art, for example, by processes described below, which processes comprise a) reacting a compound of formula

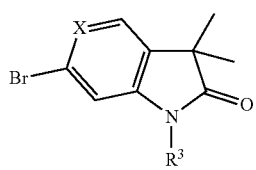

with a compound of formula

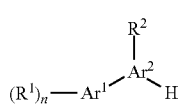

to a compound of formula

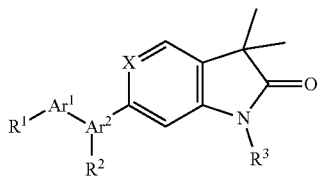

wherein the substituents have the meaning as described above and,
if desired, converting the compounds obtained into pharmaceutically acceptable acid addition salts; or b) reacting a compound of formula

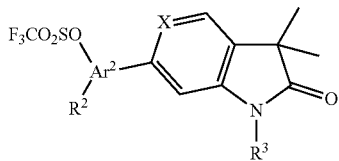

with a compound of formula

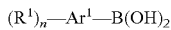

to a compound of formula

I

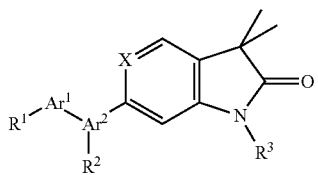

wherein the substituents have the meaning as described above and,
if desired, converting the compounds obtained into pharmaceutically acceptable acid addition salts;

c) reacting a compound of formula

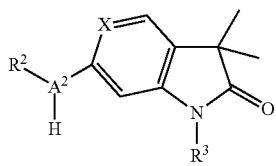

with a compound of formula

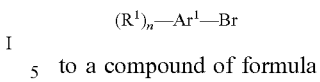

to a compound of formula

I

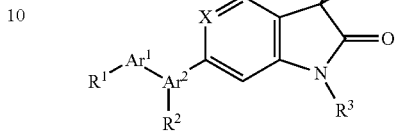

wherein the substituents have the meaning as described above and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Compounds of general formula 2 (X=CH) (Scheme 1) wherein $R^3$ is methyl can e.g. be prepared by trimethylation of 6-halo-oxindoles 1 (X=CH) with Me-LG with LG being a leaving group like iodide, bromide, chloride, tosylate in the presence of a base like sodium hydride and wherein Y is halogen, e.g. bromide.

Scheme 1

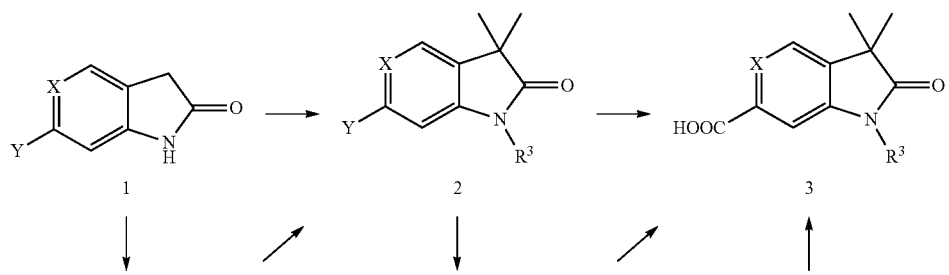

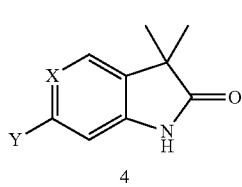
4

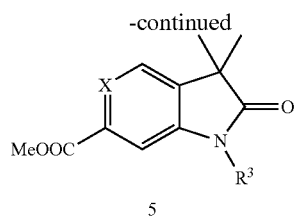
5

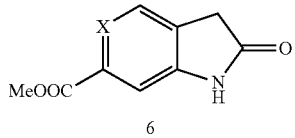
6

Compounds of general formula 2 (X=CH) (Scheme 1) wherein R³ is not methyl can e.g. be prepared by dimethylation of 6-halo-oxindoles 1 (X=CH) with Me-LG (LG being a leaving group like iodide, bromide, chloride, tosylate) in the presence of a base like potassium tert-butoxide and in the presence of copper(I)bromide-dimethylsulfide complex to give the dialkylated product 4 (X=CH). Compounds of general formula 2 (X=CH, N) can be prepared by alkylation of compounds of general formula 4 (X=CH, N) with R³-LG in the presence of a base like sodium hydride or cesium carbonate or by coupling of boronic acids R³—B(OH)₂ or esters R³—B(OR')₂ (e.g. R³-4,4,5,5-tetramethyl-[1,3,2]dioxaborolane) under metal catalysis (like e.g. palladium(0) or copper(II) catalysis) in the presence of a base like e.g. sodium bis(trimethylsilyl)amide or sodium carbonate.

Compounds of formula 5 (X=CH, N) (Scheme 1) can be prepared from general formula 2 (X=CH, N) by carbonylation with carbon monoxide in methanol and in the presence of a ferrocene-palladium catalyst. Hydrolysis of methy esters 5 (X=CH) using e.g. sodium hydroxide yields acids 3 (X=CH). Alternatively, for R³=methyl, acid 3 (X=CH) can be prepared by reaction of the methylester 6 with excess of Me-LG in the presence of excess of a base, e.g. sodium hydride in THF followed by hydrolysis of the intermediate ester using e.g. sodium hydroxide. For R³=H, acid 3 (X=CH) can be prepared by reaction of the methylester 6 with 2 equivalents of Me-LG in the presence of 2 equivalents of a base, e.g. sodium hydride in DMF followed by hydrolysis of the ester group using e.g. sodium hydroxide.

Scheme 2

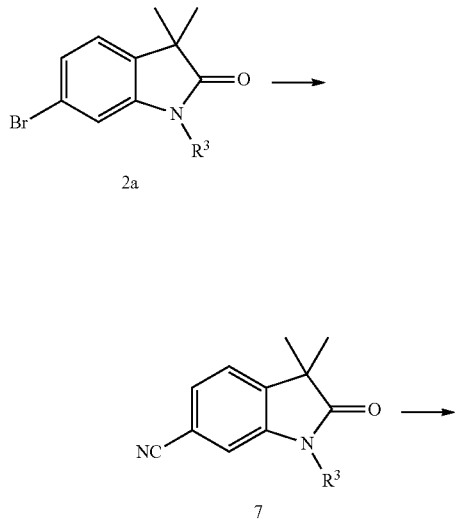

Imidazoles of formula Ia (Scheme 2) can be prepared by substituting bromides 2a with cyanide, e.g. zinc cyanide in the presence of a palladium catalyst to give nitriles 7. Addition of LiHMDS to nitriles 7 followed by acidic hydrolysis provides amidines 8, which can be cyclized with α-bromomethylketones 9 in the presence of a base to afford imidazoles Ia.

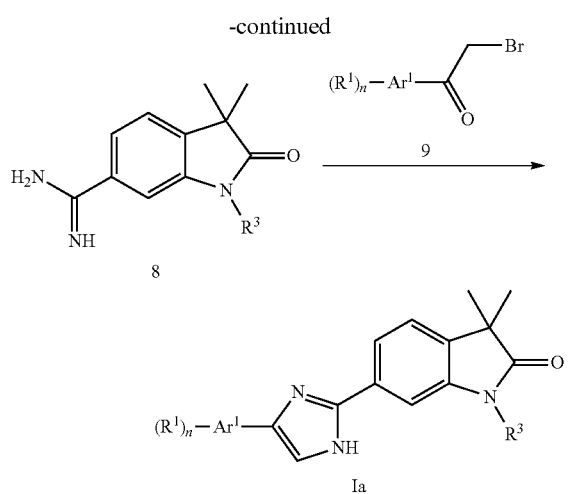

Scheme 3

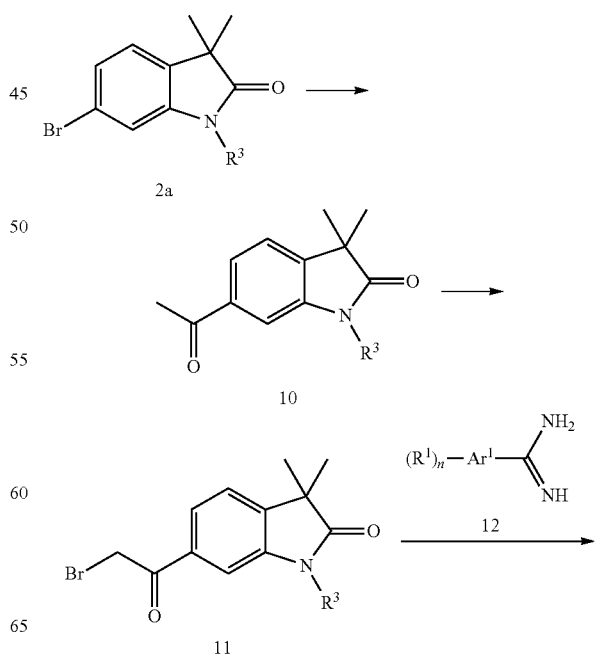

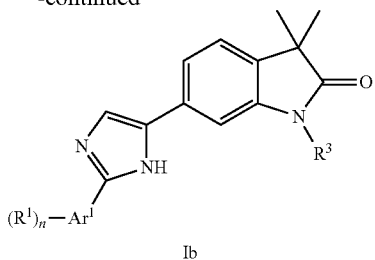

Ib

Imidazoles of formula Ib (Scheme 3) can be prepared starting from bromides 2a, which can be reacted with N-butyl vinylether in the presence of a palladium catalyst to give the methylketones 10. Bromination of 10 with e.g. tetra-N-butylammonium tribromide followed by condensation of the formed α-halomethylketones 11 with amidines 12 yields imidazoles Ib.

Scheme 4

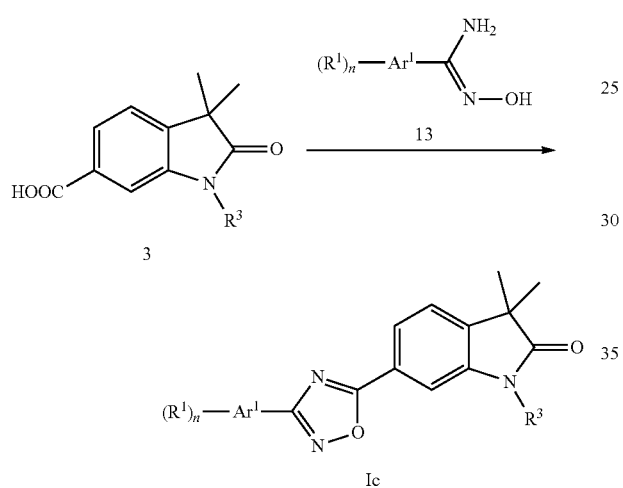

Ic 1,2,4-Oxadiazoles of formula Ic (Scheme 4) can be prepared by condensation of acids 3 (X=CH) with N-hydroxy amidines 13, e.g. in the presence of carbonyldiimidazole.

Scheme 5

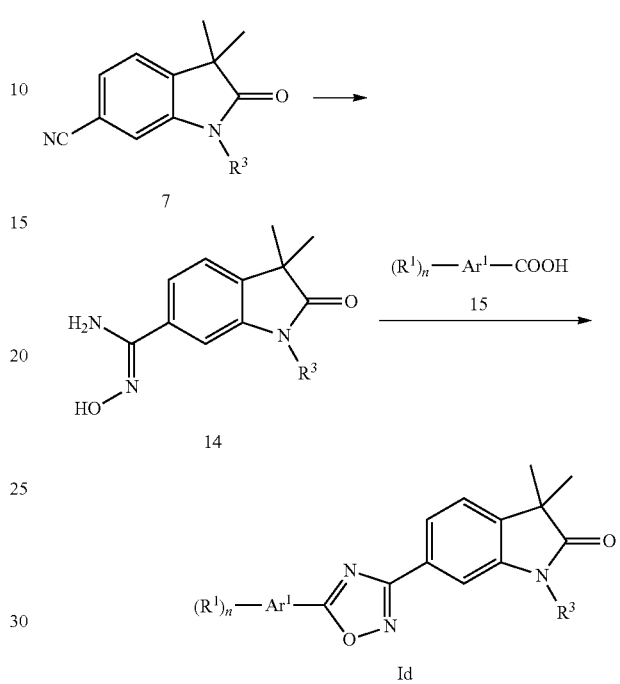

Id 1,2,4-Oxadiazoles of formula Id (Scheme 5) can be prepared by reaction of nitriles 7 with hydroxylamine followed by condensation of the formed N-hydroxy amidines 14 with acids 15, e.g. in the presence of carbonyldiimidazole.

Scheme 6

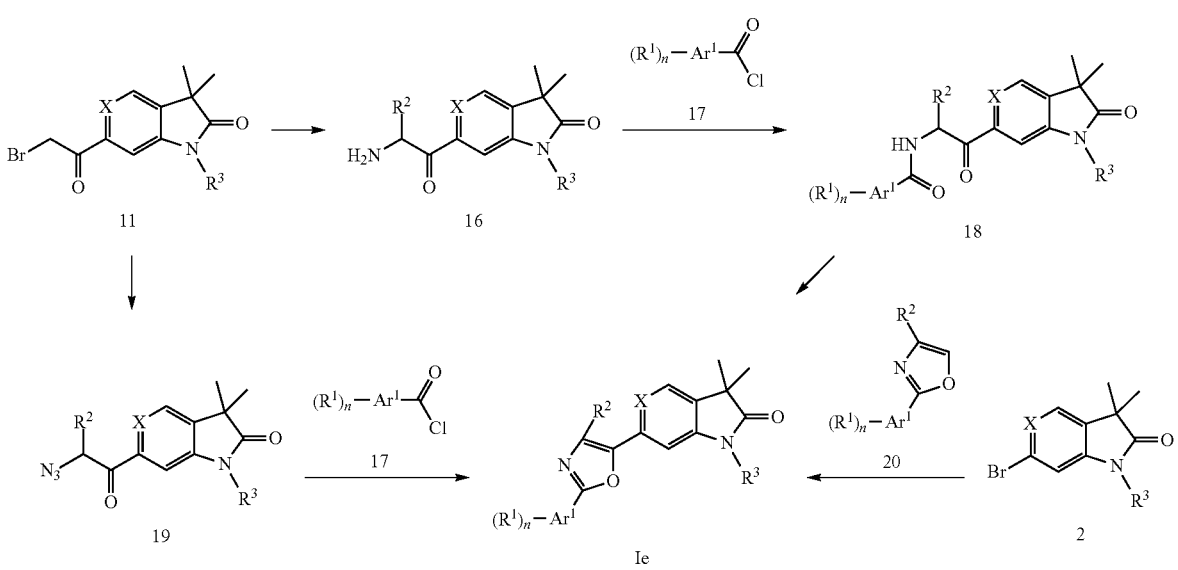

Oxazoles of formula Ie (X=CH) (Scheme 6) can be prepared by reaction of bromides 11 with hexamethylenetetramine to give the aminomethylketones 16, which can be acylated using acid chlorides 17 to give the amides 18. Cyclization of 18 with (methoxycarbonylsulfamoyl)triethylammoniumhydroxid provides oxazoles Ie (X=CH). Alternatively, oxazoles of formula Ie (X=CH) can be prepared by substitution of bromides 11 with sodium azide followed by reaction of the azide 19 with acid chlorides 17 in the presence of triphenylphosphine. In a third method, bromide 2 (X=CH, $R^3$=H) can first be protected with p-methoxybenzyl chloride to give 2 (X=CH, $R^3$=PMB), which can be coupled with oxazoles 20 in the presence of triphenylphosphine, a ferrocene-palladium catalysts and silver carbonate followed by deprotection using TFA to give oxazoles of formula Ie (X=CH). In a fourth method, bromide 2 (X=N, $R^3$=cyclopropyl) can be reacted with oxazoles 20 in the presence of a palladium catalyst, e.g. palladium diacetate and a phosphine ligand, e.g. 2-(dicyclohexylphosphino) biphenyl and cesium carbonate to afford oxazoles Ie (X=N).

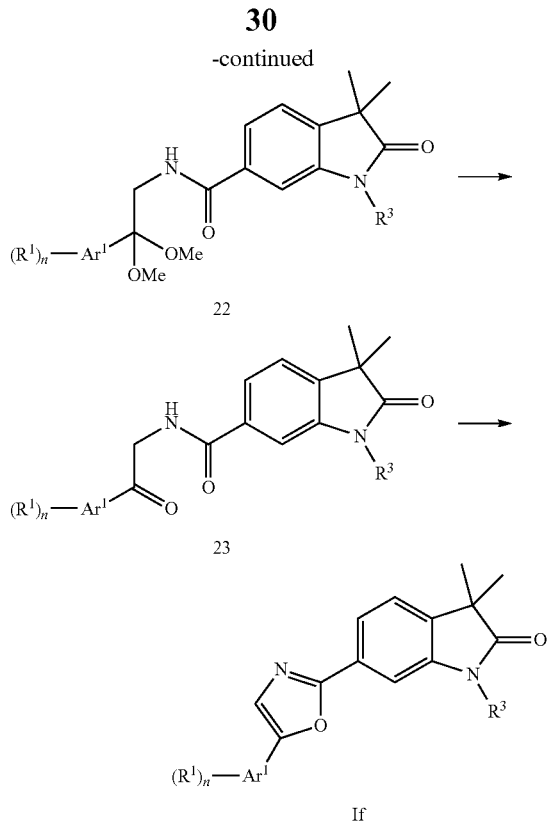

Scheme 7

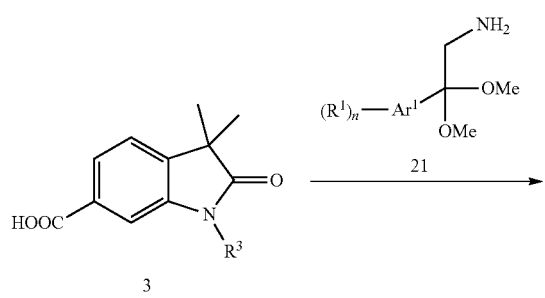

Oxazoles of formula If (Scheme 7) can be prepared starting from acids 3 (X=CH), which can be activated to the intermediate acid chlorides using thionyl chloride followed by coupling with amine 21 to give the amide acetales 22. Deprotection of the acetale group using hydrochloric acid and subsequent cyclization of the formed ketones 23 in the presence of (methoxycarbonylsulfamoyl)triethylammoniumhydroxid furnishes oxazoles of formula If Scheme 8

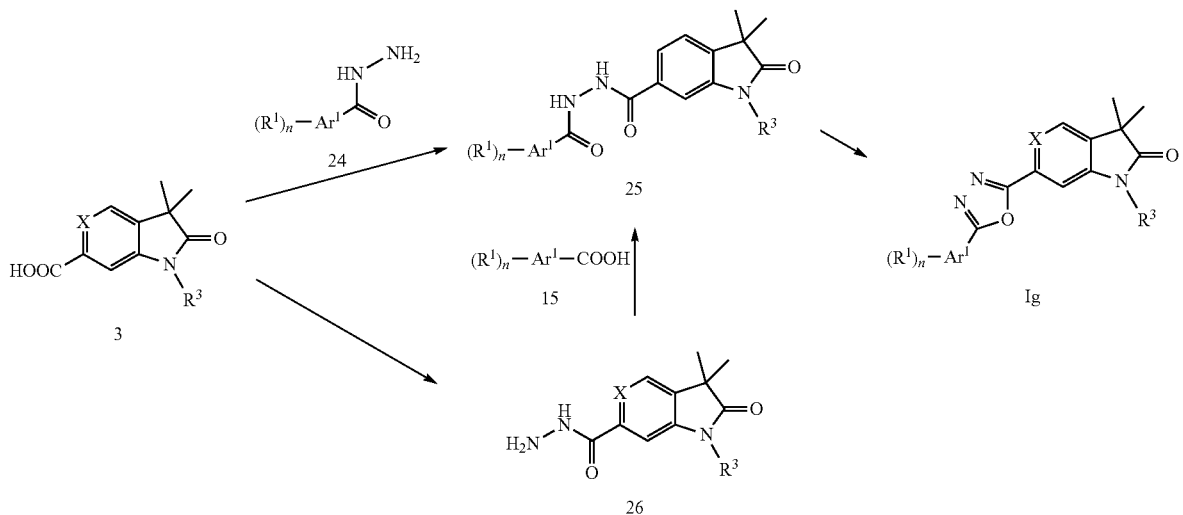

Oxadiazoles of formula Ig (X=CH) (Scheme 8) can be prepared starting from acids 3 (X=CH), which can be reacted with hydrazides 24 in the presence of EDCI and 1H-benzo[d][1,2,3]triazol-1-ol furnishing acetylhydrazides 25 (X=CH). Alternatively, acids 3 (X=N) can be activated to the intermediate acid chlorides using thionyl chloride followed by reaction with hydrazine to give the hydrazides 26 (X=N), which can be coupled with acids 15 to give the acetylhydrazides 25 (X=N). Cyclization of 25 using p-toluensulfonyl cloride affords oxadiazoles of formula Ig.

Scheme 9

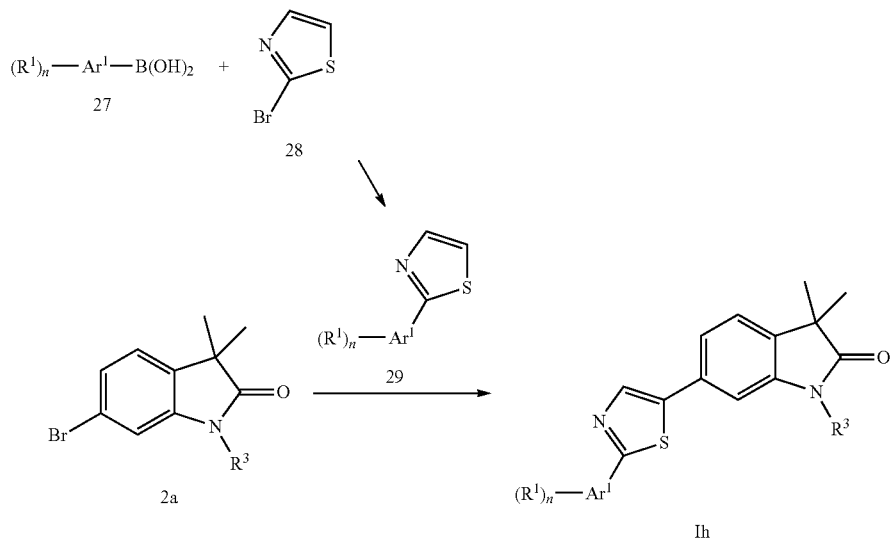

Thiazoles of formula Ih (Scheme 9) can be prepared by coupling of bromides 2a with substituted thiazoles 29, in the presence of triphenylphosphine, a ferrocene-palladium catalysts and silver carbonate. Substituted thiazoles 29 can be obtained by Suzuki coupling of boronic acid 27 with bromothiazole 28 in the presence of a palladium catalyst, e.g. of tetrakis(triphenylphosphine)palladium(0).

Scheme 10

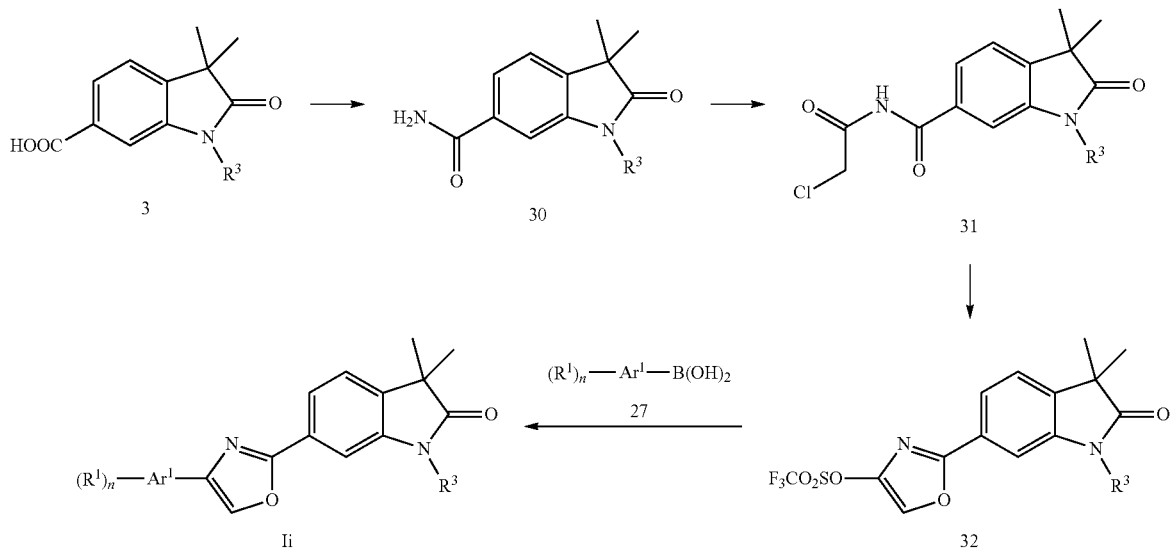

Oxazoles of formula Ii (Scheme 10) can be prepared by converting acids 3 (X=CH) into the in situ generated acid chlorides followed by reaction with ammonia to give the amides 30, which can be reacted with chloroacetyl chloride affording the chloromethylketones 31. Conversion to the 5 oxazole triflates 32 was effected with a base, i.e. sodium hydride followed by reaction with triflic anhydride in the presence of a base, i.e. triethylamine. Suzuki coupling of 32 with boronic acids 27 in the presence of a palladium catalyst, i.e. bis(triphenylphosphine)palladium(II)chloride provided 10 the oxazoles of formula Ii.

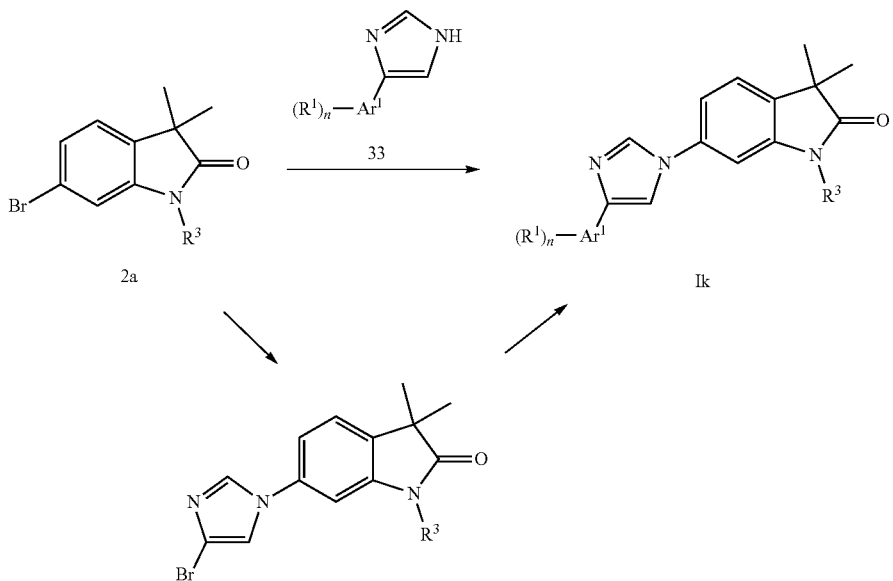

Imidazoles of formula Ik (Scheme 11) can be prepared by coupling bromides 2a with substituted imidazoles 33 in the presence of a catalyst, i.e. copper(I)chloride and 2-acetylcyclohexanon in N-methylpyrrolidone. Substituted imidazoles 33 are known and can be prepared e.g. according to Ganellin et al., J. Med. Chem. 38, 3342, 1995. Alternatively the reaction may be carried out with 4-bromoimidazole leading, which subsequently can be arylated with the corresponding $Ar^1$-boronic acids or $Ar^1$-boronic acid esters in the presence of a base like potassium carbonate or NaOtBu and a catalyst like $PdCl_2(PPh_3)_2$ or Brettphos palladacycle to give compounds of formula Ik.

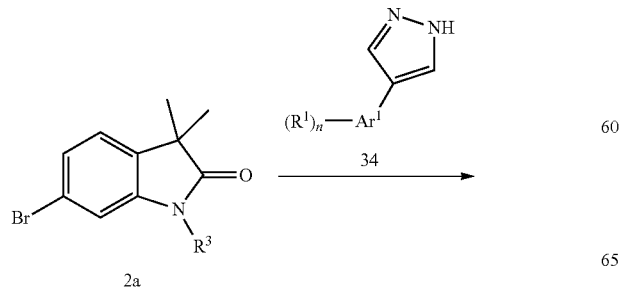

-continued

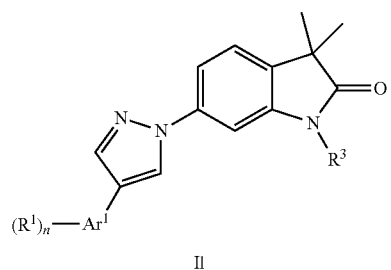

Pyrazoles of formula Il (Scheme 12) can be prepared by coupling bromides 2a with substituted pyrazoles 34 in the presence of a catalyst, i.e. copper(I)chloride and L-proline in DMSO. Substituted pyrazoles 34 are known and can be prepared e.g. according to Bauer et al., J. Med. Chem. 11, 981, 1968.

Scheme 13

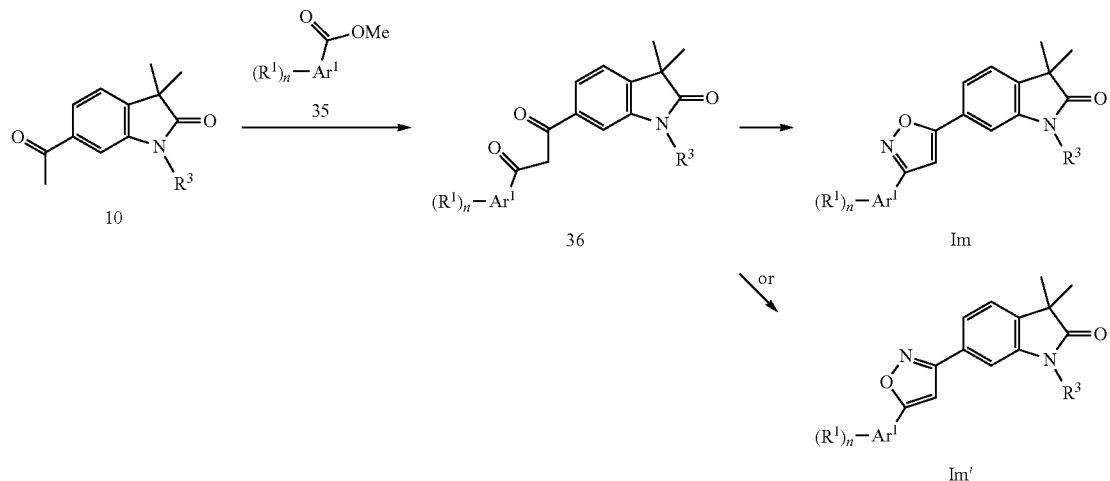

Isoxazoles of formula Im (Scheme 13) can be prepared by reacting methylketones 10 with esters 35 in the presence of a base, i.e. sodium hydride to give diketones 36, which can be cyclized with hydroxylamine furnishing isoxazoles Im and/or Im'.

Scheme 14

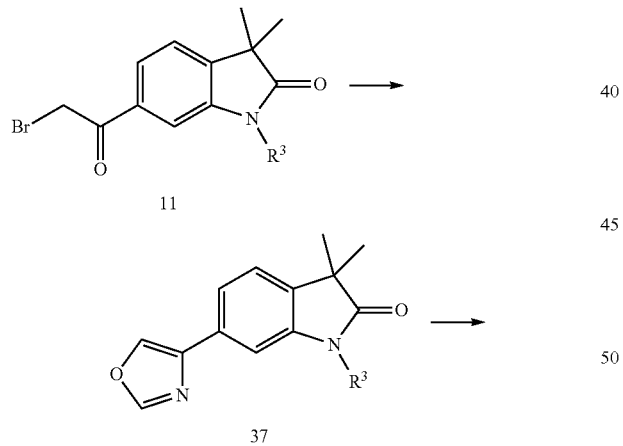

-continued

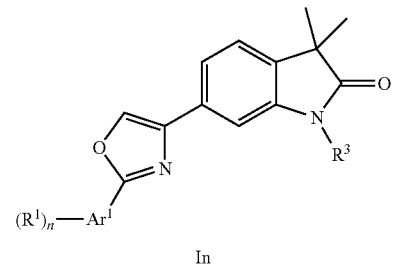

Oxazoles of formula In (Scheme 14) can be prepared by cyclizing bromomethylketones 11 with hydroxylamine to give oxazoles 37, which can be chlorinated using hexachloroethane and a base, e.g. LiHMDS providing chloro-oxazoles 38. Suzuki coupling of 38 with boronic acids 27 in the presence of a palladium catalyst, e.g. bis(triphenylphosphine)palladium(II)dichloride yielded oxazoles In.

Scheme 15

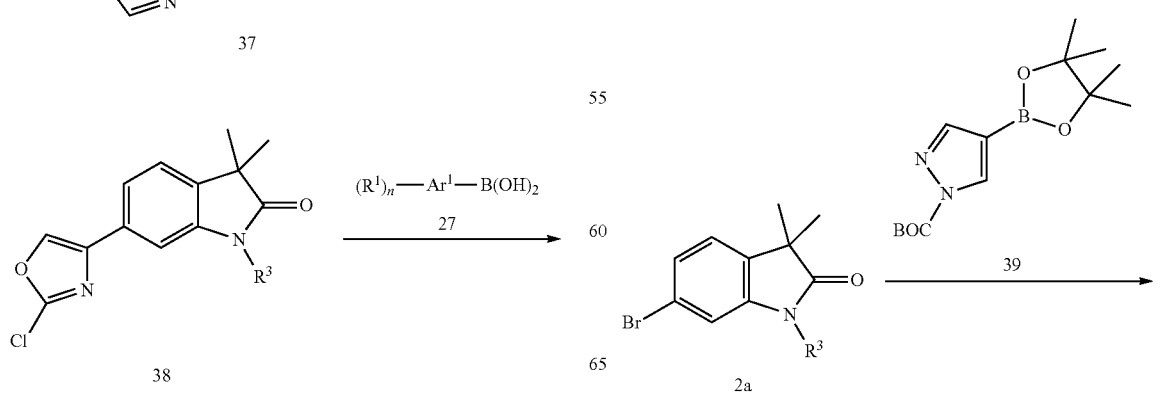

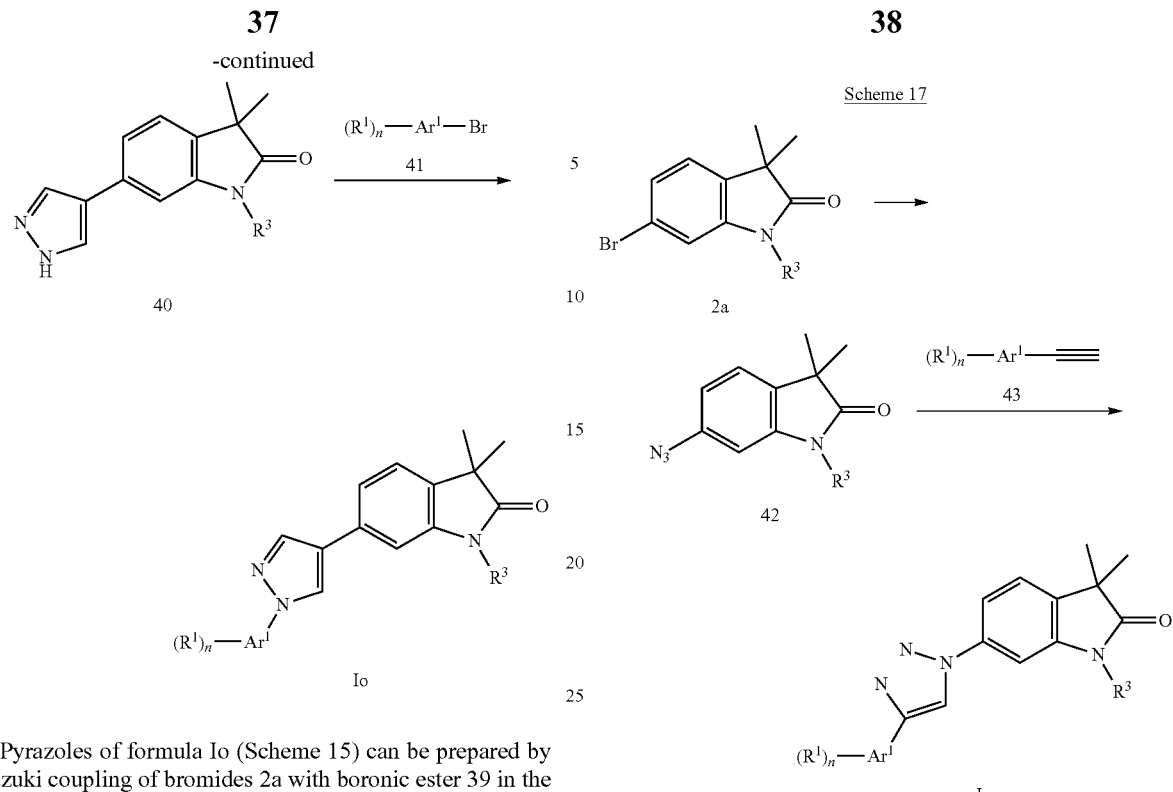

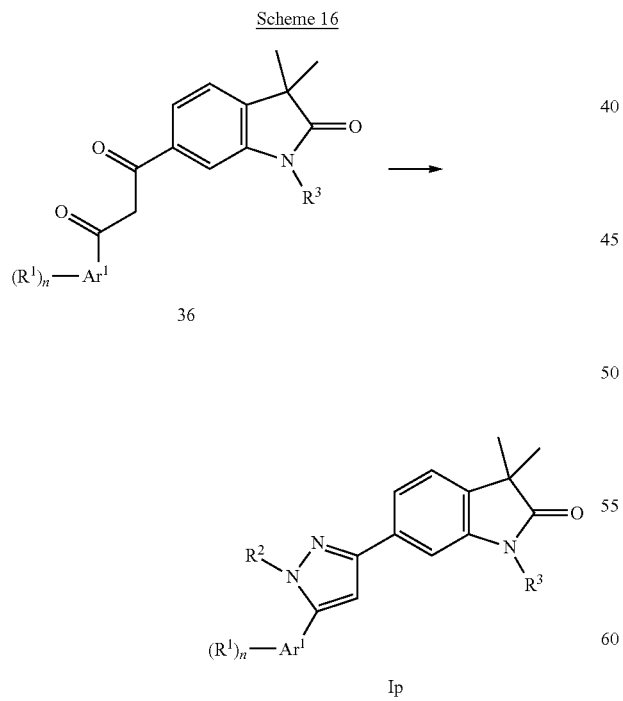

Pyrazoles of formula Io (Scheme 15) can be prepared by Suzuki coupling of bromides 2a with boronic ester 39 in the presence of a palladium catalyst, e.g. [1,1'-bis(diphenylphosphino)ferrocene]dichloropalladium(II) to afford pyrazoles 40, which can be alkylated with bromides 41 in the presence of copper(I)iodide and L-proline in DMSO to give pyrazoles of formula Io.

Imidazoles of formula Ip (Scheme 16) can be prepared from diketones 36 and hydrazine in the presence of a base, e.g. DIPEA to give imidazoles of formula Ip.

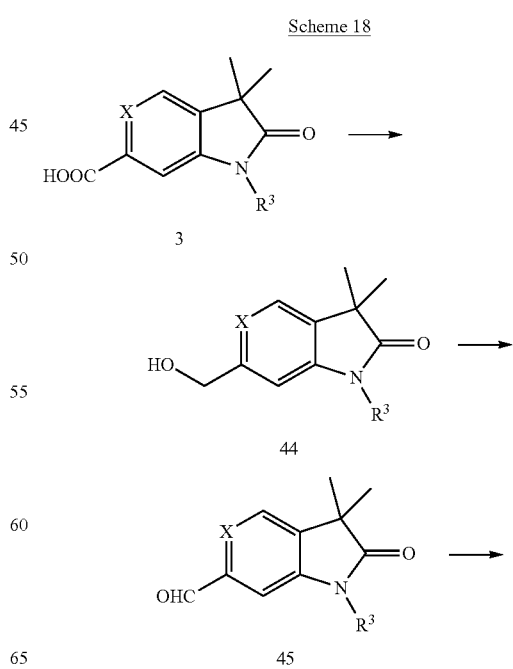

Triazoles of formula Iq (Scheme 17) can be prepared from bromides 2a and an azide, e.g. sodium azide in the presence of ascorbic acid sodium salt and trans-(1R,2R)—N,N'-bismethyl-1,2-cyclohexanediamine to give the azides 42. Cyclization of 42 can be effected with acetylenes 43 in the presence of ascorbic acid sodium salt and copper(II)sulfate in water to give triazoles of formula Iq.

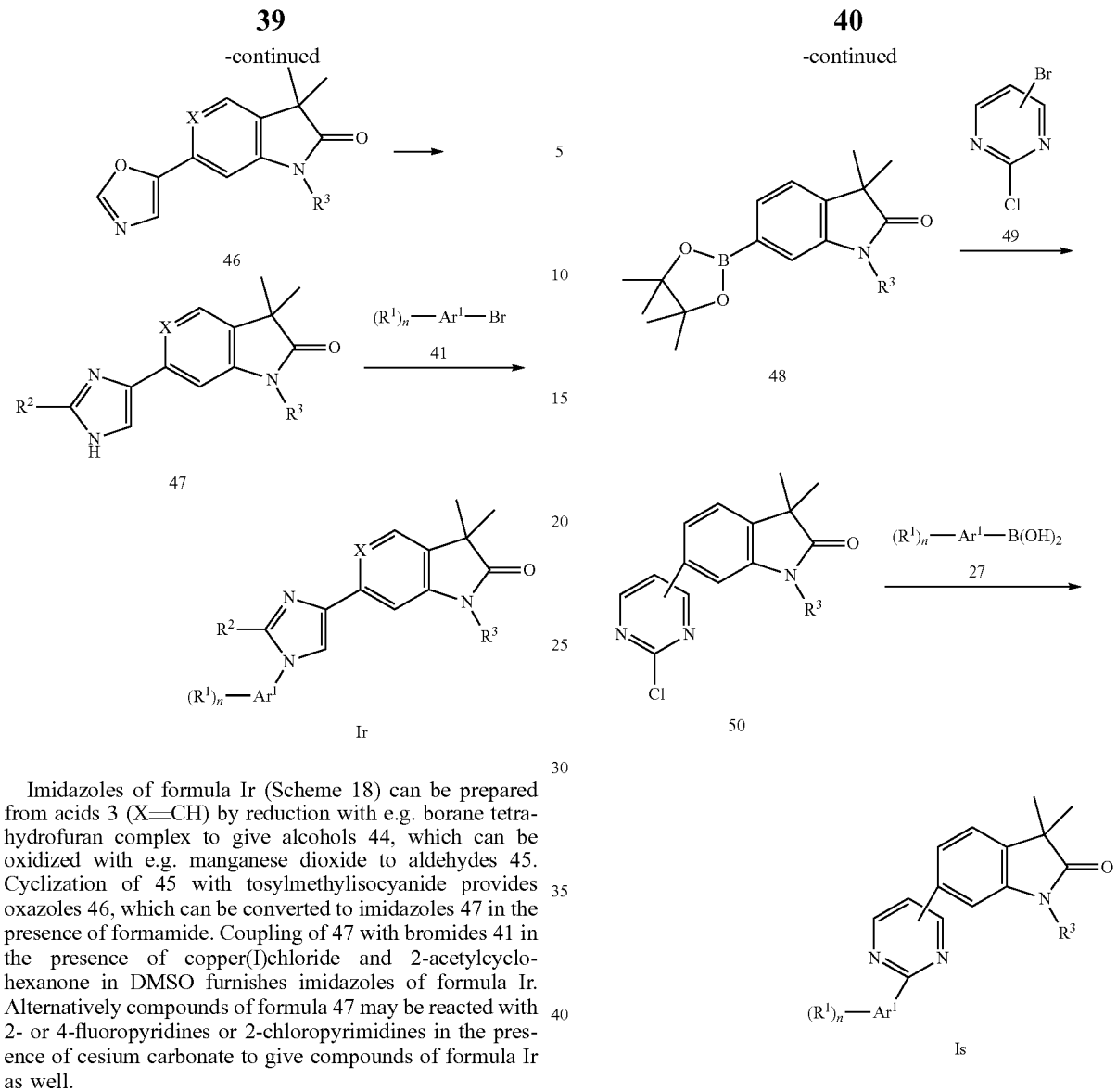

Imidazoles of formula Ir (Scheme 18) can be prepared from acids 3 (X=CH) by reduction with e.g. borane tetrahydrofuran complex to give alcohols 44, which can be oxidized with e.g. manganese dioxide to aldehydes 45. Cyclization of 45 with tosylmethylisocyanide provides oxazoles 46, which can be converted to imidazoles 47 in the presence of formamide. Coupling of 47 with bromides 41 in the presence of copper(I)chloride and 2-acetylcyclohexanone in DMSO furnishes imidazoles of formula Ir. Alternatively compounds of formula 47 may be reacted with 2- or 4-fluoropyridines or 2-chloropyrimidines in the presence of cesium carbonate to give compounds of formula Ir as well.

Scheme 19

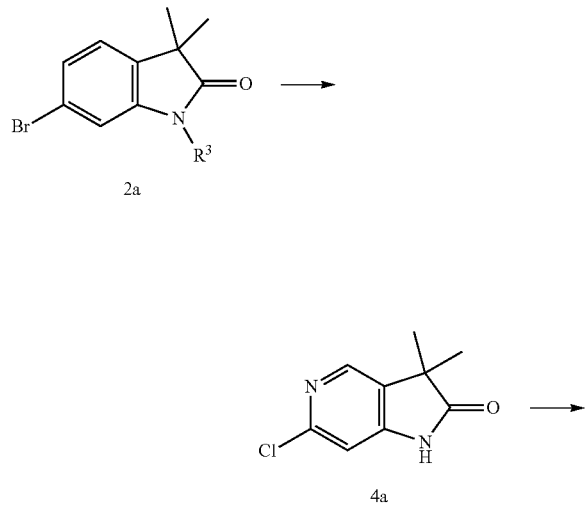

Pyrimidines of formula Is (Scheme 19) can be prepared from bromides 2a by reaction with bis(pinacolato)diboron and a palladium catalyst, e.g. [1,1'-bis(diphenylphosphino)ferrocene]dichloropalladium(II) to give boronic esters 48, which can be coupled with 4-bromo-2-chloropyrimidine or 5-bromo-2-chloropyrimidine in the presence of [1,1'-bis(diphenylphosphino)ferrocene]dichloropalladium(II) affording chloropyrimidines 50. Suzuki coupling of 50 with boronic acids 27 in the presence of [1,1'-bis(diphenylphosphino)ferrocene]dichloropalladium(II) afforded pyrimidines of formula Is Scheme 20

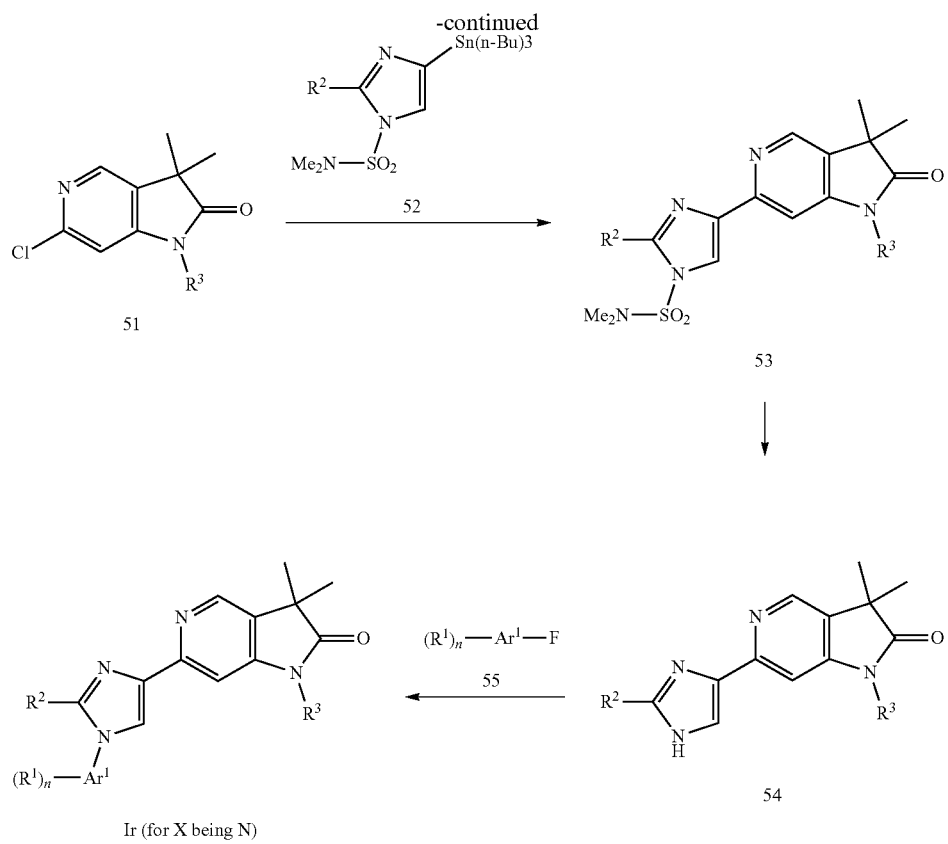

Imidazoles of formula Ir (Scheme 20) can be prepared from the known chloro-pyridine 4a (Woolford et al., WO 2012143726), which can be alkylated with a boronic acid, e.g. cyclopropylboronic acid in the presence of copper(II) acetate and a base, e.g. sodium bis(trimethylsilyl)amide to give alkylated chloro-pyrrolopyridins 51, which can be coupled with N,N-dimethyl-4-(tributylstannyl)-1H-imidazole-1-sulfonamide (prepared according to Altenbach et al., J. Med. Chem. 51, 6571, 2008) and a palladium catalyst, e.g. tetrakis(triphenylphosphine)palladium(0) furnishing sulfonamides 53. Cleavage of the sulfonamide group in 53 can be accomplished with an acid, e.g. aqueous hydrochloric acid providing imidazoles 54, which can be coupled with an aromatic fluoride 55 and a base, e.g. cesium carbonate to give imidazoles of formula Ir.

Scheme 21

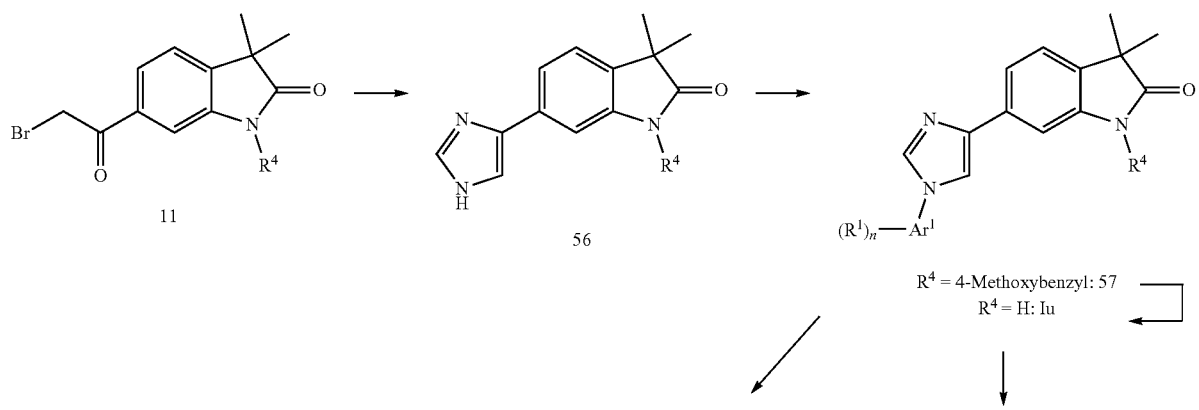

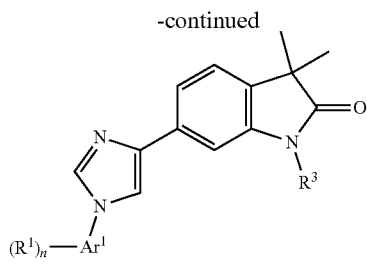

Ir (for X being CH and R² being H)

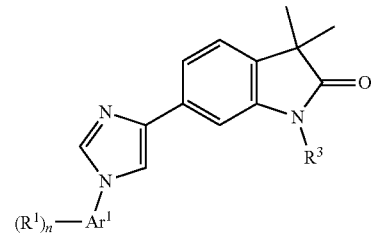

Ir (for X being CH, R² being H and R³ being pyridinyl, imidazolyl, pyrazolyl, pyrimidinyl, opt. substituted by lower alkyl Alternatively to Scheme 18, compounds of formula 56 may be directly prepared from compounds of formula 11 by treatment with formamide. These may be transferred to compounds of formula 57 and Iu by methods depicted in Scheme 18. Compounds of formula 57 may be transformed to compounds of formula Iu by treatment with TFA (Scheme 21). Compounds of formula Iu can be transformed to compounds of formula Ir by reaction with the corresponding heteroaryl bromides in the presence of a base like potassium carbonate, a copper(I) source like CuI and a suitable ligand like N,N'-dimethylethylen-1,2-diamine.

Compounds of formula Ir can be obtained by treatment of compounds with formula Iu with a suitable alkylating agent in the presence of a base like cesium carbonate Experimental Part The following examples are provided for illustration of the invention. They should not be considered as limiting the scope of the invention, but merely as being representative thereof.

Abbreviations

DIPEA, diisopropylethylamine; DMAP, dimethylaminopyridine; DMF, dimethylformamide; DMSO, dimethylsulfoxide; EtOAc, ethyl acetate; HATU, O-(7-azabenzotriazole-1-yl)-N,N,N',N'-tetramethyluronium hexafluorophosphate; LiHMDMS, lithium hexamethyldisilazide; MeOH, methanol; PMB, p-methoxybenzyl; TBAF, tetrabutylammonium fluoride; TBME, tert-butylmethylether; TFA, trifluoroacetic acid; THF, tetrahydrofuran.

General:

Silica gel chromatography was either performed using cartridges packed with silica gel (ISOLUTE® Columns, TELOS™ Flash Columns) or silica-NH₂ gel (TELOS™ Flash NH2 Columns) on ISCO Combi Flash Companion or on glass columns on silica gel 60 (32-60 mesh, 60 Å). MS: Mass spectra (MS) were measured with ion spray positive or negative method on a Perkin-Elmer SCIEX API 300.

Example 1

1-Cyclopropyl-6-(5-(4-fluorophenyl)-1H-imidazol-2-yl)-3,3-dimethylindolin-2-one

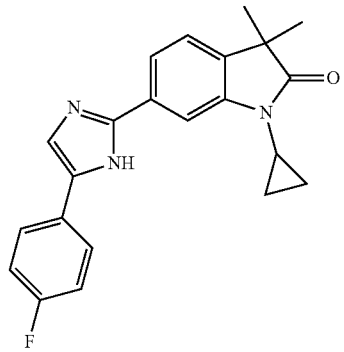 [SMILES: CC1(C)C(=O)N(C2CC2)c2cc(-c3ncc(-c4ccc(F)cc4)[nH]3)ccc21]

a) 6-Bromo-3,3-dimethyl-indolin-2-one

To a suspension of potassium tert-butylate (12.8 g) in dry THF (80 ml) was added portion wise at 0° C. 6-bromoindolin-2-one (5.0 g) followed by copper (I) bromide-dimethylsulfide complex (470 mg). MeI (6.82 g) was added drop wise within 45 min keeping the internal temperature below 8° C., the mixture was warmed to 22° C. and stirring was continued for 16 h. hours. The mixture was quenched at 0° C. with saturated aqueous ammonium chloride solution and diluted with TBME and water. The organic layer was dried, evaporated and the residue purified by flash chromatography (silica gel, EtOAc/n-heptane, 1:1) to give the title compound (5.17 g) as a brown solid (5.17 g, 91%). MS ESI (m/z): 240.4/242.4 [(M+H)⁺].

b) 6-Bromo-1-cyclopropyl-3,3-dimethylindolin-2-one

To a black suspension of 6-bromo-3,3-dimethylindolin-2-one (7.0 g), cyclopropylboronic acid (5.01 g), DMAP (10.7 g) and copper (II) acetate (5.56 g) in toluene (400 ml) was added a solution of sodium bis(trimethylsilyl)amide in THF (2 M, 15.3 ml) while bubbling dry air through the mixture, which was followed by heating to 95° C. for 7 h. The mixture was partitioned between aqueous HCl (2 M) and TBME, the organic layer was washed with aqueous HCl (2 M), dried, evaporated and the residue purified by flash chromatography (silica gel, gradient, 0% to 20% EtOAc in n-heptane) to give the title compound (7.1 g, 87%) as a red solid. MS (ESI, m/z): 280.4/282.4 [(M+H)$^+$].

c) 1-Cyclopropyl-3,3-dimethyl-2-oxoindoline-6-carbonitrile

A suspension of 6-bromo-1-cyclopropyl-3,3-dimethylindolin-2-one (2.0 g) in DMF (36 ml) was flushed with argon, treated with dicyanozinc (1.04 g) and tetrakis(triphenylphosphine)palladium(0) (825 mg) and stirring was continued at 85° C. for 16 h. The mixture was evaporated, the residue partitioned between aqueous sodium carbonate (1 M) and EtOAc, the organic layer was washed with aqueous sodium carbonate (1 M), dried, evaporated and the residue purified by flash chromatography (silica gel, gradient, 0% to 40% EtOAc in n-heptane) to give the title compound (1.61 g, quant.) as a light yellow solid. MS (ESI, m/z): 227.5 [(M+H)$^+$].

d) 1-Cyclopropyl-3,3-dimethyl-2-oxoindoline-6-carboximidamide

To a brown solution of lithium bis(trimethylsilyl)amide in THF (1M, 8.2 m) and dry diethyl ether (17 ml) was added at 0° C. in 3 portions 1-cyclopropyl-3,3-dimethyl-2-oxoindoline-6-carbonitrile (900 mg) and stirring was continued at 22° C. for 21 h. The mixture was cooled to 0° C., treated with hydrochloric acid (6 M, 4.0 ml) and stirring was continued at 0° C. for 40 min and at 22° C. for 5 h. The mixture was partitioned between water and diethyl ether, the pH of the aqueous layer was adjusted to 14 using solid NaOH and extracted with dichloromethane. The organic layer was dried and evaporated to give the crude title compound (537 mg, 56%) as an off-white solid, which was used without further purification. MS (ESI, m/z): 244.5 [(M+H)$^+$].

e) 1-Cyclopropyl-6-(5-(4-fluorophenyl)-1H-imidazol-2-yl)-3,3-dimethylindolin-2-one (Example 1)

A mixture of 1-cyclopropyl-3,3-dimethyl-2-oxoindoline-6-carboximidamide (130 mg) and 2-bromo-1-(4-fluorophenyl)ethanone (151 mg) in an aqueous sodium hydrogencarbonate solution (1 M, 1.9 ml) and THF (120 ml) was heated to reflux temperature for 16 h. The mixture was evaporated, the residue partitioned between water and EtOAc, the organic layer was dried, evaporated and the residue purified by flash chromatography (silica gel, gradient, 0% to 15% MeOH in dichloromethane), which was followed by a second chromatography (Si—NH2, gradient, 0% to 70% EtOAc in n-heptane) to give the title compound (121 mg, 63%) as a white foam. MS (ESI, m/z): 362.6 [(M+H)$^+$].

Example 2

1,3,3-Trimethyl-6-(5-phenyl-1H-imidazol-2-yl)indolin-2-one

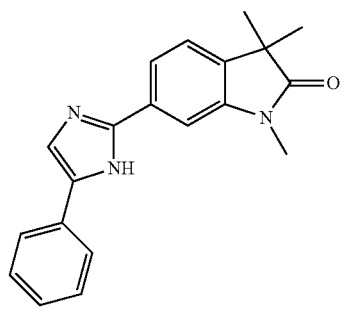 [SMILES: CN1C(=O)C(C)(C)c2ccc(-c3ncc(-c4ccccc4)[nH]3)cc21]

a) 6-Bromo-1,3,3-trimethylindolin-2-one

Under an argon atmosphere NaH (60% on mineral oil, 7.32 g) was suspended in dry THF (45 ml). A suspension of 6-bromoindolin-2-one (10.0 g) in dry THF (108 ml) was added in portions during 10 min keeping the temperature below 27° C. The reaction mixture was warmed to 25° C., MeI (11.4 ml) was added drop wise during 1 h while the internal temperature was carefully kept between 24 and 27° C. and stirring was continued for 18 h. Saturated aqueous NH$_4$Cl solution (20 ml) was carefully added at 10-15° C., the mixture was diluted with EtOAc and saturated aqueous NaHCO$_3$ solution, the organic layer was washed with saturated aqueous NaHCO$_3$ solution, dried and evaporated. The residue was purified by flash chromatography (silica gel, gradient 0% to 30% EtOAc in n-heptane) to give the title compound (10.1 g, 84%) as a light red solid. MS (ESI, m/z): 254.1/256.2 [(M+H)$^+$].

b) 1,3,3-Trimethyl-6-(5-phenyl-1H-imidazol-2-yl)indolin-2-one (Example 2)

6-Bromo-1,3,3-trimethylindolin-2-one was converted in analogy to example 1c-e using bromo-1-(phenyl)ethanone in step e to give the title compound as white solid. MS (ESI, m/z): 318.1 [(M+H)$^+$].

Example 3

1,3,3-Trimethyl-6-(2-(pyridin-4-yl)-1H-imidazol-5-yl)indolin-2-one

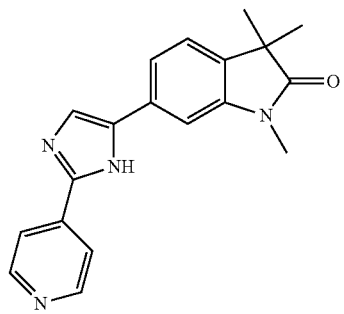 [SMILES: CN1C(=O)C(C)(C)c2ccc(-c3cnc(-c4ccncc4)[nH]3)cc21]

a) 6-Acetyl-1,3,3-trimethylindolin-2-one

A mixture of 6-bromo-1,3,3-trimethylindolin-2-one (1.0 g) from example 2a, 1,3-bis(diphenylphosphino)propane (418 mg), palladium (II) acetate (88 mg), N-butyl vinylether (1.63 g) and potassium carbonate (653 mg) in DMF (14 ml) and water (1.4 ml) was flushed with argon for 5 min and heated in a microwave oven at 120° C. for 1 h. The mixture treated at 22° C. with aqueous hydrochloric acid (2 N, 7.5 ml) and stirring was continued for 3 h. The mixture was partitioned between saturated aqueous ammonium hydrogencarbonate and EtOAc, the organic layer was dried, evaporated and the residue purified by flash chromatography (silica gel, gradient, 0% to 50% EtOAc in n-heptane) to give the title compound (660 mg, 77%) as a light yellow solid. MS (ESI, m/z): 218.5 [(M+H)$^+$].

b) 6-(2-Bromoacetyl)-1,3,3-trimethylindolin-2-one

To a solution of 6-acetyl-1,3,3-trimethylindolin-2-one (660 mg) in THF (20 ml) and MeOH (12 ml) was added a solution of tetra-n-butylammonium tribromide (1.49 g) in THF (7 ml) and stirring was continued at 45° C. for 17 h. The mixture was partitioned between water and EtOAc, the organic layer was dried, evaporated and the residue purified twice by flash chromatography (silica gel, gradient, 0% to 50% EtOAc in n-heptane) to give the title compound (646 mg, 72%) as a light brown liquid. MS (ESI, m/z): 296.3/298.3 [(M+H)$^+$].

c) 1,3,3-Trimethyl-6-(2-(pyridin-4-yl)-1H-imidazol-5-yl)indolin-2-one (Example 3)

A mixture of isonicotinimidamide hydrochloride (511 mg) in an aqueous sodium hydrogencarbonate solution (1 M, 4.3 ml) and THF (225 ml) was stirred at 22° C. for 20 min. A solution of 6-(2-bromoacetyl)-1,3,3-trimethylindolin-2-one (320 mg) in THF (16 ml) was added and heated to reflux temperature for 22 h. The mixture was evaporated, the residue partitioned between water and EtOAc, the organic layer was dried, evaporated and the residue purified twice by flash chromatography (silica gel, gradient, 0% to 15% MeOH in dichloromethane containing 1% NH3), to give the title compound (168 mg, 48%) as a light yellow foam. MS (ESI, m/z): 319.5 [(M+H)$^+$].

Example 4

1-Cyclopropyl-3,3-dimethyl-6-(3-(pyridin-4-yl)-1,2,4-oxadiazol-5-yl)indolin-2-one a) Methyl 1-cyclopropyl-3,3-dimethyl-2-oxoindoline-6-carboxylate

To a solution of 6-bromo-1-cyclopropyl-3,3-dimethylindolin-2-one from example 1b (3.0 g), triethylamine (2.18 g) in EtOAc (40 ml) and MeOH (40 ml) was added 1,1'-bis(diphenylphosphino)ferrocene-palladium(II)dichloride dichlormethane adduct (0.87 g) and the mixture was carbonylated at 50 bar CO pressure at 100° C. for 48 h. The mixture was evaporated and the residue purified by flash chromatography (silica gel, EtOAc/n-heptane, 1:1) to give the title compound (2.79 g, 91%) as a black solid. MS (ESI, m/z): 260.5 [(M+H)$^+$].

b) 1-Cyclopropyl-3,3-dimethyl-2-oxoindoline-6-carboxylic acid

A mixture of methyl 1-cyclopropyl-3,3-dimethyl-2-oxoindoline-6-carboxylate (3.6 g) in MeOH (56 ml) and aqueous sodium hydroxide (1 M, 56 ml) was stirred at 22° C. for 5 h. The mixture was partitioned between water and TBME, the pH of the aqueous layer was adjusted to 1 using aqueous hydrochloric acid (25%), the aqueous layer was extracted with dichloromethane, the organic layer was dried and evaporated to give the title compound (3.33 g, 98%) as a light yellow solid, which was used without further purification. MS (ESI, m/z): 246.5 [(M+H)$^+$].

c) 1-Cyclopropyl-3,3-dimethyl-6-(3-(pyridin-4-yl)-1,2,4-oxadiazol-5-yl)indolin-2-one (Example 4)

A solution of 1-cyclopropyl-3,3-dimethyl-2-oxoindoline-6-carboxylic acid (140 mg) and carbonyldiimidazole (111 mg) in dry THF (6 ml) was heated to reflux temperature for 2 h. 4-pyridylamidoxime (94 mg) was added and stirring was continued at reflux for 1.5 h. The mixture was evaporated, the residue dissolved in acetic acid (6 ml) and heated to reflux temperature for 1.5 h and stirring was continued at 22° C. for 16 h. The mixture was evaporated, the residue partitioned between aqueous sodium carbonate (1 M) and dichloromethane, the organic layer was washed with aqueous sodium carbonate (1 M), dried, evaporated and the residue purified by flash chromatography (silica gel, gradient, 0% to 50% EtOAc in dichloromethane) to give the title compound (189 mg, 96%) as a white solid. MS (ESI, m/z): 347.5 [(M+H)$^+$].

Example 5

1-Cyclopropyl-3,3-dimethyl-6-(5-(pyridin-4-yl)-1,2,4-oxadiazol-3-yl)indolin-2-one

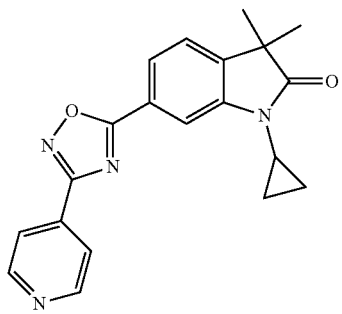 [SMILES: CC1(C)C(=O)N(C2CC2)c2cc(-c3nc(-c4ccncc4)no3)ccc21]

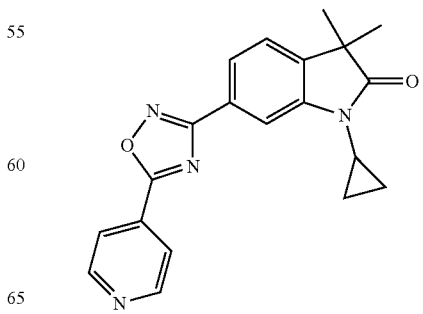

a) 1-Cyclopropyl-3,3-dimethyl-2-oxoindoline-6-carbonitrile

A suspension of 6-bromo-1-cyclopropyl-3,3-dimethylindolin-2-one from example 1b (2.0 g) in DMF (36 ml) was flushed with argon, treated with dicyanozinc (1.04 g) and tetrakis(triphenylphosphine)palladium(0) (825 mg) and stirring was continued at 85° C. for 16 h. The mixture was evaporated, the residue partitioned between aqueous sodium carbonate (1 M) and EtOAc, the organic layer was washed with aqueous sodium carbonate (1 M), dried, evaporated and the residue purified by flash chromatography (silica gel, gradient, 0% to 40% EtOAc in n-heptane) to give the title compound (1.61 g, quant.) as a light yellow solid. MS (ESI, m/z): 227.5 [(M+H)$^+$].

b) (Z)-1-Cyclopropyl-N'-hydroxy-3,3-dimethyl-2-oxoindoline-6-carboximidamide A mixture of 1-cyclopropyl-3,3-dimethyl-2-oxoindoline-6-carbonitrile (170 mg), hydroxylamine hydrochloride (132 mg) and DIPEA (248 mg) in ethanol (1.5 ml) was heated to 70° C. for 4 h and evaporated. The residue was partitioned between aqueous sodium carbonate (1 M) and EtOAc, the organic layer was washed with aqueous sodium carbonate (1 M), dried and evaporated to give the crude title compound (240 mg, ca. 80% pure, 99%) as a light green foam, which was used without further purification. MS (ESI, m/z): 260.5 [(M+H)$^+$].

c) 1-Cyclopropyl-3,3-dimethyl-6-(5-(pyridin-4-yl)-1,2,4-oxadiazol-3-yl)indolin-2-one (Example 5)

A solution of isonicotinic acid (91 mg) and carbonyldiimidazole (130 mg) in dry THF (7.4 ml) was heated to reflux temperature for 1.5 h, (Z)-1-cyclopropyl-N'-hydroxy-3,3-dimethyl-2-oxoindoline-6-carboximidamide (240 mg, 80% pure) was added and heating was continued for 1.5 h. The mixture was evaporated, the residue dissolved in acetic acid (7.4 ml) and heated to reflux temperature for 1 h. The mixture was evaporated, the residue partitioned between aqueous sodium carbonate (1 M) and EtOAc, the organic layer was washed with aqueous sodium carbonate (1 M), dried, evaporated and the residue purified by flash chromatography (silica gel, gradient, 0% to 5% MeOH in dichloromethane) to give the title compound (171 mg, 67%) as a pale yellow solid. MS (ESI, m/z): 347.5 [(M+H)$^+$].

Example 6

3,3-Dimethyl-1-oxetan-3-yl-6-(3-pyridin-4-yl-[1,2,4]oxadiazol-5-yl)-1,3-dihydro-indol-2-one

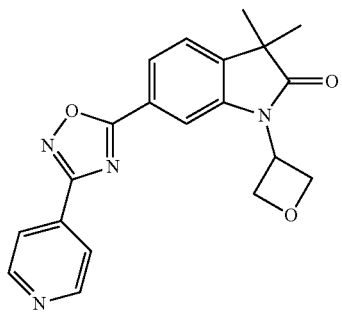 [SMILES: CC1(C)C(=O)N(C2COC2)c2cc(-c3nc(-c4ccncc4)no3)ccc21]

a) 6-Bromo-3,3-dimethyl-1-(oxetan-3-yl)indolin-2-one

A mixture of 6-bromo-3,3-dimethylindolin-2-one from example 1a (500 mg), 3-bromooxetane (594 mg) and cesium carbonate (1.36 g) in DMF (17 ml) was flushed with argon for 5 min and heated to 60° C. for 18 h. The mixture was partitioned between aqueous HCl (1 M) and EtOAc, the organic layer was dried, evaporated and the residue purified by flash chromatography (silica gel, gradient, 0% to 50% EtOAc in n-heptane) to give the title compound (550 mg, 80%) as an orange waxy solid. MS (ESI, m/z): 296.3/298.3 [(M+H)$^+$].

b) Methyl 3,3-dimethyl-1-(oxetan-3-yl)-2-oxoindoline-6-carboxylate

6-Bromo-3,3-dimethyl-1-(oxetan-3-yl)indolin-2-one was converted in analogy to example 4a to give the title compound (97%) as a viscous brown oil. MS (ESI, m/z): 276.5 [(M+H)$^+$].

c) 3,3-Dimethyl-1-(oxetan-3-yl)-2-oxoindoline-6-carboxylic acid

Methyl 3,3-dimethyl-1-(oxetan-3-yl)-2-oxoindoline-6-carboxylate was converted in analogy to example 4b to give the title compound (93%) as an off-white solid. MS (ESI, m/z): 262.5 [(M+H)$^+$].

d) 3,3-Dimethyl-1-oxetan-3-yl-6-(3-pyridin-4-yl-[1,2,4]oxadiazol-5-yl)-1,3-dihydro-indol-2-one (Example 6)

3,3-Dimethyl-1-(oxetan-3-yl)-2-oxoindoline-6-carboxylic acid was converted in analogy to example 4c to give the title compound (52%) as a white solid. MS (ESI, m/z): 363.5 [(M+H)$^+$].

Example 7

1,3,3-Trimethyl-6-(2-(pyridin-3-yl)oxazol-5-yl)indolin-2-one

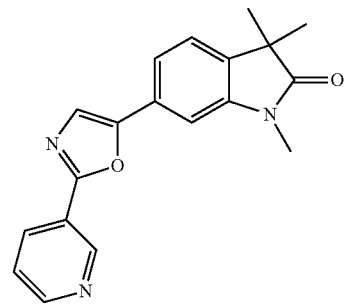 [SMILES: CN1C(=O)C(C)(C)c2ccc(-c3cnc(-c4cccnc4)o3)cc21]

a) 2-Oxo-2-(1,3,3-trimethyl-2-oxoindolin-6-yl)ethanaminium chloride

A suspension of 6-(2-bromoacetyl)-1,3,3-trimethylindolin-2-one from example 3b (400 mg) and hexamethylenetetramine (189 mg) in toluene (10 ml) was heated to 40° C. for 3 h. The mixture was filtered and the residue washed with toluene and diethyl ether. The solid was dissolved in EtOH (10 ml) and hydrochloric acid (25%, 3 ml), stirred at 22° C. for 2 h and evaporated to give the crude title compound (475 mg, quant.) as a yellow solid, which was used without further purification. MS (ESI, m/z): 233.5 [(M+H)$^+$].

b) N-(2-Oxo-2-(1,3,3-trimethyl-2-oxoindolin-6-yl)ethyl)nicotinamide

To a solution of nicotinoyl chloride hydrochloride (237 mg) and 2-oxo-2-(1,3,3-trimethyl-2-oxoindolin-6-yl)ethanaminium chloride (470 mg) in dichloromethane (4 ml) was added at 0° C. DIPEA (740 mg) and stirring was continued at 22° C. for 2 h. The mixture was partitioned between water and EtOAc, the organic layer was dried and evaporated to give the title compound (333 mg, 77%) as an light brown foam, which was used without further purification. MS (ESI, m/z): 338.5 [(M+H)$^+$].

c) 1,3,3-Trimethyl-6-(2-(pyridin-3-yl)oxazol-5-yl)indolin-2-one (Example 7)

A mixture of N-(2-oxo-2-(1,3,3-trimethyl-2-oxoindolin-6-yl)ethyl)nicotinamide (330 mg) and (methoxycarbonylsulfamoyl)triethylammoniumhydroxid (699 mg) in THF (8 ml) was heated in a microwave oven at 100° C. for 20 min. The mixture was evaporated and the residue purified by flash chromatography (silica gel, gradient, 0% to 10% MeOH in dichloromethane) to give the title compound (140 mg, 55%) as light brown foam. MS (ESI, m/z): 320.5 [(M+H)$^+$].

Example 8

1-Cyclopropyl-3,3-dimethyl-6-(2-(pyridin-3-yl)oxazol-5-yl)indolin-2-one

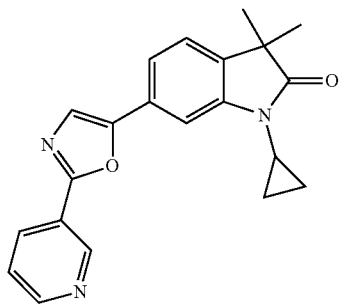 [SMILES: CC1(C)C(=O)N(C2CC2)c2cc(-c3cnc(-c4cccnc4)o3)ccc21]

6-Bromo-1-cyclopropyl-3,3-dimethylindolin-2-one from example 1b was converted in analogy to example 3a-b to 6-(2-bromoacetyl)-1-cyclopropyl-3,3-dimethyl-indolin-2-one, which was converted in analogy to example 7a-c to give the title compound as a light yellow solid. MS (ESI, m/z): 346.5 [(M+H)$^+$].

Example 9

1-Cyclopropyl-3,3-dimethyl-6-(5-(pyridin-3-yl)oxazol-2-yl)indolin-2-one

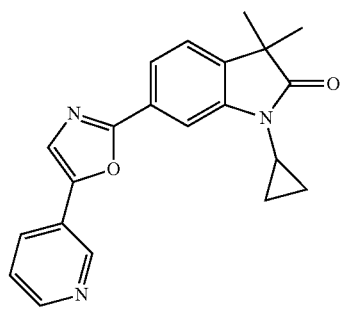 [SMILES: CC1(C)C(=O)N(C2CC2)c2cc(-c3ncc(-c4cccnc4)o3)ccc21]

a) 1-Cyclopropyl-N-(2,2-dimethoxy-2-(pyridin-3-yl)ethyl)-3,3-dimethyl-2-oxoindoline-6-carboxamide A solution of 1-cyclopropyl-3,3-dimethyl-2-oxoindoline-6-carboxylic acid (150 mg) from example 4b, thionyl chloride (109 mg) and DMF (9 mg) in toluene (2 ml) was heated to 110° C. for 3 h. The mixture was evaporated, the residue diluted with dichloromethane (2 ml), treated at 22° C. with 2,2-dimethoxy-2-(pyridin-3-yl)ethanamine dihydrochloride (203 mg, prepared according to Bouchet et al., WO 2000002875), which was followed by the addition of DIPEA (592 mg) and stirring was continued for 22° C. The reaction mixture was partitioned between aqueous sodium carbonate and dichloromethane, the organic layer was dried and evaporated to give the crude title compound (260 mg, quant.) as a viscous oil, which was used without further purification. MS (ESI, m/z): 410.6 [(M+H)$^+$].

b) 1-Cyclopropyl-3,3-dimethyl-2-oxo-N-(2-oxo-2-(pyridin-3-yl)ethyl)indoline-6-carboxamide A solution of 1-cyclopropyl-N-(2,2-dimethoxy-2-(pyridin-3-yl)ethyl)-3,3-dimethyl-2-oxoindoline-6-carboxamide (260 mg) in hydrochloric acid (37%, 5 ml) was stirred at 22° C. for 2 h. The mixture was partitioned between aqueous sodium carbonate solution and EtOAc, the organic layer was dried, evaporated and the residue purified by flash chromatography (silica gel, gradient, 0% to 7% MeOH in dichloromethane) to give the title compound (110 mg, 48%) as white foam. MS (ESI, m/z): 364.6 [(M+H)$^+$].

c) 1-Cyclopropyl-3,3-dimethyl-6-(5-(pyridin-3-yl)oxazol-2-yl)indolin-2-one (Example 9)

A mixture of 1-cyclopropyl-3,3-dimethyl-2-oxo-N-(2-oxo-2-(pyridin-3-yl)ethyl)indoline-6-carboxamide (110 mg) and (methoxycarbonylsulfamoyl)triethylammoniumhydroxid (216 mg) in THF (3 ml) was heated in a microwave oven at 100° C. for 20 min. The mixture was evaporated and the residue purified by flash chromatography (silica gel, gradient, 0% to 10% MeOH in dichloromethane) to give the title compound (55 mg, 53%) as light yellow solid. MS (ESI, m/z): 346.5 [(M+H)$^+$].

Example 10

1-Cyclopropyl-3,3-dimethyl-6-(2-(pyridin-4-yl)oxazol-5-yl)indolin-2-one

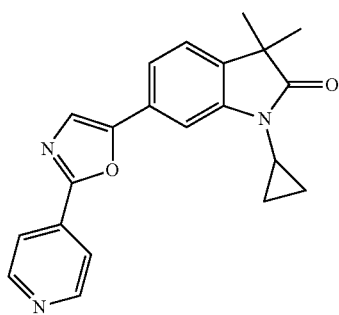 [SMILES: CC1(C)C(=O)N(C2CC2)c2cc(-c3cnc(-c4ccncc4)o3)ccc21]

Example 10 was prepared in analogy to example 8 using pyridine-4-carbonyl chloride to give the title compound as a yellow viscous oil. MS (ESI, m/z): 346.5 [(M+H)$^+$].

Example 11

3,3-Dimethyl-1-(oxetan-3-yl)-6-(5-(pyridin-4-yl)-1,3,4-oxadiazol-2-yl)indolin-2-one

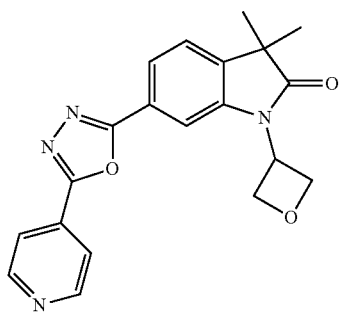 [SMILES: CC1(C)C(=O)N(C2COC2)c2cc(-c3nnc(-c4ccncc4)o3)ccc21]

a) N'-Isonicotinoyl-3,3-dimethyl-1-(oxetan-3-yl)-2-oxoindoline-6-carbohydrazide

To a solution of 3,3-dimethyl-1-(oxetan-3-yl)-2-oxoindoline-6-carboxylic acid (170 mg) from example 6c, 1H-benzo[d][1,2,3]triazol-1-ol (141 mg), N1-((ethylimino)methylene)-N3,N3-dimethylpropane-1,3-diamine hydrochloride (200 mg) and triethylamine (165 mg) in dichloromethane (10 ml) was added isonicotinohydrazide (125 mg) and stirring was continued at 22° C. for 19 h. The mixture was evaporated and the residue purified by flash chromatography (silica gel, gradient, 0% to 15% MeOH in dichloromethane with 1% NH3) to give the title compound (150 mg, 59%) as a white solid. MS (ESI, m/z): 381.5 [(M+H)$^+$].

b) 3,3-Dimethyl-1-(oxetan-3-yl)-6-(5-(pyridin-4-yl)-1,3,4-oxadiazol-2-yl)indolin-2-one (Example 11)

To a solution of N'-isonicotinoyl-3,3-dimethyl-1-(oxetan-3-yl)-2-oxoindoline-6-carbohydrazide (150 mg) and p-toluensulfonyl chloride (142 mg) in acetonitrile (6 ml) was added triethylamine (150 mg) and stirring was continued at 22° C. for 4 h. The mixture was partitioned between aqueous sodium hydrogencarbonate solution and EtOAc, the organic layer was dried, evaporated and the residue purified by flash chromatography (silica gel, gradient, 0% to 100% EtOAc in n-heptane) to give the title compound (141 mg, 97%) as white solid. MS (ESI, m/z): 363.5 [(M+H)$^+$].

Example 12

1-Cyclopropyl-3,3-dimethyl-6-(2-(2-methylpyridin-4-yl)oxazol-5-yl)indolin-2-one

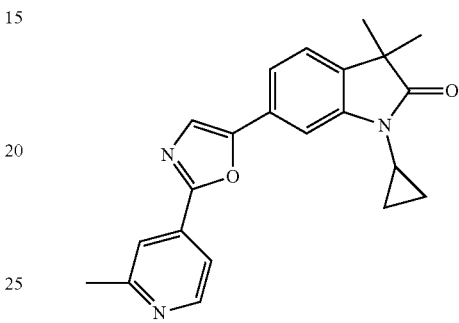

Example 12 was prepared in analogy to example 10 using 2-methylpyridine-4-carbonyl chloride to give the title compound as a light yellow foam. MS (ESI, m/z): 360.5 [(M+H)$^+$].

Example 13

1,3,3-Trimethyl-6-(5-(pyridin-4-yl)-1,3,4-oxadiazol-2-yl)indolin-2-one

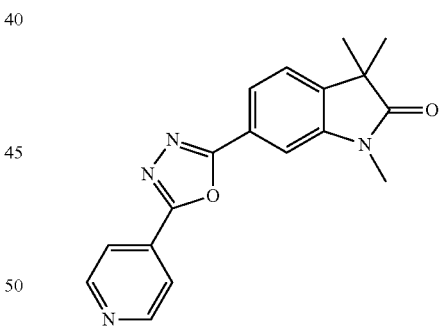

a) 1,3,3-Trimethyl-2-oxoindoline-6-carboxylic acid

To a suspension of NaH (12.6 g) in THF (260 ml) was added at 22° C. methyl 2-oxoindoline-6-carboxylate (15.0 g) over 30 min, which was followed by the addition of MeI (44.5 g) using a syringe-pump over 80 min keeping the temperature between 24-28° C. and stirring was continued for 2.5 h. A solution of NaOH (6.3 g) in water (20 ml) was added and stirring was continued for 1 h. The mixture was partitioned between water and TBME, the pH of the aqueous layer was adjusted to 1, the suspension was filtered and the residue dried to give the title compound (16.0 g, 93%) as a brown solid.

b) N'-Isonicotinoyl-1,3,3-trimethyl-2-oxoindoline-6-carbohydrazide 1,3,3-Trimethyl-2-oxoindoline-6-carboxylic acid was converted in analogy to example 11a to give the title compound (93%) as a light yellow foam. MS (ESI, m/z): 339.5 [(M+H)⁺].

c) 1,3,3-Trimethyl-6-(5-(pyridin-4-yl)-1,3,4-oxadiazol-2-yl)indolin-2-one (Example 13)

N'-Isonicotinoyl-1,3,3-trimethyl-2-oxoindoline-6-carbohydrazide was converted in analogy to example 11b to give the title compound (84%) as an off-white solid. MS (ESI, m/z): 321.5 [(M+H)⁺].

Example 14

1-Cyclopropyl-3,3-dimethyl-6-(2-(2-methylpyridin-4-yl)thiazol-5-yl)indolin-2-one

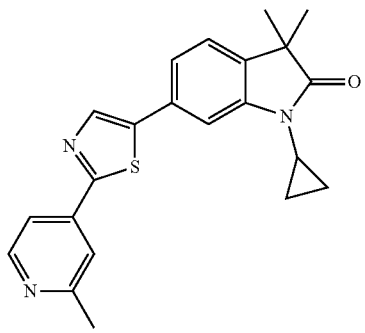 [SMILES: Cc1cc(-c2ncc(-c3ccc4c(c3)N(C3CC3)C(=O)C4(C)C)s2)ccn1]

a) 2-(2-Methylpyridin-4-yl)thiazole

Argon was bubbled through a mixture of 2-methylpyridin-4-ylboronic acid (614 mg), 2-bromothiazole (736 mg) and aqueous sodium carbonate (2 M, 4.5 ml) in dioxane (8 ml), which was followed by the addition of tetrakis(triphenylphosphine)palladium(0) (259 mg) and the mixture was heated to 90° C. for 16 h. The reaction mixture was filtered through dicalite, the filtrate was partitioned between water and EtOAc, the organic layer was dried, evaporated and the residue purified by flash chromatography (silica gel, gradient, 30% to 50% EtOAc in n-heptane) to give the title compound (325 mg, 41%) as light brown solid. MS (ESI, m/z): 177.5 [(M+H)⁺].

b) 1-Cyclopropyl-3,3-dimethyl-6-(2-(2-methylpyridin-4-yl)thiazol-5-yl)indolin-2-one (Example 14)

A mixture of 6-bromo-1-cyclopropyl-3,3-dimethylindolin-2-one (220 mg), 2-(2-methylpyridin-4-yl)thiazole (152 mg), triphenylphosphine (21 mg), 1,1'-bis(diphenylphosphino)ferrocene-palladium(II)dichloride dichlormethane adduct (32 mg), and silver carbonate (433 mg), in water (5 ml) was heated to 90° C. for 4 d. The reaction mixture was filtered over dicalite, the filtrate was partitioned between brine and dichloromethane, the organic layer was dried, evaporated and the residue purified by flash chromatography (silica gel, gradient, 40% to 60% EtOAc in n-heptane). The compound containing fraction was evaporated, the residue partitioned between aqueous hydrochloric acid and EtOAc, the pH of the aqueous layer was adjusted to 9 using aqueous sodium hydroxide and the aqueous layer was extracted with dichloromethane. The organic layer was dried and evaporated to give the title compound (126 mg, 43%) as a yellow viscous oil. MS (ESI, m/z): 376.6 [(M+H)⁺].

Example 15

1-Cyclopropyl-3,3-dimethyl-6-(4-(pyridin-3-yl)oxazol-2-yl)indolin-2-one

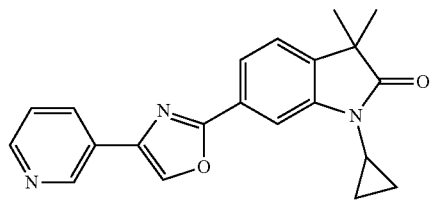 [SMILES: CC1(C)C(=O)N(C2CC2)c2cc(-c3nc(-c4cccnc4)co3)ccc21]

a) 1-Cyclopropyl-3,3-dimethyl-2-oxoindoline-6-carboxamide

To a suspension of 1-cyclopropyl-3,3-dimethyl-2-oxoindoline-6-carboxylic acid (1.2 g) from example 4b in toluene (11 ml) was added thionyl chloride (698 mg) and DMF (36 mg) and stirring was continued at reflux temperature for 2 h. The mixture was evaporated, the residue dissolved in dichloromethane (27 ml), aqueous ammonia (25%, 18 ml) was added and the mixture was vigorously stirred at 22° C. for 2 d. The mixture was partitioned between aqueous sodium carbonate (1 M) and dichloromethane, the organic layer was dried and evaporated to give the title compound (1.17 g, 98%) as a white solid, which was used without further purification. MS (ESI, m/z): 245.5 [(M+H)⁺].

b) N-(2-Chloroacetyl)-1-cyclopropyl-3,3-dimethyl-2-oxoindoline-6-carboxamide

A suspension of 1-cyclopropyl-3,3-dimethyl-2-oxoindoline-6-carboxamide (1.17 g) and chloroacetyl chloride (2.76 g) was heated to 110° C. for 1 h. The mixture was purified by flash chromatography (silica gel, gradient, 0% to 100% EtOAc in n-heptane) to give the title compound (1.18 g, 77%) as a white solid. MS (ESI, m/z): 321.5 [(M+H)⁺].

c) 2-(1-Cyclopropyl-3,3-dimethyl-2-oxoindolin-6-yl)oxazol-4-yl trifluoromethanesulfonate To a suspension of sodium hydride (174 mg) in 1,4-dioxane (30 ml) was added at 22° C. a solution of N-(2-chloroacetyl)-1-cyclopropyl-3,3-dimethyl-2-oxoindoline-6-carboxamide (1.16 g) in 1,4-dioxane (30 ml) and stirring was continued at reflux temperature for 0.5 h and at 22° C. for 1 h. The mixture was filtered, the filtrate evaporated and the residue dissolved in dichloromethane (15 ml). To the solution was added at −78° C. triethylamine (732 mg) followed by triflic anhydride (1.53 g) and stirring was continued at 22° C. for 30 min. The mixture was partitioned between saturated sodium hydrogencarbonate and dichloromethane, the organic layer was dried, evaporated and the residue purified by flash chromatography (silica gel, gradient, 0% to 100% EtOAc in n-heptane) to give the title compound (600 mg, 40%) as a white solid. MS (ESI, m/z): 417.5 [(M+H)+].

d) 1-Cyclopropyl-3,3-dimethyl-6-(4-(pyridin-3-yl)oxazol-2-yl)indolin-2-one (Example 15)

A mixture of 2-(1-cyclopropyl-3,3-dimethyl-2-oxoindolin-6-yl)oxazol-4-yl trifluoromethanesulfonate (200 mg), pyridin-3-ylboronic acid (65 mg) and aqueous sodium carbonate (1 M, 0.7 ml) in 1,4-dioxane (7 ml) was degassed with argon, bis(triphenylphosphine)palladium(II)chloride (17 mg) was added and the mixture heated in a microwave oven to 150° C. for 20 min. The mixture was filtered over dicalite, the filtrate evaporated and the residue purified by flash chromatography (silica gel, gradient, 0% to 100% EtOAc in n-heptane) followed by preparative HPLC purification (RP-18, gradient, acetonitrile/water) to give the title compound (98 mg, 54%) as a white solid. MS (ESI, m/z): 346.6 [(M+H)+].

Example 16

1-Cyclopropyl-3,3-dimethyl-6-(4-(pyridin-4-yl)oxazol-2-yl)indolin-2-one

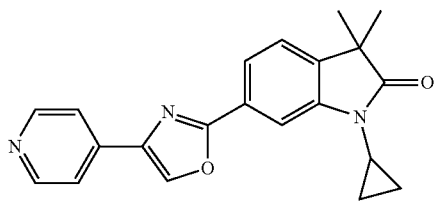 [SMILES: CC1(C)C(=O)N(C2CC2)c2cc(-c3nc(-c4ccncc4)co3)ccc21]

Example 16 was prepared in analogy to example 15 using pyridin-4-ylboronic acid to give the title compound as a white solid. MS (ESI, m/z): 346.5 [(M+H)+].

Example 17

1-Cyclopropyl-3,3-dimethyl-6-(4-(2-methylpyridin-4-yl)oxazol-2-yl)indolin-2-one

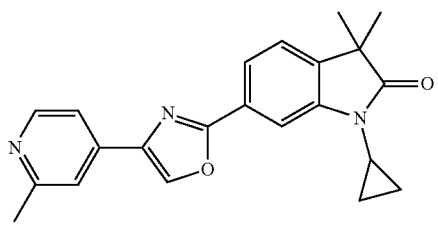 [SMILES: Cc1cc(-c2coc(-c3ccc4c(c3)N(C3CC3)C(=O)C4(C)C)n2)ccn1]

Example 17 was prepared in analogy to example 15 using 2-methylpyridin-4-ylboronic acid to give the title compound as a white solid. MS (ESI, m/z): 360.6 [(M+H)+].

Example 18

1,3,3-Trimethyl-6-(2-(2-methylpyridin-4-yl)thiazol-5-yl)indolin-2-one

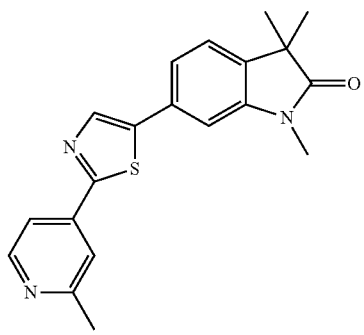

Example 18 was prepared in analogy to example 14 starting from 6-bromo-1,3,3-trimethylindolin-2-one from example 2a to give the title compound as a yellow foam. MS (ESI, m/z): 350.5 [(M+H)+].

Example 19

1-Cyclopropyl-3,3-dimethyl-6-(5-(2-methylpyridin-4-yl)oxazol-2-yl)indolin-2-one

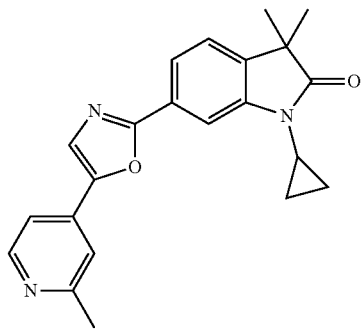 [SMILES: Cc1cc(-c2cnc(-c3ccc4c(c3)N(C3CC3)C(=O)C4(C)C)o2)ccn1]

Example 19 was prepared in analogy to example 9 using 2,2-dimethoxy-2-(2-methylpyridin-4-yl)ethanamine to give the title compound as a light yellow solid. MS (ESI, m/z): 360.6 [(M+H)+].

Example 20

1,3,3-Trimethyl-6-(4-(pyridin-4-yl)-1H-imidazol-1-yl)indolin-2-one

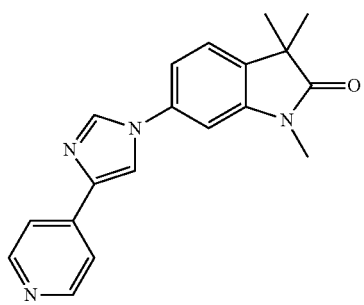 [SMILES: CN1C(=O)C(C)(C)c2ccc(-n3cnc(-c4ccncc4)c3)cc21]

A suspension of 6-bromo-1,3,3-trimethylindolin-2-one from example 2a (110 mg), 4-(1H-imidazol-4-yl)pyridine hydrochloride (79 mg, prepared according to Ganellin et al., J. Med. Chem. 38, 3342, 1995), potassium carbonate (188 mg) and 2-acetylcyclohexanon (30 mg) in N-methylpyrrolidone (1.0 ml) was flushed with argon during 5 min, then copper(I)chloride (9 mg) was added and the mixture heated at 130° C. for 36 h. The mixture was partitioned between saturated sodium hydrogencarbonate and EtOAc, the organic layer was dried, evaporated and the residue purified by flash chromatography (silica gel, gradient, 0% to 15% MeOH in dichloromethane). The compound containing fraction was evaporated and the residue triturated with diethyl ether and dried to give the title compound (100 mg, 73%) as an off-white solid. MS (ESI, m/z): 319.2 [(M+H)+].

Example 21

1,3,3-Trimethyl-6-(4-(pyridin-3-yl)oxazol-2-yl)indolin-2-one

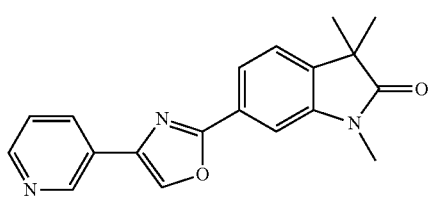 [SMILES: CN1C(=O)C(C)(C)c2ccc(-c3nc(-c4cccnc4)co3)cc21]

Example 21 was prepared in analogy to example 15 starting from 1,3,3-trimethyl-2-oxoindoline-6-carboxylic acid from example 13a to give the title compound as a white solid. MS (ESI, m/z): 320.6 [(M+H)+].

Example 22

1,3,3-Trimethyl-6-(2-(2-methylpyridin-4-yl)oxazol-5-yl)indolin-2-one

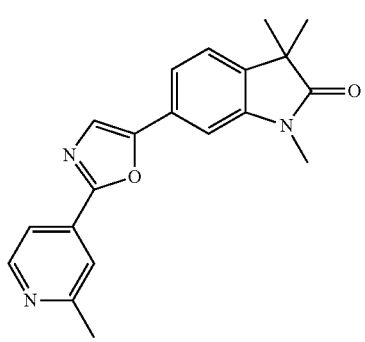 [SMILES: Cc1cc(-c2ncc(-c3ccc4c(c3)N(C)C(=O)C4(C)C)o2)ccn1]

a) 2-(2-Methylpyridin-4-yl)oxazole

To a solution of oxazole (201 mg) in THF (3 ml) was added at −78° C. BuLi (1.6 M in hexane, 2.2 ml), which was followed by the addition of zinc chloride (2 M in 2-methyltetrahydrofuran, 2.9 ml) and stirring was continued at 22° C. for 30 min. 4-Bromo-2-methylpyridine (0.50 g) and tetrakis(triphenylphosphine)palladium(0) (336 mg) were added and stirring was continued at 60° C. for 5 h. The mixture was partitioned between water and EtOAc, the organic layer was dried, evaporated and the residue purified by flash chromatography (silica gel, gradient, 40% to 60% EtOAc in n-heptane) to give the title compound (295 mg, 63%) as a yellow solid. MS (ESI, m/z): 161.5 [(M+H)+].

b) 1,3,3-Trimethyl-6-(2-(2-methylpyridin-4-yl)oxazol-5-yl)indolin-2-one (Example 22)

6-Bromo-1,3,3-trimethylindolin-2-one from example 2a was reacted with 2-(2-methylpyridin-4-yl)oxazole in analogy to example 14b to give the title compound as an off-white foam. MS (ESI, m/z): 334.5 [(M+H)+].

Example 23

3,3-Dimethyl-1-(oxetan-3-yl)-6-(2-(pyridin-3-yl)oxazol-5-yl)indolin-2-one

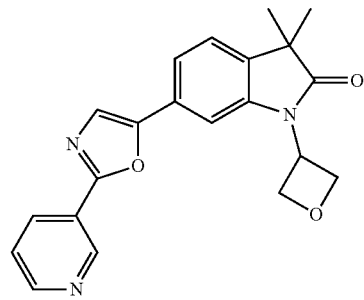 [SMILES: CC1(C)C(=O)N(C2COC2)c2cc(-c3cnc(-c4cccnc4)o3)ccc21]

a) 2-(Pyridin-3-yl)oxazole

Oxazole was coupled with 3-bromopyridine in analogy to example 22a to give the title compound (53%) as a light yellow solid. MS (ESI, m/z): 147.2 [(M+H)+].

b) 3,3-Dimethyl-1-(oxetan-3-yl)-6-(2-(pyridin-3-yl)oxazol-5-yl)indolin-2-one (Example 23)

6-Bromo-3,3-dimethyl-1-(oxetan-3-yl)indolin-2-one from example 6a was reacted with 2-(pyridin-3-yl)oxazole in analogy to example 14b to give the title compound (31%) as a white foam. MS (ESI, m/z): 362.6 [(M+H)+].

Example 24

3,3-Dimethyl-6-(2-(6-methylpyridin-3-yl)oxazol-5-yl)-1-(oxetan-3-yl)indolin-2-one

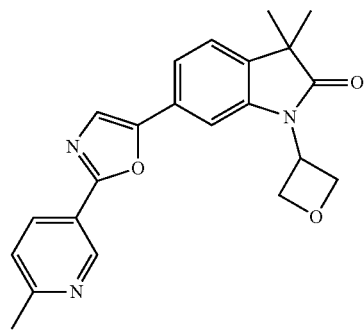 [SMILES: Cc1ccc(-c2ncc(-c3ccc4c(c3)N(C3COC3)C(=O)C4(C)C)o2)cn1]

a) 2-(6-Methylpyridin-3-yl)oxazole

Oxazole was coupled with 5-bromo-2-methylpyridine in analogy to example 22a to give the title compound (59%) as a light yellow solid. MS (ESI, m/z): 161.5 [(M+H)⁺].

b) 3,3-Dimethyl-6-(2-(6-methylpyridin-3-yl)oxazol-5-yl)-1-(oxetan-3-yl)indolin-2-one (Example 24)

6-Bromo-3,3-dimethyl-1-(oxetan-3-yl)indolin-2-one from example 6a was reacted with 2-(6-methylpyridin-3-yl)oxazole in analogy to example 14b to give the title compound (24%) as a white solid. MS (ESI, m/z): 376.5 [(M+H)⁺].

Example 25

3,3-Dimethyl-6-(2-(pyridin-3-yl)oxazol-5-yl)indolin-2-one

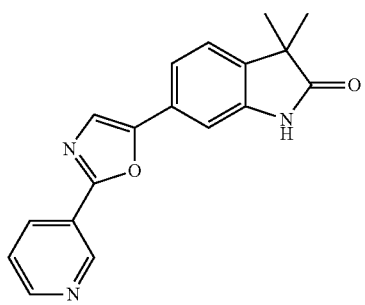 [SMILES: CC1(C)C(=O)Nc2cc(-c3cnc(-c4cccnc4)o3)ccc21]

a) 6-Bromo-1-(4-methoxybenzyl)-3,3-dimethylindolin-2-one

A mixture of 6-bromo-3,3-dimethylindolin-2-one from example 1a (250 mg) in DMF (8 ml) was flushed with argon. 1-(Bromomethyl)-4-methoxybenzene (209 mg) and cesium carbonate (679 mg) were added and stirring was continued at 80° C. for 1 h. The mixture was partitioned between water and EtOAc, the organic layer was dried, evaporated and the residue purified by flash chromatography (silica gel, gradient, 0% to 50% EtOAc in n-heptane) to give the title compound (340 mg, 91%) as a red liquid. MS (ESI, m/z): 360.0/362.5 [(M+H)⁺].

b) 1-(4-Methoxybenzyl)-3,3-dimethyl-6-(2-(pyridin-3-yl)oxazol-5-yl)indolin-2-one 6-Bromo-1-(4-methoxybenzyl)-3,3-dimethylindolin-2-one was reacted with 2-(pyridin-3-yl)oxazole from example 23a in analogy to example 14b to give the title compound (58%) as a yellow solid. MS (ESI, m/z): 426.7 [(M+H)⁺].

c) 3,3-Dimethyl-6-(2-(pyridin-3-yl)oxazol-5-yl)indolin-2-one (Example 25)

A solution of 1-(4-methoxybenzyl)-3,3-dimethyl-6-(2-(pyridin-3-yl)oxazol-5-yl)indolin-2-one (112 mg) in TFA (1 ml) was heated to 110° C. for 2 d. The mixture was partitioned between aqueous sodium carbonate (2 M) and EtOAc, the organic layer was dried, evaporated and the residue purified by flash chromatography (silica gel, gradient, 50% to 80% EtOAc in n-heptane). The compound containing fraction was evaporated, the residue partitioned between aqueous hydrochloric acid and EtOAc, the pH of the aqueous layer was adjusted to 9 using aqueous sodium hydroxide and the aqueous layer was extracted with dichloromethane. The organic layer was dried and evaporated to give the title compound (42 mg, 52%) as an off-white solid. MS (ESI, m/z): 306.5 [(M+H)⁺].

Example 26

3,3-Dimethyl-6-(2-(2-methylpyridin-4-yl)oxazol-5-yl)-1-(oxetan-3-yl)indolin-2-one

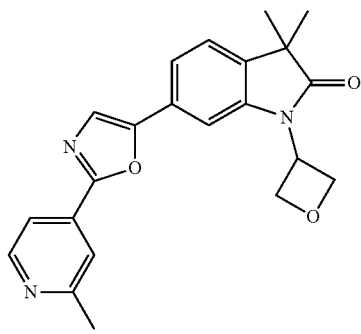 [SMILES: Cc1cc(-c2ncc(-c3ccc4c(c3)N(C3COC3)C(=O)C4(C)C)o2)ccn1]

6-Bromo-3,3-dimethyl-1-(oxetan-3-yl)indolin-2-one from example 6a was reacted with 2-(2-methylpyridin-4-yl)oxazole from example 22a in analogy to example 14b to give the title compound (30%) as a yellow foam. MS (ESI, m/z): 376.6 [(M+H)⁺].

Example 27

3,3-Dimethyl-6-(2-(6-methylpyridin-3-yl)oxazol-5-yl)indolin-2-one

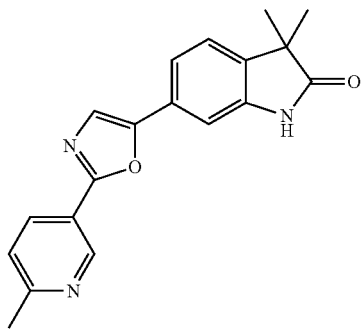 [SMILES: Cc1ccc(-c2ncc(-c3ccc4c(c3)NC(=O)C4(C)C)o2)cn1]

Example 27 was prepared in analogy to example 25 using 2-(6-methylpyridin-3-yl)oxazole from example 24a to give the title compound as a brown solid. MS (ESI, m/z): 320.6 [(M+H)⁺].

Example 28

1-(2-Hydroxyethyl)-3,3-dimethyl-6-(5-(pyridin-4-yl)-1,3,4-oxadiazol-2-yl)indolin-2-one

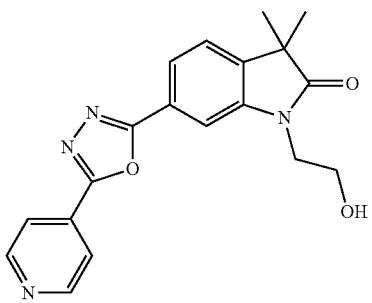 [SMILES: CC1(C)C(=O)N(CCO)c2cc(-c3nnc(-c4ccncc4)o3)ccc21]

a) 3,3-Dimethyl-2-oxoindoline-6-carboxylic acid

To a solution of methyl 2-oxoindoline-6-carboxylate (17.6 g) in DMF (260 ml) was added MeI (26.1 g) followed by NaH (3.68 g) keeping the temperature at 22° C. After 30 min a second portion of NaH (1.84 g) was added followed after 1 h by a third portion (1.84 g) and stirring was continued at 22° C. for 16 h. Water (7 ml) followed by sodium hydroxide (34.5 g) were added and stirring was continued at 45° C. for 1 h and at 22° C. for 16 h. The mixture was partitioned between TBME and water, the pH of the aqueous layer was adjusted to 3 using aqueous hydrochloric acid (25%) and extracted with dichloromethane. The organic layer was dried and evaporated to give the crude title compound (17.9 g, 95%) as a red solid, which was used without further purification. MS (ESI, m/z): 204.2 [(M−H)⁻].

b) 3,3-Dimethyl-6-(5-(pyridin-4-yl)-1,3,4-oxadiazol-2-yl)indolin-2-one 3,3-Dimethyl-2-oxoindoline-6-carboxylic acid was converted to the title compound (36%) in analogy to example 11a-b, obtained as an orange solid. MS (ESI, m/z): 307.6 [(M+H)⁺].

c) 1-(2-(Tert-butyldimethylsilyloxy)ethyl)-3,3-dimethyl-6-(5-(pyridin-4-yl)-1,3,4-oxadiazol-2-yl)indolin-2-one A mixture of 3,3-dimethyl-6-(5-(pyridin-4-yl)-1,3,4-oxadiazol-2-yl)indolin-2-one (171 mg) in DMF (2.5 ml) was flushed with argon, then treated with (2-bromoethoxy)(tert-butyl)dimethylsilane (267 mg) and cesium carbonate (364 mg) and stirring was continued at 80° C. for 16 h. The mixture was partitioned between water and EtOAc, the organic layer was dried, evaporated and the residue purified by flash chromatography (silica gel, gradient, 0% to 20% MeOH/NH4OH in dichloromethane) to give the impure title compound (307 mg) as a brown solid, which was further used without further purification. MS (ESI, m/z): 465.7 [(M+H)⁺].

d) 1-(2-Hydroxyethyl)-3,3-dimethyl-6-(5-(pyridin-4-yl)-1,3,4-oxadiazol-2-yl)indolin-2-one (Example 28)

To a solution of 1-(2-(tert-butyldimethylsilyloxy)ethyl)-3,3-dimethyl-6-(5-(pyridin-4-yl)-1,3,4-oxadiazol-2-yl)indolin-2-one (307 mg) in THF (13 ml) was added at 0° C. TBAF (136 mg) and stirring was continued at 0° C. for 10 min and at 22° C. for 3 h. The mixture was partitioned between water and EtOAc, the organic layer was dried, evaporated and the residue purified by flash chromatography (silica gel, gradient, 0% to 20% MeOH/NH4OH in dichloromethane) to give the title compound (137 mg, 75%) as a light yellow solid. MS (ESI, m/z): 351.6 [(M+H)⁺].

Example 29

1,3,3-Trimethyl-6-(4-(pyridin-3-yl)-1H-imidazol-1-yl)indolin-2-one

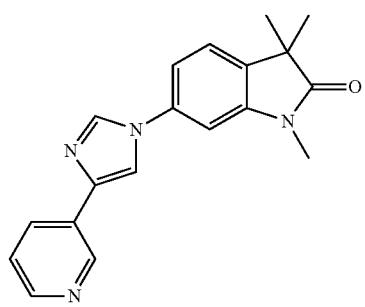 [SMILES: CN1C(=O)C(C)(C)c2ccc(-n3cnc(-c4cccnc4)c3)cc21]

Example 29 was prepared in analogy to example 20 using 3-(1H-imidazol-4-yl)pyridine (prepared according to Denton et al., J. Med. Chem., 48, 224, 2005) to give the title compound (38%) as a light yellow solid. MS (ESI, m/z): 319.6 [(M+H)⁺].

Example 30

3,3-Dimethyl-1-(oxetan-3-yl)-6-(4-(pyridin-3-yl)-1H-imidazol-1-yl)indolin-2-one

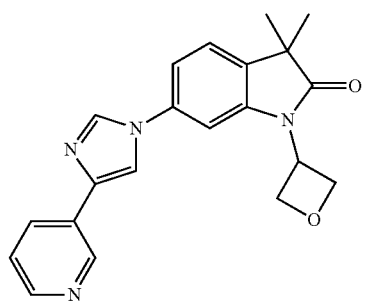 [SMILES: CC1(C)C(=O)N(C2COC2)c2cc(-n3cnc(-c4cccnc4)c3)ccc21]

Example 30 was prepared in analogy to example 20 using 6-bromo-3,3-dimethyl-1-(oxetan-3-yl)indolin-2-one from example 6a and 3-(1H-imidazol-4-yl)pyridine (prepared according to Denton et al., J. Med. Chem., 48, 224, 2005) to give the title compound (36%) as a white solid. MS (ESI, m/z): 361.6 [(M+H)⁺].

Example 31

1,3,3-Trimethyl-6-(4-methyl-2-(pyridin-3-yl)oxazol-5-yl)indolin-2-one

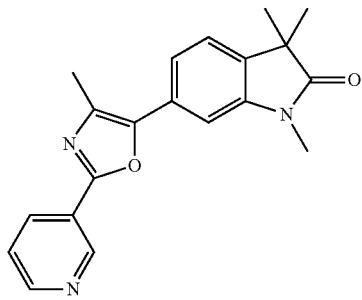 [SMILES: Cc1nc(-c2cccnc2)oc1-c1ccc2c(c1)N(C)C(=O)C2(C)C]

6-Bromo-1,3,3-trimethylindolin-2-one from example 2a was reacted with 4-methyl-2-(pyridin-3-yl)oxazole (prepared according to Dondoni et al., Synthesis (8), 693-6, 1987) in analogy to example 14b to give the title compound (57%) as a white solid. MS (ESI, m/z): 334.6 [(M+H)$^+$].

Example 32

3,3-Dimethyl-6-(4-(pyridin-3-yl)-1H-imidazol-1-yl)indolin-2-one

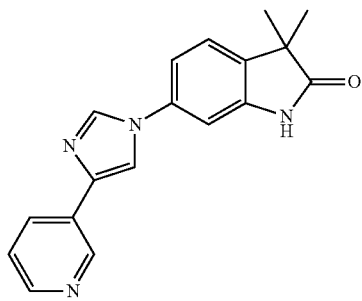 [SMILES: CC1(C)C(=O)Nc2cc(-n3cnc(-c4cccnc4)c3)ccc21]

Example 32 was prepared in analogy to example 20 using 6-Bromo-3,3-dimethyl-indolin-2-one from example 1a and 3-(1H-imidazol-4-yl)pyridine (prepared according to Denton et al., J. Med. Chem., 48, 224, 2005) to give the title compound (22%) as a white solid. MS (ESI, m/z): 305.5 [(M+H)$^+$].

Example 33

1-Cyclopropyl-3,3-dimethyl-6-(2-(6-methylpyridin-3-yl)oxazol-5-yl)indolin-2-one

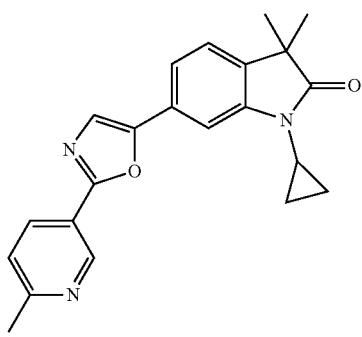 [SMILES: Cc1ccc(-c2ncc(-c3ccc4c(c3)N(C3CC3)C(=O)C4(C)C)o2)cn1]

Example 33 was prepared in analogy to example 27 using 6-bromo-1-cyclopropyl-3,3-dimethylindolin-2-one from example 1b to give the title compound as a white foam. MS (ESI, m/z): 360.6 [(M+H)$^+$].

Example 34

3,3-Dimethyl-1-(oxetan-3-yl)-6-(4-(pyridin-4-yl)-1H-imidazol-1-yl)indolin-2-one

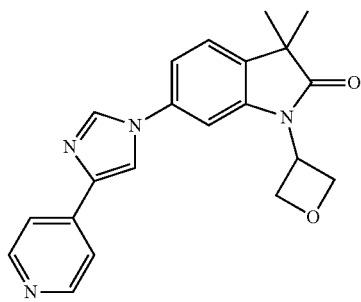 [SMILES: CC1(C)C(=O)N(C2COC2)c2cc(-n3cnc(-c4ccncc4)c3)ccc21]

Example 34 was prepared in analogy to example 20 using 6-bromo-3,3-dimethyl-1-(oxetan-3-yl)indolin-2-one from example 6a to give the title compound as a white solid. MS (ESI, m/z): 361.6 [(M+H)$^+$].

Example 35

3,3-Dimethyl-6-(2-(2-methylpyridin-4-yl)oxazol-5-yl)indolin-2-one

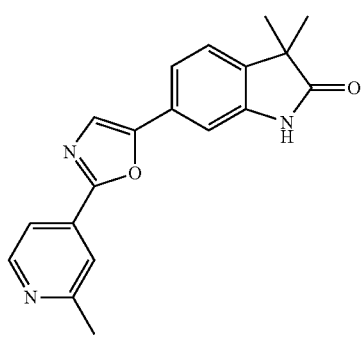 [SMILES: Cc1cc(-c2ncc(-c3ccc4c(c3)NC(=O)C4(C)C)o2)ccn1]

Example 35 was prepared in analogy to example 22 using 6-bromo-3,3-dimethyl-indolin-2-one from example 1a to give the title compound as a light yellow solid. MS (ESI, m/z): 320.5 [(M+H)$^+$].

Example 36

1,3,3-Trimethyl-6-(4-methyl-2-(6-methylpyridin-3-yl)oxazol-5-yl)indolin-2-one

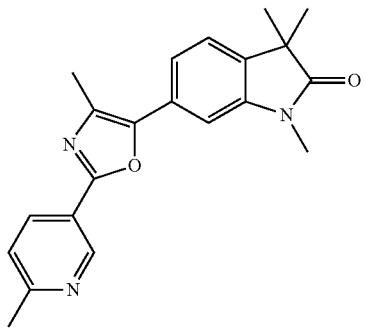 [SMILES: Cc1ccc(-c2nc(C)c(-c3ccc4c(c3)N(C)C(=O)C4(C)C)o2)cn1]

a) 4-Methyl-2-(6-methylpyridin-3-yl)oxazole

To a solution of 4-methyloxazole (254 mg) in THF (2 ml) was added at −78° C. a solution of n-BuLi (1.6 M in THF, 2.3 ml) followed by zinc chloride (2 M in 2-methyl-tetrahydrofuran, 2.3 ml) and stirring was continued at 22° C. for 30 min. 5-Bromo-2-methylpyridine (526 mg) and tetrakis(triphenylphosphine)palladium(0) (353 mg) were added and stirring was continued at 60° C. for 2 h. The mixture was partitioned between water and EtOAc, the organic layer was dried, evaporated and the residue purified by flash chromatography (silica gel, gradient, 20% to 70% EtOAc in n-heptane) to give the title compound (283 mg, 53%) as a light yellow solid. MS (ESI, m/z): 175.5 [(M+H)+].

b) 1,3,3-Trimethyl-6-(4-methyl-2-(6-methylpyridin-3-yl)oxazol-5-yl)indolin-2-one (Example 36)

6-Bromo-1,3,3-trimethylindolin-2-one from example 2a was reacted with 4-methyl-2-(6-methylpyridin-3-yl)oxazole in analogy to example 14b to give the title compound (57%) as a white solid. MS (ESI, m/z): 334.6 [(M+H)+].

Example 37

1-Cyclopropyl-3,3-dimethyl-6-(4-methyl-2-(6-methylpyridin-3-yl)oxazol-5-yl)indolin-2-one

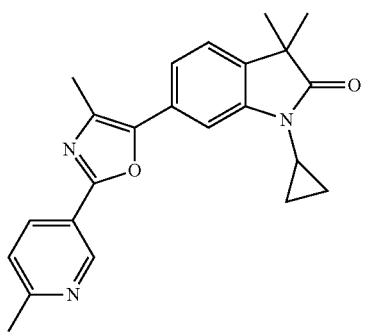 [SMILES: Cc1ccc(-c2nc(C)c(-c3ccc4c(c3)N(C3CC3)C(=O)C4(C)C)o2)cn1]

6-Bromo-1-cyclopropyl-3,3-dimethylindolin-2-one from example 1b was reacted with 4-methyl-2-(6-methylpyridin-3-yl)oxazole from example 36a in analogy to example 14b to give the title compound (37%) as an off-white foam. MS (ESI, m/z): 374.6 [(M+H)+].

Example 38

1,3,3-Trimethyl-6-(4-methyl-2-(2-methylpyridin-4-yl)oxazol-5-yl)indolin-2-one

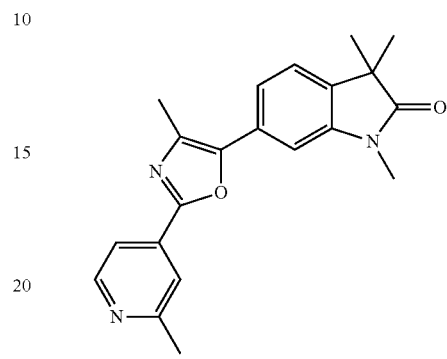

a) 4-Methyl-2-(2-methylpyridin-4-yl)oxazole

To a solution of 4-methyloxazole (254 mg) in THF (2 ml) was added at −78° C. n-BuLi (1.6 M in THF, 2.3 ml) and zinc chloride (2 M in 2-methyl-tetrahydrofuran, 2.3 ml) and stirring was continued at 22° C. for 30 min. 4-Bromo-2-methylpyridine (526 mg) and tetrakis(triphenylphosphine)palladium(0) (353 mg) were added and stirring was continued at 60° C. for 2 h. The mixture was partitioned between water and EtOAc, the organic layer was dried, evaporated and the residue purified by flash chromatography (silica gel, gradient, 30% to 70% EtOAc in n-heptane) to give the title compound (375 mg, 70%) as a light yellow viscous oil. MS (ESI, m/z): 175.5 [(M+H)+].

b) 1,3,3-Trimethyl-6-(4-methyl-2-(2-methylpyridin-4-yl)oxazol-5-yl)indolin-2-one (Example 38)

6-Bromo-1,3,3-trimethylindolin-2-one from example 2a was reacted with 4-methyl-2-(2-methylpyridin-4-yl)oxazole in analogy to example 14b to give the title compound (70%) as a light yellow foam. MS (ESI, m/z): 348.6 [(M+H)+].

Example 39

1-Cyclopropyl-3,3-dimethyl-6-(4-methyl-2-(2-methylpyridin-4-yl)oxazol-5-yl)indolin-2-one

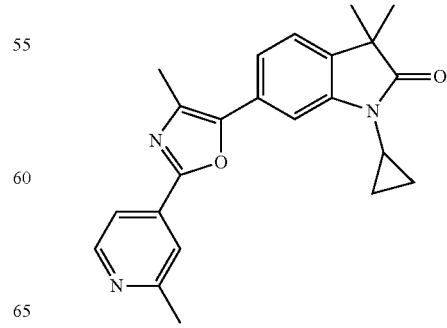

6-Bromo-1-cyclopropyl-3,3-dimethylindolin-2-one from example 1b was reacted with 4-methyl-2-(2-methylpyridin-4-yl)oxazole from example 38a in analogy to example 14b to give the title compound (61%) as a light yellow foam. MS (ESI, m/z): 374.6 [(M+H)$^+$].

Example 40

1,3,3-Trimethyl-6-(4-(pyridin-4-yl)-1H-pyrazol-1-yl)indolin-2-one

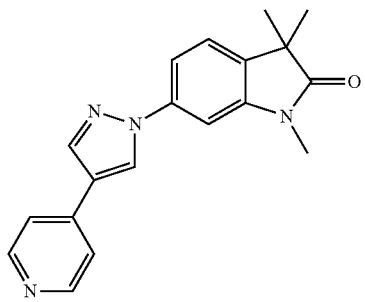 [SMILES: CN1C(=O)C(C)(C)c2ccc(-n3cc(-c4ccncc4)cn3)cc21]

A suspension of 6-bromo-1,3,3-trimethylindolin-2-one (140 mg) from example 2a, 4-(1H-pyrazol-4-yl)pyridine (80 mg, prepared according to Bauer et al., J. Med. Chem. 11, 981, 1968) and potassium carbonate (190 mg) in dry DMSO (4 ml) was flushed with argon. Copper(I)iodide (11 mg) and L-proline (25 mg) were added and stirring was continued at 110° C. for 16 h. The reaction mixture was partitioned between water and dichloromethane, the organic layer was dried, evaporated and the residue purified by flash chromatography (silica gel, gradient, 0% to 10% MeOH/NH4OH in dichloromethane) to give the title compound (74 mg, 42%) as a white solid. MS (ESI, m/z): 319.4 [(M+H)$^+$].

Example 41

1,3,3-Trimethyl-6-(4-(pyridin-3-yl)-1H-pyrazol-1-yl)indolin-2-one

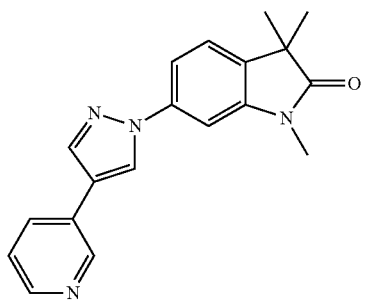 [SMILES: CN1C(=O)C(C)(C)c2ccc(-n3cc(-c4cccnc4)cn3)cc21]

a) 3-(1H-Pyrazol-4-yl)pyridine

To a suspension of 3-bromopyridine (400 mg) and tert-butyl 4-(4,4,5,5-tetramethyl-1,3,2-dioxaborolan-2-yl)-1H-pyrazole-1-carboxylate (745 mg) in 1,4-dioxane (12 ml) was added aqueous sodium carbonate (1 M, 2.5 ml) and the mixture was flushed with argon for 5 min. [1,1'-Bis(diphenylphosphino)ferrocene]dichloropalladium(II) (103 mg) was added and stirring was continued at 110° C. for 16 h. The mixture was partitioned between aqueous sodium hydrogencarbonate and EtOAc, the organic layer was dried, evaporated and the residue purified by flash chromatography (silica gel, gradient, 0% to 10% MeOH/NH4OH in dichloromethane) to give the title compound (234 mg, 64%) as a light brown solid. MS (ESI, m/z): 146.2 [(M+H)$^+$].

b) 1,3,3-Trimethyl-6-(4-(pyridin-3-yl)-1H-pyrazol-1-yl)indolin-2-one (Example 41)

6-Bromo-1,3,3-trimethylindolin-2-one from example 2a was reacted with 3-(1H-pyrazol-4-yl)pyridine in analogy to example 40 to give the title compound (38%) as a white solid. MS (ESI, m/z): 319.4 [(M+H)$^+$].

Example 42

1,3,3-Trimethyl-6-(3-pyridin-4-yl-isoxazol-5-yl)-1,3-dihydro-indol-2-one

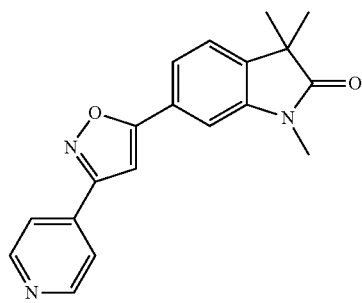 [SMILES: CN1C(=O)C(C)(C)c2ccc(-c3cc(-c4ccncc4)no3)cc21]

a) 1-(Pyridin-4-yl)-3-(1,3,3-trimethyl-2-oxoindolin-6-yl)propane-1,3-dione

To a solution of 6-acetyl-1,3,3-trimethylindolin-2-one (1.22 g) from example 3a and methyl isonicotinate (770 mg) in dry THF (30 ml) was added at 22° C. sodium hydride (515 mg) and stirring was continued for 6 h. The mixture was evaporated and the residue partitioned between water and EtOAc, the organic layer was dried, evaporated and the residue triturated with n-pentane to give the title compound (700 mg, 39%) as an orange solid. MS (ESI, m/z): 321.4 [(M−H)$^-$].

b) 1,3,3-Trimethyl-6-(3-pyridin-4-yl-isoxazol-5-yl)-1,3-dihydro-indol-2-one (Example 42)

To a solution of 1-(pyridin-4-yl)-3-(1,3,3-trimethyl-2-oxoindolin-6-yl)propane-1,3-dione (300 mg) in dry ethanol (6 ml) was added hydroxylamine hydrochloride (65 mg) and stirring was continued at reflux temperature for 16 h. The mixture was evaporated and the residue partitioned between aqueous sodium hydrogencarbonate and EtOAc, the organic layer was dried, evaporated and the residue purified by supercritical fluid chromatography (Princeton, 4-ethylpyridine 20×250 mm 100 A, Sum, 12% isopropanol/88% carbondioxide, 60 ml/min, 40° C.) to give the title compound (141 mg, 47%) as the slower eluting isomer as a white solid. MS (ESI, m/z): 320.4 [(M+H)$^+$].

The faster eluting regio isomer, 1,3,3-trimethyl-6-(5-pyridin-4-yl-isoxazol-3-yl)-1,3-dihydro-indol-2-one (85 mg, 29%), was obtained as a white solid. MS (ESI, m/z): 320.4 [(M+H)+].

Example 43

3,3-Dimethyl-1-(oxetan-3-yl)-6-(4-(pyridin-3-yl)-1H-pyrazol-1-yl)indolin-2-one

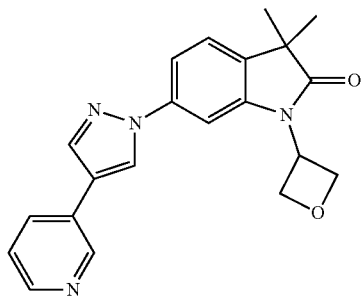 [SMILES: CC1(C)C(=O)N(C2COC2)c2cc(-n3cc(-c4cccnc4)cn3)ccc21]

6-Bromo-3,3-dimethyl-1-(oxetan-3-yl)indolin-2-one from example 6a was converted in analogy to example 41 to the title compound (42%), obtained as a white solid. MS (ESI, m/z): 361.4 [(M+H)+].

Example 44

1,3,3-Trimethyl-6-(2-(pyridin-3-yl)oxazol-4-yl)indolin-2-one

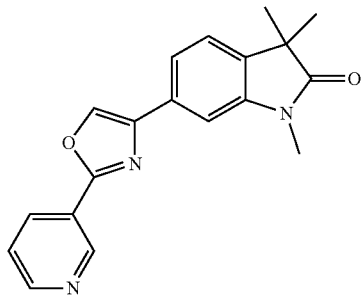 [SMILES: CN1C(=O)C(C)(C)c2ccc(-c3coc(-c4cccnc4)n3)cc21]

a) 1,3,3-Trimethyl-6-(oxazol-4-yl)indolin-2-one

A suspension of 6-(2-bromoacetyl)-1,3,3-trimethylindolin-2-one (1.05 g) from example 3b and formamide (14.4 g) was heated to 110° C. for 2 h. The mixture was partitioned between saturated aqueous sodium hydrogencarbonate and EtOAc, the organic layer was dried, evaporated and the residue purified by flash chromatography (silica gel, gradient, 0% to 50% EtOAc in n-heptane) to give the title compound (335 mg, 39%) as a white solid. MS (ESI, m/z): 243.6 [(M+H)+].

b) 6-(2-Chlorooxazol-4-yl)-1,3,3-trimethylindolin-2-one

To a solution of 1,3,3-trimethyl-6-(oxazol-4-yl)indolin-2-one (0.23 g) in dry THF (4 ml) was added at −78° C. a solution of LiHMDS (1 M in THF, 1.0 ml) and the mixture was allowed to warm to 22° C. The mixture was cooled to −78° C. and treated with hexachloroethane (238 mg) and stirring was continued at 22° C. for 3 h. The mixture was partitioned between saturated aqueous ammonium chloride and TBME, the organic layer was dried, evaporated and the residue purified by flash chromatography (silica gel, gradient, 0% to 50% EtOAc in n-heptane) to give the title compound (195 mg, 74%) as a white solid. MS (ESI, m/z): 277.5 [(M+H)+].

c) 1,3,3-Trimethyl-6-(2-(pyridin-3-yl)oxazol-4-yl)indolin-2-one (Example 44)

A mixture of 6-(2-chlorooxazol-4-yl)-1,3,3-trimethylindolin-2-one (100 mg) and pyridine-3-boronic acid (58 mg) in 1,4-dioxane (3 ml) and aqueous sodium carbonate (2 M, 0.7 ml) was flushed with argon, bis(triphenylphosphine)palladium(II)dichloride was added (26 mg) and the mixture was heated to reflux temperature for 2 h. The mixture was evaporated and the residue purified by flash chromatography (silica gel, gradient, 0% to 100% EtOAc in n-heptane) followed by HPLC purification (RP-18, gradient, acetonitrile/water) to give the title compound (68 mg, 59%) as a white solid. MS (ESI, m/z): 320.5 [(M+H)+].

Example 45

3,3-Dimethyl-1-(oxetan-3-yl)-6-(4-(pyridin-4-yl)-1H-pyrazol-1-yl)indolin-2-one

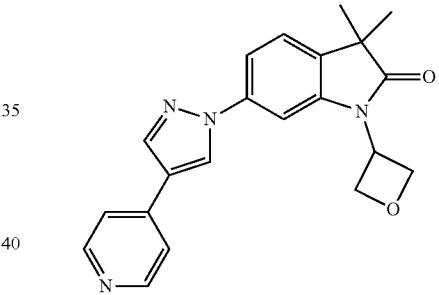

6-Bromo-3,3-dimethyl-1-(oxetan-3-yl)indolin-2-one from example 6a was converted to the title compound (20%) in analogy to example 40, obtained as a white solid. MS (ESI, m/z): 361.5 [(M+H)+].

Example 46

1,3,3-Trimethyl-6-(1-(pyridin-4-yl)-1H-pyrazol-4-yl)indolin-2-one

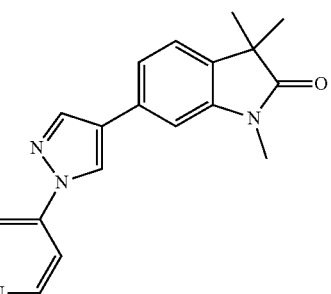

a) 1,3,3-Trimethyl-6-(1H-pyrazol-4-yl)indolin-2-one

A mixture of 6-bromo-1,3,3-trimethylindolin-2-one (200 mg) from example 2a and tert-butyl 4-(4,4,5,5-tetramethyl-1,3,2-dioxaborolan-2-yl)-1H-pyrazole-1-carboxylate (232 mg) in 1,4-dioxane (4.5 ml) and aqueous sodium carbonate (2 M, 0.8 ml) was flushed with argon, [1,1'-bis(diphenylphosphino)ferrocene]dichloropalladium(II) (32 mg) was added and stirring was continued in a microwave oven at 120° C. for 30 min. The mixture was partitioned between saturated aqueous sodium hydrogencarboante and EtOAc, the organic layer was dried, evaporated and the residue purified by flash chromatography (silica gel, gradient, 0% to 100% EtOAc in n-heptane) to give the title compound (115 mg, 61%) as a brown viscous oil. MS (ESI, m/z): 242.5 [(M+H)$^+$].

b) 1,3,3-Trimethyl-6-(1-(pyridin-4-yl)-1H-pyrazol-4-yl)indolin-2-one (Example 46)

A suspension of 1,3,3-trimethyl-6-(1H-pyrazol-4-yl)indolin-2-one (85 mg), 4-bromopyridine hydrochloride (103 mg) and potassium carbonate (166 mg) in dry DMSO (2.5 ml) was flushed with argon, then copper(I)iodide (14 mg) and L-proline (32 mg) were added and stirring was continued at 110° C. for 16 h. The mixture was partitioned between water and EtOAc, the organic layer was dried, evaporated and the residue purified by flash chromatography (silica gel, gradient, 0% to 5% MeOH in dichloromethane), which was followed by a second flash chromatography (silica gel, gradient, 0% to 100% EtOAc in n-heptane) to give the title compound (86 mg, 77%) as a white solid. MS (ESI, m/z): 319.5 [(M+H)$^+$].

Example 47

3,3-Dimethyl-6-(4-(pyridin-4-yl)-1H-imidazol-1-yl)indolin-2-one

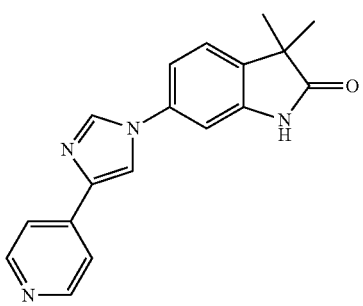 [SMILES: CC1(C)C(=O)Nc2cc(-n3cnc(-c4ccncc4)c3)ccc21]

Example 47 was prepared in analogy to example 20 using 6-bromo-3,3-dimethyl-indolin-2-one from example 1a to give the title compound (15%) as a white solid. MS (ESI, m/z): 305.5 [(M+H)$^+$].

Example 48

1-Cyclopropyl-3,3-dimethyl-6-(4-(pyridin-3-yl)-1H-imidazol-1-yl)indolin-2-one

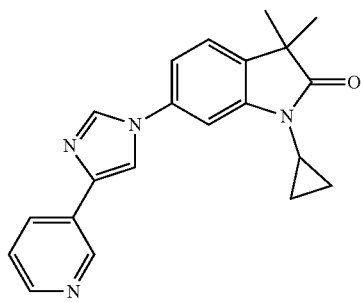 [SMILES: CC1(C)C(=O)N(C2CC2)c2cc(-n3cnc(-c4cccnc4)c3)ccc21]

Example 48 was prepared in analogy to example 32 using 6-bromo-1-cyclopropyl-3,3-dimethylindolin-2-one from example 1b to give the title compound (30%) as a white solid. MS (ESI, m/z): 345.6 [(M+H)$^+$].

Example 49

3,3-Dimethyl-6-(5-(2-methylpyridin-4-yl)-1,3,4-oxadiazol-2-yl)-1-(oxetan-3-yl)indolin-2-one

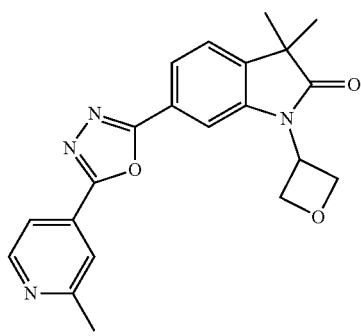 [SMILES: Cc1cc(-c2nnc(-c3ccc4c(c3)N(C3COC3)C(=O)C4(C)C)o2)ccn1]

Example 49 was prepared in analogy to example 11 using 2-methylisonicotinohydrazide to give the title compound (47%) as a white solid. MS (ESI, m/z): 377.6 [(M+H)$^+$].

Example 50

1,3,3-Trimethyl-6-(1-(pyridin-3-yl)-1H-pyrazol-4-yl)indolin-2-one

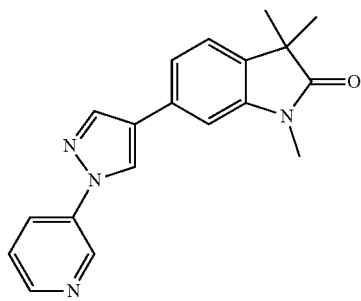 [SMILES: CN1C(=O)C(C)(C)c2ccc(-c3cnn(-c4cccnc4)c3)cc21]

Example 50 was prepared in analogy to example 46 using 3-bromopyridine to give the title compound (52%) as a white solid. MS (ESI, m/z): 319.6 [(M+H)$^+$].

Example 51

3,3-Dimethyl-6-(4-(pyridin-3-yl)-1H-pyrazol-1-yl)indolin-2-one

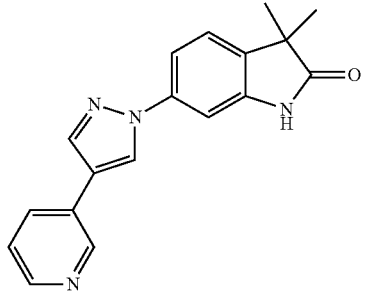 [SMILES: CC1(C)C(=O)Nc2cc(-n3cc(-c4cccnc4)cn3)ccc21]

Example 51 was prepared in analogy to example 40 using 6-bromo-3,3-dimethylindolin-2-one from example 1a and 3-(1H-pyrazol-4-yl)pyridine from example 41a to give the title compound (52%) as a white foam. MS (ESI, m/z): 305.6 [(M+H)$^+$].

Example 52

1-Cyclopropyl-3,3-dimethyl-6-(4-(pyridin-3-yl)-1H-pyrazol-1-yl)indolin-2-one

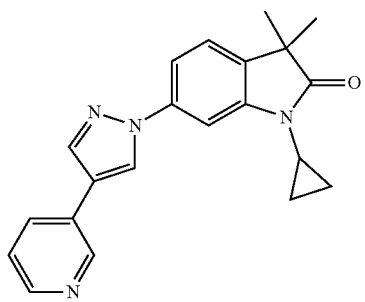 [SMILES: CC1(C)C(=O)N(C2CC2)c2cc(-n3cc(-c4cccnc4)cn3)ccc21]

Example 52 was prepared in analogy to example 40 using 6-bromo-1-cyclopropyl-3,3-dimethylindolin-2-one from example 1b and 3-(1H-pyrazol-4-yl)pyridine from example 41a to give the title compound (34%) as a white foam. MS (ESI, m/z): 345.5 [(M+H)$^+$].

Example 53

1-Cyclopropyl-3,3-dimethyl-6-(4-(pyridin-4-yl)-1H-imidazol-1-yl)indolin-2-one

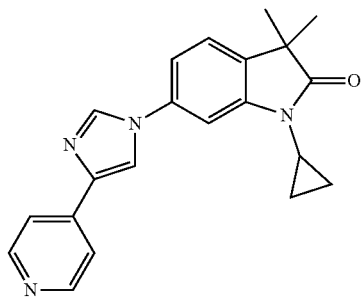 [SMILES: CC1(C)C(=O)N(C2CC2)c2cc(-n3cnc(-c4ccncc4)c3)ccc21]

Example 53 was prepared in analogy to example 20 using 6-bromo-1-cyclopropyl-3,3-dimethylindolin-2-one from example 1b to give the title compound (11%) as a white solid. MS (ESI, m/z): 345.5 [(M+H)$^+$].

Example 54

1,3,3-Trimethyl-6-(4-(2-methylpyridin-4-yl)-1H-pyrazol-1-yl)indolin-2-one

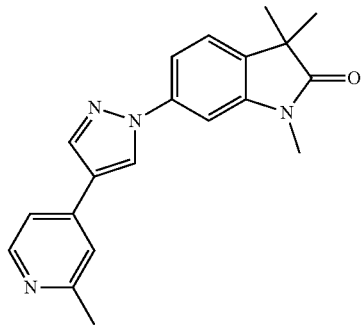 [SMILES: Cc1cc(-c2cnn(-c3ccc4c(c3)N(C)C(=O)C4(C)C)c2)ccn1]

a) 2-Methyl-4-(1H-pyrazol-4-yl)pyridine

The title compound (64%), prepared in analogy to example 41a using 4-bromo-2-methylpyridine, was obtained as a light yellow solid. MS (ESI, m/z): 160.3 [(M+H)$^+$].

b) 1,3,3-Trimethyl-6-(4-(2-methylpyridin-4-yl)-1H-pyrazol-1-yl)indolin-2-one (Example 54)

Example 54 was prepared in analogy to example 40 using 6-bromo-1,3,3-trimethylindolin-2-one from example 2a and 2-methyl-4-(1H-pyrazol-4-yl)pyridine to give the title compound (25%) as a white solid. MS (ESI, m/z): 333.5 [(M+H)$^+$].

Example 55

1-Cyclopropyl-3,3-dimethyl-6-(4-(2-methylpyridin-4-yl)-1H-pyrazol-1-yl)indolin-2-one

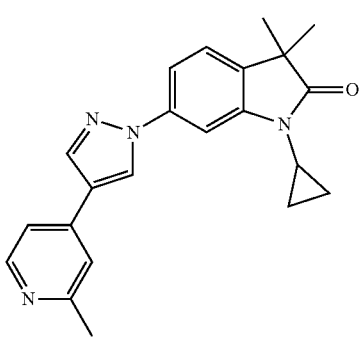 [SMILES: Cc1cc(-c2cnn(-c3ccc4c(c3)N(C3CC3)C(=O)C4(C)C)c2)ccn1]

Example 55 was prepared in analogy to example 40 using 6-bromo-1-cyclopropyl-3,3-dimethylindolin-2-one from example 1b and 2-methyl-4-(1H-pyrazol-4-yl)pyridine from example 54a to give the title compound (29%) as a white solid. MS (ESI, m/z): 359.5 [(M+H)$^+$].

Example 56

1,3,3-Trimethyl-6-(5-(pyridin-4-yl)-1H-pyrazol-3-yl)indolin-2-one

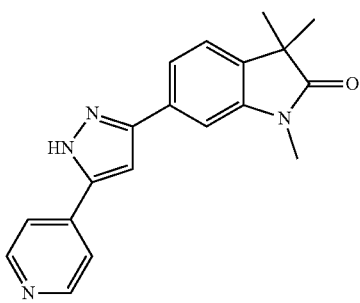 [SMILES: CN1C(=O)C(C)(C)c2ccc(-c3cc(-c4ccncc4)[nH]n3)cc21]

To a solution of 1-(pyridin-4-yl)-3-(1,3,3-trimethyl-2-oxoindolin-6-yl)propane-1,3-dione (170 mg) from example 42a in dry ethanol (3.5 ml) was added DIPEA (82 mg) and hydrazine (1 M in THF, 0.6 ml) and stirring was continued at reflux temperature for 18 h. The reaction mixture was evaporated and the residue purified by flash chromatography (silica gel, gradient, 0% to 20% MeOH/NH4OH in dichloromethane) followed by a second purification by preparative HPLC chromatography (RP-18, gradient, acetonitrile/water) to give the title compound (25 mg, 15%) as a light yellow solid. MS (ESI, m/z): 319.6 [(M+H)$^+$].

Example 57

1,3,3-Trimethyl-6-(4-(pyridin-4-yl)-1H-1,2,3-triazol-1-yl)indolin-2-one

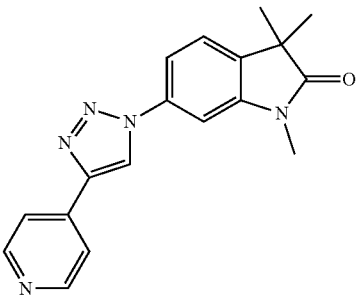 [SMILES: CN1C(=O)C(C)(C)c2ccc(-n3cc(-c4ccncc4)nn3)cc21]

a) 6-Azido-1,3,3-trimethylindolin-2-one

A suspension of 6-bromo-1,3,3-trimethylindolin-2-one (500 mg) from example 2a, sodium azide (258 mg), L(+)-ascorbic acid sodium salt (20 mg) and trans-(1R,2R)—N,N'-bismethyl-1,2-cyclohexanediamine (42 mg) in ethanol (3 ml) and water (1 ml) was flushed with argon. Copper(I) iodide (38 mg) was added and stirring was continued at reflux temperature for 1 h. The mixture was evaporated and the residue purified by flash chromatography (silica gel, gradient, 0% to 40% EtOAc in n-heptane) to give the title compound (366 mg, 86%) as a light brown solid. MS (ESI, m/z): 217.5 [(M+H)$^+$].

b) 1,3,3-Trimethyl-6-(4-(pyridin-4-yl)-1H-1,2,3-triazol-1-yl)indolin-2-one (Example 57)

To a solution of 6-azido-1,3,3-trimethylindolin-2-one (100 mg) and 4-ethinylpyridine (54 mg) in t-BuOH (3 ml) was added L(+)-ascorbic acid sodium salt (46 mg) and copper(II) sulfate pentahydrate (12 mg) in water (3 ml) and stirring was continued at 22° C. for 16 h. The mixture was partitioned between aqueous sodium carbonate (1 M) and EtOAc, the organic layer was dried, evaporated and the residue purified by flash chromatography (silica gel, gradient, 0% to 7% MeOH in dichloromethane) to give the title compound (133 mg, 90%) as a white solid. MS (ESI, m/z): 320.2 [(M+H)$^+$].

Example 58

3,3-Dimethyl-6-(4-(2-methylpyridin-4-yl)-1H-pyrazol-1-yl)indolin-2-one

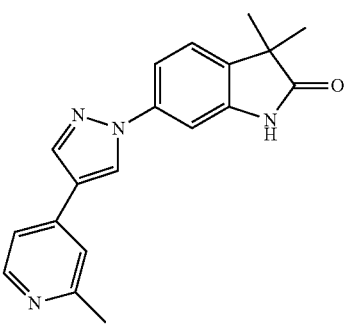 [SMILES: Cc1cc(-c2cnn(-c3ccc4c(c3)NC(=O)C4(C)C)c2)ccn1]

Example 58 was prepared in analogy to example 40 using 6-bromo-3,3-dimethylindolin-2-one from example 1a and 2-methyl-4-(1H-pyrazol-4-yl)pyridine from example 54a to give the title compound (16%) as a light brown solid. MS (ESI, m/z): 319.5 [(M+H)+].

Example 59

1,3,3-Trimethyl-6-(1-(pyridin-3-yl)-1H-imidazol-4-yl)indolin-2-one

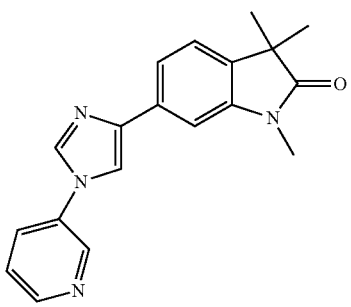 [SMILES: CN1C(=O)C(C)(C)c2ccc(-c3cn(-c4cccnc4)cn3)cc21]

a) 6-(Hydroxymethyl)-1,3,3-trimethylindolin-2-one

To a suspension of 1,3,3-trimethyl-2-oxoindoline-6-carboxylic acid (150 mg) from example 13a in THF (1 ml) was added at 0° C. borane tetrahydrofuran complex (1 M in THF, 1 ml) and stirring was continued at 22° C. for 2 h. The mixture was partitioned between aqueous sodium hydrogencarbonate and EtOAc, the organic layer was washed with water, dried and evaporated to give the crude title compound (140 mg, quant.) as a light yellow foam, which was used without further purification. MS (ESI, m/z): 206.5 [(M+H)+].

b) 1,3,3-Trimethyl-2-oxoindoline-6-carbaldehyde

A suspension of 6-(hydroxymethyl)-1,3,3-trimethylindolin-2-one (2.07 g) and manganese dioxide (6.1 g) in dichloromethane (30 ml) was heated to reflux 1 h and stirring was continued at 22° C. 16 h. The suspension was filtered and the filtrate evaporated to give the crude title compound (1.85 g, 90%) as an orange solid, which was used without further purification. MS (ESI, m/z): 204.5 [(M+H)+].

c) 1,3,3-Trimethyl-6-(oxazol-5-yl)indolin-2-one

A suspension of 1,3,3-trimethyl-2-oxoindoline-6-carbaldehyde (1.68 g), potassium carbonate (1.16 g) and tosylmethylisocyanide (1.61 g) in MeOH (12 ml) was heated to 80° C. for 16 h. The mixture was partitioned between water and dichloromethane, the organic layer was washed with water, dried and evaporated to give the crude title compound (1.96 g, 98%) as a light brown solid, which was used without further purification. MS (ESI, m/z): 243.5 [(M+H)+].

d) 6-(1H-Imidazol-5-yl)-1,3,3-trimethylindolin-2-one

A solution of 1,3,3-trimethyl-6-(oxazol-5-yl)indolin-2-one (700 mg) in formamide (24 ml) was heated to 190° C. for 7 h. The mixture was partitioned between water and EtOAc, the organic layer was washed with water, dried, evaporated and the residue purified by flash chromatography (silica gel, gradient, 0% to 10% MeOH in dichloromethane) to give the title compound (390 mg, 56%) as a brown foam. MS (ESI, m/z): 242.5 [(M+H)+].

e) 1,3,3-Trimethyl-6-(1-(pyridin-3-yl)-1H-imidazol-4-yl)indolin-2-one (Example 59)

A suspension of 6-(1H-imidazol-5-yl)-1,3,3-trimethylindolin-2-one (210 mg), 3-bromopyridine (165 mg), potassium carbonate (361 mg) and 2-acetylcyclohexanone (61 mg) in DMSO (4 ml) was flushed with argon, then copper (I)chloride (22 mg) was added and stirring was continued at 130° C. for 16 h. The mixture was partitioned between water and EtOAc, the organic layer were washed with water, dried, evaporated and the residue purified by flash chromatography (silica gel, gradient, 0% to 10% MeOH in dichloromethane) to give the title compound (189 mg, 68%) as a light yellow foam. MS (ESI, m/z): 319.5 [(M+H)+].

Example 60

1,3,3-Trimethyl-6-(1-(pyridin-4-yl)-1H-imidazol-4-yl)indolin-2-one

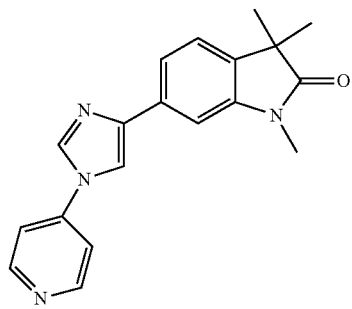 [SMILES: CN1C(=O)C(C)(C)c2ccc(-c3cn(-c4ccncc4)cn3)cc21]

Example 60 was prepared in analogy to example 59 using 4-bromopyridine in step e to give the title compound (60%) as a light brown solid. MS (ESI, m/z): 319.5 [(M+H)+].

Example 61

1,3,3-Trimethyl-6-(5-(2-methylpyridin-4-yl)-1H-pyrazol-3-yl)indolin-2-one

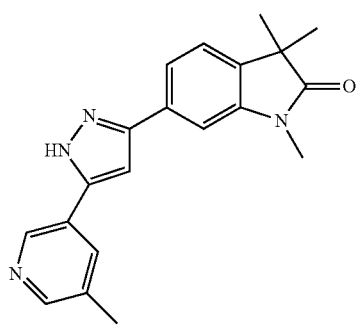 [SMILES: Cc1cncc(-c2cc(-c3ccc4c(c3)N(C)C(=O)C4(C)C)n[nH]2)c1]

a) 1-(2-Methylpyridin-4-yl)-3-(1,3,3-trimethyl-2-oxoindolin-6-yl)propane-1,3-dione 6-Acetyl-1,3,3-trimethylindolin-2-one from example 3a and methyl 2-methylisonicotinate were reacted in analogy to example 42a to give the title compound (47%) as an orange gum. MS (ESI, m/z): 337.5 [(M+H)+].

b) 1,3,3-Trimethyl-6-(5-(2-methylpyridin-4-yl)-1H-pyrazol-3-yl)indolin-2-one (Example 61)

Example 61 was prepared from 1-(2-methylpyridin-4-yl)-3-(1,3,3-trimethyl-2-oxoindolin-6-yl)propane-1,3-dione in analogy to example 56 to give the title compound (57%) as a white solid. MS (ESI, m/z): 333.6 [(M+H)+].

Example 62

1,3,3-Trimethyl-6-(1-(2-methylpyridin-4-yl)-1H-imidazol-4-yl)indolin-2-one

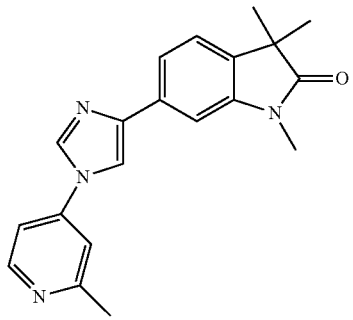 [SMILES: Cc1cc(-n2cnc(-c3ccc4c(c3)N(C)C(=O)C4(C)C)c2)ccn1]

Example 62 was prepared in analogy to example 59 using 4-bromo-2-methylpyridine in step e to give the title compound (81%) as a light brown foam. MS (ESI, m/z): 333.5 [(M+H)+].

Example 63

6-(2-(3-Methoxypyridin-4-yl)oxazol-5-yl)-3,3-dimethylindolin-2-one

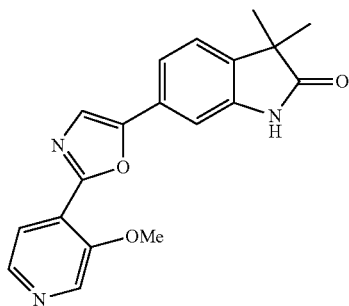 [SMILES: COc1cnccc1-c1ncc(-c2ccc3c(c2)NC(=O)C3(C)C)o1]

a) Methyl 3,3-dimethyl-2-oxoindoline-6-carboxylate

A mixture of 3,3-dimethyl-2-oxoindoline-6-carboxylic acid (8.29 g) from example 28a in MeOH (30 ml) and sulfuric acid (825 mg) was heated to reflux temperature for 16 h. The mixture was partitioned between aqueous sodium carbonate (2 M) and dichloromethane, the organic layer was dried, evaporated, the residue triturated with EtOAc and diisopropylether (1:1, 70 ml), filtered and the residue dried to give the crude title compound (4.50 g, 51%) as a light red solid, which was used without further purification. MS (ESI, m/z): 220.5 [(M+H)+].

b) 6-(Hydroxymethyl)-3,3-dimethylindolin-2-one

To a solution of methyl 3,3-dimethyl-2-oxoindoline-6-carboxylate (8.59 g) in THF (390 ml) was added at 22° C. LiBH4 (5.12 g) and stirring was continued at 50° C. for 60 h. The mixture was partitioned between saturated aqueous ammonium chloride and EtOAc, the organic layer was dried and evaporated to give the crude title compound (8.32 g, quant.) as an yellow solid, which was used without further purification. MS (ESI, m/z): 192.5 [(M+H)+].

c) 3,3-Dimethyl-2-oxoindoline-6-carbaldehyde

A suspension of 6-(hydroxymethyl)-3,3-dimethylindolin-2-one (7.55 g) and manganese dioxide (20.6 g) in dichloromethane (395 ml) was heated to reflux temperature for 16 h. The mixture was filtered and the residue purified by flash chromatography (silica gel, gradient, 0% to 100% MeOH in dichloromethane) to give the title compound (5.99 g, 80%) as a brown solid. MS (ESI, m/z): 190.4 [(M+H)+].

d) 3,3-Dimethyl-6-(oxazol-5-yl)indolin-2-one

To a suspension of 3,3-dimethyl-2-oxoindoline-6-carbaldehyde (5.90 g) and potassium carbonate (5.60 g) in methanol (43 ml) was added tosylmethyl isocyanide (6.09 g) and stirring was continued at 80° C. for 3 h. The mixture was partitioned between water and dichloromethane, the organic layer was dried and evaporated to give the crude title compound (6.45 g, 91%) as an orange solid, which was used without further purification. MS (ESI, m/z): 229.5 [(M+H)+].

e) 6-(2-Chlorooxazol-5-yl)-3,3-dimethylindolin-2-one

To a solution of 3,3-dimethyl-6-(oxazol-5-yl)indolin-2-one (6.35 g) in THF (110 ml) was added at −78° C. a solution of LiHMDS (1 M in THF, 58 ml) and the mixture was warmed to 22° C. over 1.5 h. Hexachloroethane (7.00 g) was added and stirring was continued for at RT for 1.5 h. The mixture was partitioned between saturated aqueous sodium hydrogencarbonate and TBME, the organic layer was dried, evaporated and the residue purified by flash chromatography (silica gel, gradient, 0% to 100% EtOAc in n-heptane) to give the title compound (4.90 g, 67%) as an orange solid. MS (ESI, m/z): 263.4 [(M+H)+].

f) 6-(2-Chlorooxazol-5-yl)-1-(4-methoxybenzyl)-3,3-dimethylindolin-2-one

A mixture of 6-(2-chlorooxazol-5-yl)-3,3-dimethylindolin-2-one (2.00 g), 1-(chloromethyl)-4-methoxybenzene (1.31 g) and cesium carbonate (4.96 g) in DMF (51 ml) was heated to 80° C. for 3 h. The mixture was partitioned between water and EtOAc, the organic layer was dried, evaporated and the residue purified by flash chromatography (silica gel, gradient, 0% to 100% EtOAc in n-heptane) to give the title compound (2.13 g, 73%) as a light yellow semisolid. MS (ESI, m/z): 383.4 [(M+H)+].

g) 1-(4-Methoxybenzyl)-6-(2-(3-methoxypyridin-4-yl)oxazol-5-yl)-3,3-dimethylindolin-2-one A mixture of 6-(2-chlorooxazol-5-yl)-1-(4-methoxybenzyl)-3,3-dimethylindolin-2-one (500 mg) and 3-methoxypyridin-4-ylboronic acid (367 mg) in 1,4-dioxane (10 ml) and aqueous sodium carbonate (2 M, 2.6 ml) was flushed with argon, then bis(triphenylphosphine)palladium(II)dichloride (141 mg) was added and stirring was continued at reflux temperature for 16 h. The mixture was evaporated and the residue purified by flash chromatography (silica gel, gradient, 0% to 10% MeOH in dichloromethane) to give the still impure title compound (274 mg, 46%) as a brown foam, which was used without further purification. MS (ESI, m/z): 456.4 [(M+H)+].

h) 6-(2-(3-Methoxypyridin-4-yl)oxazol-5-yl)-3,3-dimethylindolin-2-one (Example 63)

A solution of 1-(4-methoxybenzyl)-6-(2-(3-methoxypyridin-4-yl)oxazol-5-yl)-3,3-dimethylindolin-2-one (270 mg) in TFA (4 ml) was heated to 120° C. for 16 h. The mixture was partitioned between aqueous sodium carbonate (2 M) and EtOAc, the organic layer was dried, evaporated and the residue purified by flash chromatography (silica gel, gradient, 0% to 10% MeOH in dichloromethane) to give the title compound (71 mg, 36%) as a brown solid. MS (ESI, m/z): 336.5 [(M+H)+].

Example 64

1,3,3-Trimethyl-6-(3-(2-methylpyridin-4-yl)isoxazol-5-yl)indolin-2-one

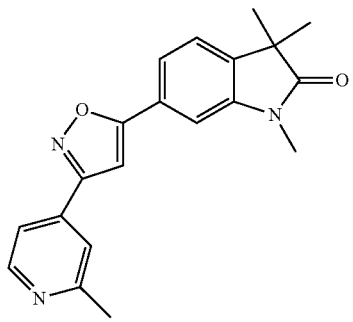 [SMILES: Cc1cc(-c2cc(-c3ccc4c(c3)N(C)C(=O)C4(C)C)on2)ccn1]

a) 1-(2-Methylpyridin-4-yl)-3-(1,3,3-trimethyl-2-oxoindolin-6-yl)propane-1,3-dione The title compound was prepared from 6-acetyl-1,3,3-trimethylindolin-2-one from example 3a and methyl 2-methylisonicotinate in analogy to example 42a to give the title compound (76%) as an orange oil. MS (ESI, m/z): 337.5 [(M+H)+].

b) 1,3,3-Trimethyl-6-(3-(2-methylpyridin-4-yl)isoxazol-5-yl)indolin-2-one (Example 64)

Example 64 was prepared from 1-(2-methylpyridin-4-yl)-3-(1,3,3-trimethyl-2-oxoindolin-6-yl)propane-1,3-dione in analogy to example 42b to give the title compound (18%) as a light brown solid. MS (ESI, m/z): 334.2 [(M+H)+].

Example 65

1,3,3-Trimethyl-6-(5-(pyridin-3-yl)-1H-pyrazol-3-yl)indolin-2-one

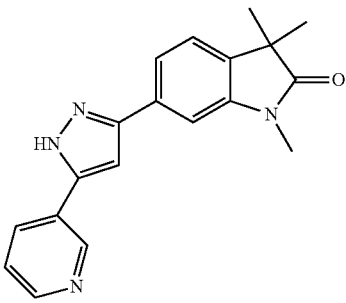 [SMILES: CN1C(=O)C(C)(C)c2ccc(-c3cc(-c4cccnc4)[nH]n3)cc21]

a) 1-(Pyridin-3-yl)-3-(1,3,3-trimethyl-2-oxoindolin-6-yl)propane-1,3-dione

The title compound was prepared from 6-acetyl-1,3,3-trimethylindolin-2-one from example 3a and methyl nicotinate in analogy to example 42a to give the title compound (79%) as a yellow solid. MS (ESI, m/z): 323.5 [(M+H)+].

b) 1,3,3-Trimethyl-6-(5-(pyridin-3-yl)-1H-pyrazol-3-yl)indolin-2-one (Example 65)

Example 65 was prepared from 1-(pyridin-3-yl)-3-(1,3,3-trimethyl-2-oxoindolin-6-yl)propane-1,3-dione in analogy to example 56 to give the title compound (50%) as a white solid. MS (ESI, m/z): 319.5 [(M+H)+].

Example 66

1-Ethyl-3,3-dimethyl-6-(4-(2-methylpyridin-4-yl)-1H-pyrazol-1-yl)indolin-2-one

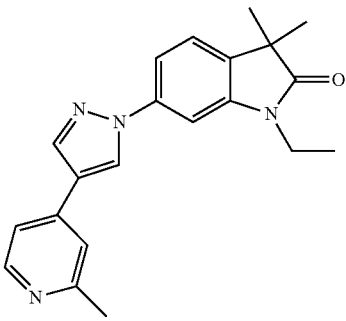 [SMILES: CCN1C(=O)C(C)(C)c2ccc(-n3cc(-c4ccnc(C)c4)cn3)cc21]

a) 6-Bromo-1-ethyl-3,3-dimethylindolin-2-one

To a solution of 6-bromo-3,3-dimethylindolin-2-one (465 mg) from example 1a in dry THF (12 ml) was added at 0° C. a solution of sodium bis(trimethylsilyl)amide (1M in THF, 6 ml) followed by ethyl iodide (1.03 g) and stirring was continued at 0° C. for 30 min and at 50° C. for 16 h. The mixture was partitioned between water and EtOAc, the organic layer was dried, evaporated and the residue purified by flash chromatography (silica gel, gradient, 0% to 100% EtOAc in n-heptane) to give the title compound (490 mg, 94%) as a yellow oil. MS (ESI, m/z): 269.4 [(M+H)⁺].

b) 1-Ethyl-3,3-dimethyl-6-(4-(2-methylpyridin-4-yl)-1H-pyrazol-1-yl)indolin-2-one (Example 66)

Example 66 was prepared from 6-bromo-1-ethyl-3,3-dimethylindolin-2-one and 2-methyl-4-(1H-pyrazol-4-yl)pyridine from example 54a in analogy to example 40 to give the title compound (55%) as a white solid. MS (ESI, m/z): 347.6 [(M+H)⁺].

Example 67

6-[1-(2-Fluoropyridin-4-yl)imidazol-4-yl]-1,3,3-trimethylindol-2-one

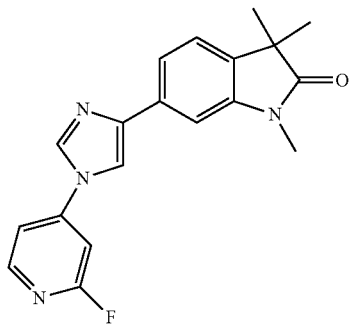 [SMILES: CN1C(=O)C(C)(C)c2ccc(-c3cn(-c4ccnc(F)c4)cn3)cc21]

Example 67 was prepared from 6-(1H-imidazol-5-yl)-1,3,3-trimethylindolin-2-one from example 59d and 4-bromo-3-fluoropyridine hydrochloride in analogy to example 59e to give the title compound (9%) as a brown solid. MS (ESI, m/z): 337.5 [(M+H)⁺].

Example 68

1,3,3-Trimethyl-6-(4-(6-methylpyridin-3-yl)-1H-pyrazol-1-yl)indolin-2-one

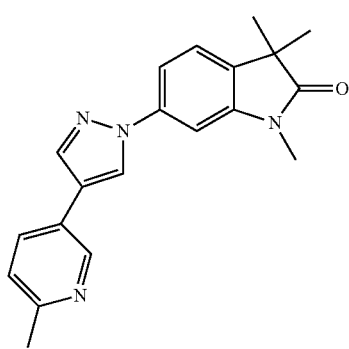 [SMILES: Cc1ccc(-c2cnn(-c3ccc4c(c3)N(C)C(=O)C4(C)C)c2)cn1]

a) 2-Methyl-5-(1H-pyrazol-4-yl)pyridine

The title compound was prepared from 5-bromo-2-methylpyridine and tert-butyl 4-(4,4,5,5-tetramethyl-1,3,2-dioxaborolan-2-yl)-1H-pyrazole-1-carboxylate in analogy to example 41a and obtained as a brown solid (78%). MS (ESI, m/z): 158.2 [(M−H)⁻].

b) 1,3,3-Trimethyl-6-(4-(6-methylpyridin-3-yl)-1H-pyrazol-1-yl)indolin-2-one (Example 68)

Example 68 was prepared from 6-bromo-1,3,3-trimethylindolin-2-one from example 2a and 2-methyl-5-(1H-pyrazol-4-yl)pyridine in analogy to example 40 to give the title compound (30%) as a white solid. MS (ESI, m/z): 333.6 [(M+H)⁺].

Example 69

1-Cyclopropyl-3,3-dimethyl-6-(4-(6-methylpyridin-3-yl)-1H-pyrazol-1-yl)indolin-2-one

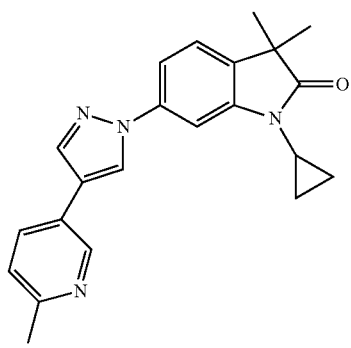 [SMILES: Cc1ccc(-c2cnn(-c3ccc4c(c3)N(C3CC3)C(=O)C4(C)C)c2)cn1]

Example 69 was prepared from 6-bromo-1-cyclopropyl-3,3-dimethylindolin-2-one from example 1b and 2-methyl-5-(1H-pyrazol-4-yl)pyridine from example 68a in analogy to example 40 to give the title compound (34%) as a white foam. MS (ESI, m/z): 359.6 [(M+H)⁺].

Example 70

3,3-Dimethyl-6-(4-(2-methylpyridin-4-yl)-1H-pyrazol-1-yl)-1-(oxetan-3-yl)indolin-2-one

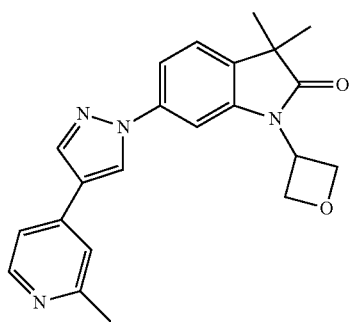 [SMILES: Cc1cc(-c2cnn(-c3ccc4c(c3)N(C3COC3)C(=O)C4(C)C)c2)ccn1]

Example 70 was prepared from 6-bromo-3,3-dimethyl-1-(oxetan-3-yl)indolin-2-one from example 6a and 2-methyl-4-(1H-pyrazol-4-yl)pyridine from example 54a in analogy

Example 71

1-Cyclopropyl-3,3-dimethyl-6-(1-(pyridin-3-yl)-1H-imidazol-4-yl)indolin-2-one

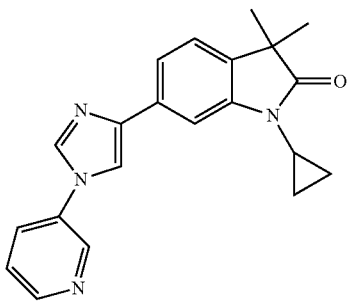 [SMILES: CC1(C)C(=O)N(C2CC2)c2cc(-c3cn(-c4cccnc4)cn3)ccc21]

a) 1-Cyclopropyl-6-(1H-imidazol-5-yl)-3,3-dimethylindolin-2-one

The title compound was prepared from 1-cyclopropyl-3,3-dimethyl-2-oxoindoline-6-carboxylic from example 4b in analogy to example 59a-d and obtained as a light brown foam (48%). MS (ESI, m/z): 268.5 [(M+H)$^+$].

b) 1-Cyclopropyl-3,3-dimethyl-6-(1-(pyridin-3-yl)-1H-imidazol-4-yl)indolin-2-one (Example 71)

Example 71 was prepared from 1-cyclopropyl-6-(1H-imidazol-5-yl)-3,3-dimethylindolin-2-one and 3-bromopyridine in analogy to example 59e to give the title compound (61%) as an off-white foam. MS (ESI, m/z): 345.5 [(M+H)$^+$].

Example 72

1-Cyclopropyl-3,3-dimethyl-6-(1-(pyridin-4-yl)-1H-imidazol-4-yl)indolin-2-one

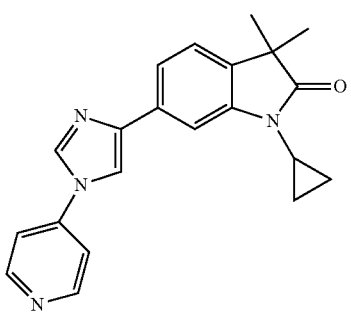 [SMILES: CC1(C)C(=O)N(C2CC2)c2cc(-c3cn(-c4ccncc4)cn3)ccc21]

Example 72 was prepared from 1-cyclopropyl-6-(1H-imidazol-5-yl)-3,3-dimethylindolin-2-one from example 71a and 4-bromopyridine in analogy to example 59e to give the title compound (38%) as an off-white foam. MS (ESI, m/z): 345.5 [(M+H)$^+$].

Example 73

6-(1-(3-Fluoropyridin-4-yl)-1H-imidazol-4-yl)-1,3,3-trimethylindolin-2-one

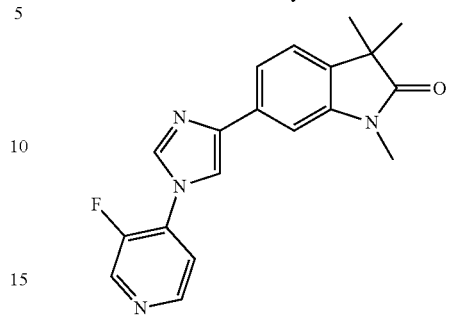

Example 73 was prepared from 6-(1H-imidazol-5-yl)-1,3,3-trimethylindolin-2-one from example 59d and 4-bromo-3-fluoropyridine hydrochloride in analogy to example 59e to give the title compound (59%) as a light brown solid. MS (ESI, m/z): 337.2 [(M+H)$^+$].

Example 74

1-Cyclopropyl-3,3-dimethyl-6-(1-(2-methylpyridin-4-yl)-1H-imidazol-4-yl)indolin-2-one

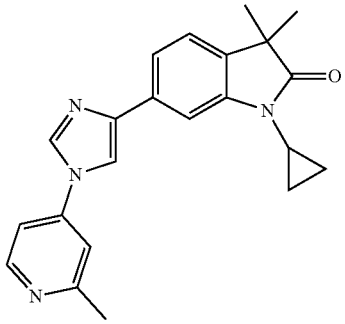 [SMILES: Cc1cc(-n2cnc(-c3ccc4c(c3)N(C3CC3)C(=O)C4(C)C)c2)ccn1]

Example 74 was prepared from 1-cyclopropyl-6-(1H-imidazol-5-yl)-3,3-dimethylindolin-2-one form example 71a and 4-bromo-2-methylpyridine in analogy to example 59e to give the title compound (46%) as an off-white foam. MS (ESI, m/z): 359.5 [(M+H)$^+$].

Example 75

1-Cyclopropyl-3,3-dimethyl-6-(3-(2-methylpyridin-4-yl)isoxazol-5-yl)indolin-2-one

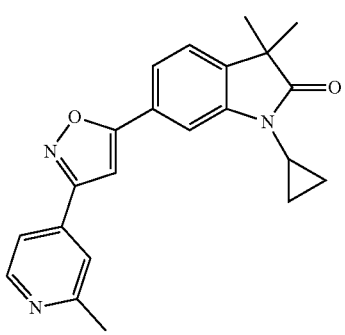 [SMILES: Cc1cc(-c2cc(-c3ccc4c(c3)N(C3CC3)C(=O)C4(C)C)on2)ccn1]

a) 6-Acetyl-1-cyclopropyl-3,3-dimethylindolin-2-one

The title compound was prepared from 6-bromo-1-cyclopropyl-3,3-dimethylindolin-2-one from example 1b in analogy to example 3a and obtained as a light yellow solid (76%). MS (ESI, m/z): 344.5 [(M+H)⁺].

b) 1-Cyclopropyl-3,3-dimethyl-6-(3-(2-methylpyridin-4-yl)isoxazol-5-yl)indolin-2-one (Example 75)

Example 75 was prepared from 1-(1-cyclopropyl-3,3-dimethyl-2-oxo-indolin-6-yl)-3-(2-methyl-4-pyridyl)propane-1,3-dione (obtained from 6-acetyl-1-cyclopropyl-3,3-dimethylindolin-2-one and methyl 2-methylpyridine-4-carboxylate in analogy to example 42a) in analogy to example 42b to give the title compound (56%) as a white foam. MS (ESI, m/z): 360.8 [(M+H)⁺].

Example 76

1-Cyclopropyl-6-(1-(3-fluoropyridin-4-yl)-1H-imidazol-4-yl)-3,3-dimethylindolin-2-one

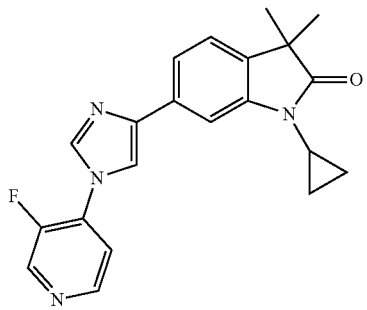 [SMILES: CC1(C)C(=O)N(C2CC2)c2cc(-c3cn(-c4ccncc4F)cn3)ccc21]

Example 76 was prepared from 1-cyclopropyl-6-(1H-imidazol-5-yl)-3,3-dimethylindolin-2-one from example 71a and 4-bromo-3-fluoropyridine hydrochloride in analogy to example 59e to give the title compound (23%) as an off-white foam. MS (ESI, m/z): 363.2 [(M+H)⁺].

Example 77

1,3,3-Trimethyl-6-(2-methyl-1-(pyridin-4-yl)-1H-imidazol-4-yl)indolin-2-one a) 1,3,3-Trimethyl-6-(2-methyl-1H-imidazol-5-yl)indolin-2-one

To a solution of acetamidine (735 mg) in dichloromethane (50 ml) was added at 22° C. a solution of 6-(2-bromoacetyl)-1,3,3-trimethylindolin-2-one (1.50 g) from example 3b in dichloromethane (5 ml) and stirring was continued for 16 h. The mixture was partitioned between aqueous sodium carbonate (2 M) and dichloromethane, the organic layer was dried, evaporated and the residue purified by flash chromatography (silica gel, gradient, 0% to 10% EtOAc in n-heptane) to give the title compound (966 mg, 75%) as an off-white foam. MS (ESI, m/z): 256.5 [(M+H)⁺].

b) 1,3,3-Trimethyl-6-(2-methyl-1-(pyridin-4-yl)-1H-imidazol-4-yl)indolin-2-one (Example 77)

Example 77 was prepared from 1,3,3-trimethyl-6-(2-methyl-1H-imidazol-5-yl)indolin-2-one and 4-bromopyridine hydrochloride in analogy to example 59e to give the title compound (50%) as a light yellow foam. MS (ESI, m/z): 333.5 [(M+H)⁺].

Example 78

1,3,3-Trimethyl-6-(2-methyl-1-(2-methylpyridin-4-yl)-1H-imidazol-4-yl)indolin-2-one

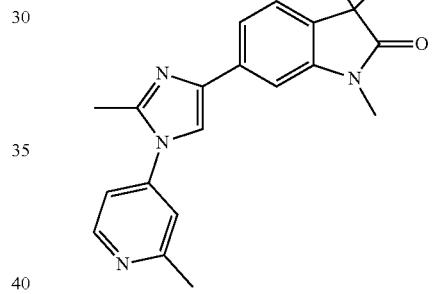

Example 78 was prepared from 1,3,3-trimethyl-6-(2-methyl-1H-imidazol-5-yl)indolin-2-one from example 77a and 4-bromo-2-methylpyridine in analogy to example 59e to give the title compound (46%) as a light yellow foam. MS (ESI, m/z): 347.5 [(M+H)⁺].

Example 79

6-(1-(3-Fluoropyridin-4-yl)-2-methyl-1H-imidazol-4-yl)-1,3,3-trimethylindolin-2-one

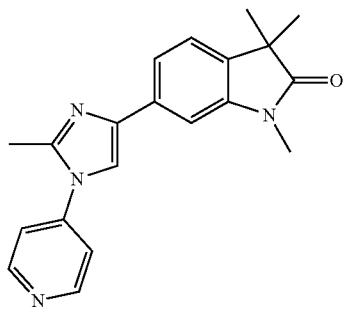 [SMILES: Cc1nc(-c2ccc3c(c2)N(C)C(=O)C3(C)C)cn1-c1ccncc1]

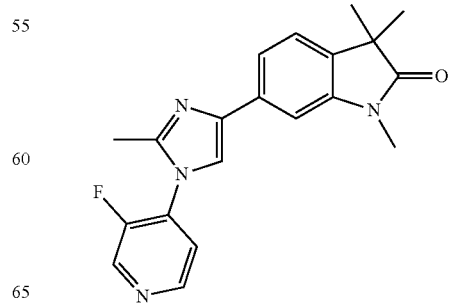

Example 79 was prepared from 1,3,3-trimethyl-6-(2-methyl-1H-imidazol-5-yl)indolin-2-one from example 77a and 4-bromo-3-fluoropyridine hydrochloride in analogy to example 59e to give the title compound (23%) as a light brown foam. MS (ESI, m/z): 351.5 [(M+H)$^+$].

Example 80

1,3,3-Trimethyl-6-(5-(6-methylpyridin-3-yl)-1H-pyrazol-3-yl)indolin-2-one

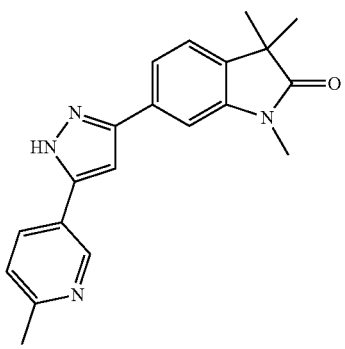 [SMILES: Cc1ccc(-c2cc(-c3ccc4c(c3)N(C)C(=O)C4(C)C)n[nH]2)cn1]

a) 1-(6-Methylpyridin-3-yl)-3-(1,3,3-trimethyl-2-oxoindolin-6-yl)propane-1,3-dione The title compound was prepared from 6-acetyl-1,3,3-trimethylindolin-2-one from example 3a and methyl 6-methylnicotinate in analogy to example 42a and obtained as a yellow oil (48%). MS (ESI, m/z): 337.6 [(M+H)$^+$].

b) 1,3,3-Trimethyl-6-(5-(6-methylpyridin-3-yl)-1H-pyrazol-3-yl)indolin-2-one (Example 80)

Example 80 was prepared from 1-(6-methylpyridin-3-yl)-3-(1,3,3-trimethyl-2-oxoindolin-6-yl)propane-1,3-dione in analogy to example 56 to give the title compound (69%) as a yellow solid. MS (ESI, m/z): 333.8 [(M+H)$^+$].

Example 81

1,3,3-Trimethyl-6-(1-methyl-5-(2-methylpyridin-4-yl)-1H-pyrazol-3-yl)indolin-2-one

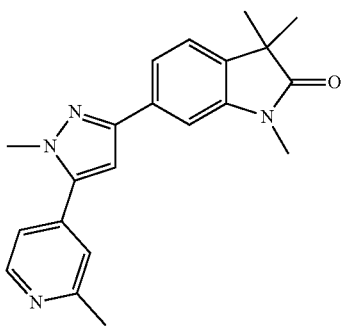 [SMILES: Cc1cc(-c2cc(-c3ccc4c(c3)N(C)C(=O)C4(C)C)nn2C)ccn1]

Example 81 was prepared in analogy to example 61b using methylhydrazine. The crude material was purified by flash chromatography (silica gel, gradient, 0% to 5% MeOH in dichloromethane) to give 1,3,3-trimethyl-6-(1-methyl-3-(2-methylpyridin-4-yl)-1H-pyrazol-5-yl)indolin-2-one (67%) as the faster eluting isomer as a white solid. The slower eluting isomer contained the title compound (29%) as a white solid. MS (ESI, m/z): 347.5 [(M+H)$^+$].

Example 82

1,3,3-Trimethyl-6-(2-(2-methylpyridin-4-yl)pyrimidin-4-yl)indolin-2-one

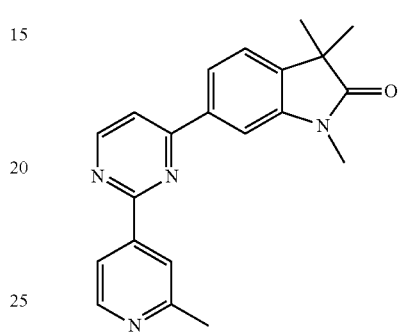

a) 1,3,3-Trimethyl-6-(4,4,5,5-tetramethyl-1,3,2-dioxaborolan-2-yl)indolin-2-one

A mixture of 6-bromo-1,3,3-trimethylindolin-2-one (5.00 g) from example 2a, bis(pinacolato)diboron (7.57 g) and potassium acetate (3.90 g) in DMSO (66 ml) was flushed with argon, then [1,1'-bis(diphenylphosphino)ferrocene]dichloropalladium(II) (720 mg) was added and stirring was continued at 110° C. for 16 h. The mixture was filtered, the filtrate partitioned between aqueous hydrochloric acid (0.1 M) and EtOAc, the organic layer was dried, evaporated and the residue purified by flash chromatography (silica gel, 0% to 40% EtOAc in n-heptane) followed by trituration with EtOAc/n-heptane (1:1) to give the title compound (4.16 g, 70%) as a white solid. MS (ESI, m/z): 302.2 [(M+H)$^+$].

b) 6-(2-Chloropyrimidin-4-yl)-1,3,3-trimethylindolin-2-one

A mixture of 1,3,3-trimethyl-6-(4,4,5,5-tetramethyl-1,3,2-dioxaborolan-2-yl)indolin-2-one (450 mg), 4-bromo-2-chloropyrimidine (578 mg) and aqueous sodium carbonate (2 M, 1.5 ml) in 1,4-dioxane (8 ml) was flushed with argon, then [1,1'-bis(diphenylphosphino)ferrocene]dichloropalladium(II) (61 mg) was added and stirring was continued at 80° C. for 2 h. The mixture was evaporated and the residue purified by flash chromatography (Si—NH2, gradient, 0% to 50% EtOAc in n-heptane) to give the title compound (367 mg, 85%) as a white solid. MS (ESI, m/z): 288.4 [(M+H)$^+$].

c) 1,3,3-Trimethyl-6-(2-(2-methylpyridin-4-yl)pyrimidin-4-yl)indolin-2-one (Example 82)

A mixture of 6-(2-chloropyrimidin-4-yl)-1,3,3-trimethylindolin-2-one (110 mg), 2-methylpyridin-4-ylboronic acid (106 mg) and cesium carbonate (500 mg) in THF (3 ml) and water (1.5 ml) was flushed with argon, [1,1'-bis(diphenylphosphino)ferrocene]dichloropalladium(II) (32 mg) was added and stirring was continued at 80° C. for 16 h. The mixture was evaporated and the residue purified by flash chromatography (Si—NH2, gradient, 0% to 40% EtOAc in n-heptane) to give the title compound (90 mg, 68%) as a light yellow foam. MS (ESI, m/z): 345.6 [(M+H)+].

Example 83

1,3,3-Trimethyl-6-(2-(6-methylpyridin-3-yl)pyrimidin-4-yl)indolin-2-one

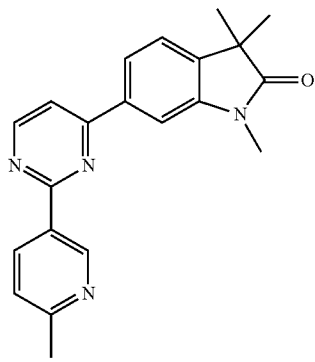 [SMILES: Cc1ccc(-c2nccc(-c3ccc4c(c3)N(C)C(=O)C4(C)C)n2)cn1]

Example 83 was prepared from 6-(2-chloropyrimidin-4-yl)-1,3,3-trimethylindolin-2-one from example 82b and 6-methylpyridin-3-ylboronic acid in analogy to example 82c to give the title compound (108 mg, 82%) as a white solid. MS (ESI, m/z): 345.6 [(M+H)+].

Example 84

1,3,3-Trimethyl-6-(4-methyl-3-(2-methylpyridin-4-yl)-1H-pyrazol-5-yl)indolin-2-one

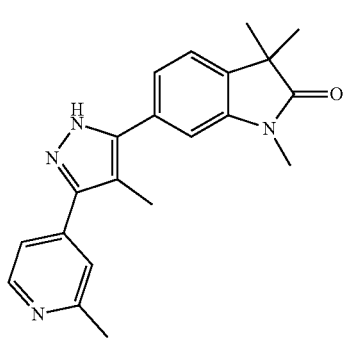 [SMILES: Cc1cc(-c2n[nH]c(-c3ccc4c(c3)N(C)C(=O)C4(C)C)c2C)ccn1]

a) 2-Methyl-1-(2-methylpyridin-4-yl)-3-(1,3,3-trimethyl-2-oxoindolin-6-yl)propane-1,3-dione To a mixture of 1-(2-methylpyridin-4-yl)-3-(1,3,3-trimethyl-2-oxoindolin-6-yl)propane-1,3-dione from example 61a (433 mg) and potassium carbonate (267 mg) DMF (1.5 ml) was added iodomethane (201 mg) and stirring was continued at 60° C. for 16 h. The mixture was evaporated and the residue purified by flash chromatography (Si—NH2, gradient, 0% to 100% EtOAc in n-heptane) to give the title compound (89 mg, 20%) as a light brown solid. MS (ESI, m/z): 351.6 [(M+H)+].

b) 1,3,3-Trimethyl-6-(4-methyl-3-(2-methylpyridin-4-yl)-1H-pyrazol-5-yl)indolin-2-one (Example 84)

A solution of 2-methyl-1-(2-methylpyridin-4-yl)-3-(1,3,3-trimethyl-2-oxoindolin-6-yl)propane-1,3-dione (89 mg), p-toluenesulfonic acid monohydrate (3 mg) and hydrazine monohydrate (254 mg) in THF (1.2 ml) was stirred 70° C. for 17 h. The mixture was evaporated and the residue purified by flash chromatography (Si—NH2, gradient, 0% to 70% EtOAc in n-heptane) to give the title compound (65 mg, 74%) as a light yellow solid. MS (ESI, m/z): 347.5 [(M+H)+].

Example 85

3,3-Dimethyl-6-(2-(6-methylpyridin-3-yl)pyrimidin-4-yl)-1-(oxetan-3-yl)indolin-2-one

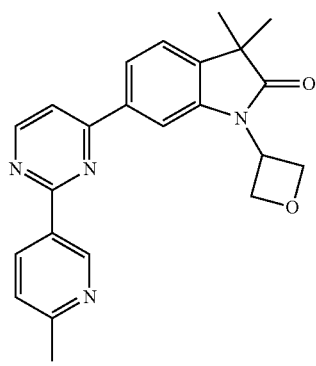 [SMILES: Cc1ccc(-c2nccc(-c3ccc4c(c3)N(C3COC3)C(=O)C4(C)C)n2)cn1]

a) 6-(2-Chloropyrimidin-4-yl)-3,3-dimethyl-1-(oxetan-3-yl)indolin-2-one

The title compound was prepared from 6-bromo-3,3-dimethyl-1-(oxetan-3-yl)indolin-2-one from example 6a in analogy to example 82a-b and obtained as a light brown solid. MS (ESI, m/z): 330.1 [(M+H)+].

b) 3,3-Dimethyl-6-(2-(6-methylpyridin-3-yl)pyrimidin-4-yl)-1-(oxetan-3-yl)indolin-2-one (Example 85)

Example 85 was prepared from 6-(2-chloropyrimidin-4-yl)-3,3-dimethyl-1-(oxetan-3-yl)indolin-2-one and 6-methylpyridin-3-ylboronic acid in analogy to example 82c to give the title compound (85%) as a brown solid. MS (ESI, m/z): 387.2 [(M+H)+].

Example 86

1-Cyclopropyl-3,3-dimethyl-6-(2-methyl-1-(2-methylpyridin-4-yl)-1H-imidazol-4-yl)indolin-2-one

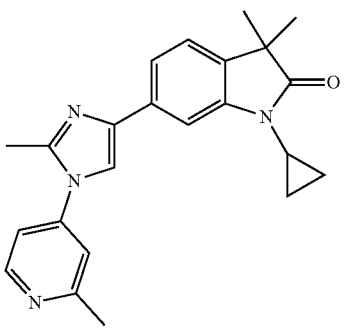 [SMILES: Cc1cc(-n2cc(-c3ccc4c(c3)N(C3CC3)C(=O)C4(C)C)nc2C)ccn1]

a) 6-Acetyl-1-cyclopropyl-3,3-dimethylindolin-2-one

The title compound was prepared from 6-bromo-1-cyclopropyl-3,3-dimethylindolin-2-one from example 1b in analogy to example 3a and obtained as a light yellow solid (45%). MS (ESI, m/z): 244.6 [(M+H)$^+$].

b) 6-(2-Bromoacetyl)-1-cyclopropyl-3,3-dimethylindolin-2-one

To a solution of 6-acetyl-1-cyclopropyl-3,3-dimethylindolin-2-one (1.00 g) in THF (24 ml) and MeOH (16 ml) was added a solution of tetra-n-butylammonium tribromide (2.02 g) in THF (8 ml) and stirring was continued at 50° C. for 5 h. The mixture was evaporated and the residue purified by flash chromatography (silica gel, 0% to 30% EtOAc in n-heptane) to give the crude title compound (1.39 g, 87%) as a yellow viscous oil, which was used without further purification. MS (ESI, m/z): 322.0/324.0 [(M+H)$^+$].

c) 1-Cyclopropyl-3,3-dimethyl-6-(2-methyl-1H-imidazol-5-yl)indolin-2-one

To a solution of acetamidine (631 mg) in dichloromethane (45 ml) was added at 22° C. a solution of 6-(2-bromoacetyl)-1-cyclopropyl-3,3-dimethylindolin-2-one (1.40 g) in dichloromethane (5 ml) and stirring was continued for 16 h. The mixture was partitioned between aqueous sodium carbonate (2 M) and EtOAc, the organic layer was dried, evaporated and the residue purified by flash chromatography (silica gel, 0% to 10% MeOH in dichloromethane) to give the title compound (543 mg, 44%) as a purple foam. MS (ESI, m/z): 282.5 [(M+H)$^+$].

d) 1-Cyclopropyl-3,3-dimethyl-6-(2-methyl-1-(2-methylpyridin-4-yl)-1H-imidazol-4-yl)indolin-2-one (Example 86)

Example 86 was prepared from 1-cyclopropyl-3,3-dimethyl-6-(2-methyl-1H-imidazol-5-yl)indolin-2-one and 4-bromo-2-methylpyridine in analogy to example 59e to give the title compound (51%) as a brown solid. MS (ESI, m/z): 373.2 [(M+H)$^+$].

Example 87

1-Cyclopropyl-6-(1-(3-fluoropyridin-4-yl)-2-methyl-1H-imidazol-4-yl)-3,3-dimethylindolin-2-one

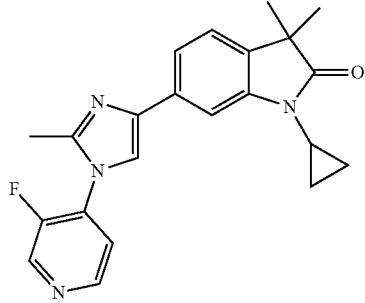 [SMILES: Cc1nc(-c2ccc3c(c2)N(C2CC2)C(=O)C3(C)C)cn1-c1ccncc1F]

Example 87 was prepared from 1-cyclopropyl-3,3-dimethyl-6-(2-methyl-1H-imidazol-5-yl)indolin-2-one from example 86c and 4-bromo-3-fluoropyridine hydrochloride in analogy to example 59e to give the title compound (25%) as a light brown foam. MS (ESI, m/z): 377.2 [(M+H)$^+$].

Example 88

1,3,3-Trimethyl-6-(1-(3-methylpyridin-4-yl)-1H-imidazol-4-yl)indolin-2-one

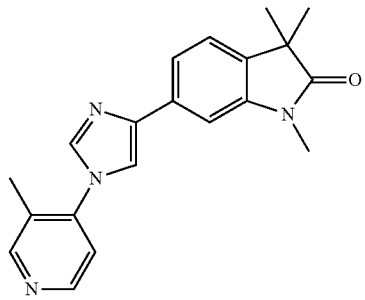 [SMILES: Cc1cnccc1-n1cnc(-c2ccc3c(c2)N(C)C(=O)C3(C)C)c1]

Example 88 was prepared from 6-(1H-imidazol-5-yl)-1,3,3-trimethylindolin-2-one from example 59d and 4-bromo-3-picoline hydrochloride in analogy to example 59e to give the title compound (58%) as a brown solid. MS (ESI, m/z): 333.2 [(M+H)$^+$].

Example 89

1-Cyclopropyl-3,3-dimethyl-6-(1-(3-methylpyridin-4-yl)-1H-imidazol-4-yl)indolin-2-one

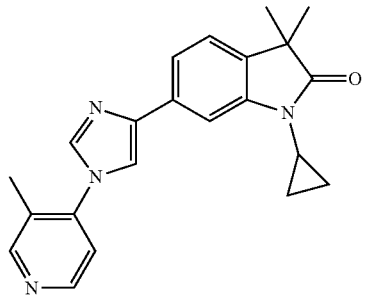 [SMILES: Cc1cnccc1-n1cnc(-c2ccc3c(c2)N(C2CC2)C(=O)C3(C)C)c1]

Example 89 was prepared from 1-cyclopropyl-6-(1H-imidazol-5-yl)-3,3-dimethylindolin-2-one from example 71a and 4-bromo-3-picoline hydrochloride in analogy to example 59e to give the title compound (54%) as a light yellow foam. MS (ESI, m/z): 359.2 [(M+H)+].

Example 90

1-Cyclopropyl-3,3-dimethyl-6-(1-(2-methylpyridin-4-yl)-1H-imidazol-4-yl)-1H-pyrrolo[3,2-c]pyridin-2(3H)-one

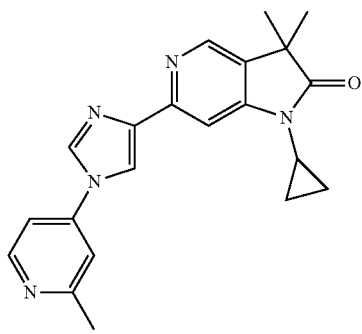 [SMILES: Cc1cc(-n2cnc(-c3cc4c(cn3)C(C)(C)C(=O)N4C3CC3)c2)ccn1]

a) 6-Chloro-1-cyclopropyl-3,3-dimethyl-1H-pyrrolo[3,2-c]pyridin-2(3H)-one

A mixture of 6-chloro-3,3-dimethyl-1H-pyrrolo[3,2-c]pyridin-2(3H)-one (600 mg, prepared according to Woolford et al., WO 2012143726), cyclopropylboronic acid (524 mg), copper(II)acetate (582 mg) and DMAP (1.12 g) in toluene (50 ml) was flushed with argon, then treated with sodium bis(trimethylsilyl)amide (2 M in THF, 1.6 ml) and stirring was continued at 95° C. for 16 h. The mixture was partitioned between aqueous hydrochloric acid (1 M) and TBME, the organic layer was dried, evaporated and the residue purified by flash chromatography (silica gel, 0% to 30% EtOAc in n-heptane) to give the title compound (547 mg, 76%) as a white solid. MS (ESI, m/z): 237.5 [(M+H)+].

b) 4-(1-Cyclopropyl-3,3-dimethyl-2-oxo-2,3-dihydro-1H-pyrrolo[3,2-c]pyridin-6-yl)-N,N-dimethyl-1H-imidazole-1-sulfonamide A mixture of 6-chloro-1-cyclopropyl-3,3-dimethyl-1H-pyrrolo[3,2-c]pyridin-2(3H)-one (195 mg) and N,N-dimethyl-4-(tributylstannyl)-1H-imidazole-1-sulfonamide (478 mg, prepared according to Altenbach et al., J. Med. Chem. 51, 6571, 2008) in dry DMF (4 ml) was flushed with argon, then tetrakis(triphenylphosphine)palladium(0) (114 mg) was added and stirring was continued at 80° C. for 16 h. The mixture was partitioned between saturated aqueous sodium hydrogencarbonate and EtOAc, the organic layer was dried, evaporated and the residue purified by flash chromatography (silica gel, 0% to 100% EtOAc in n-heptane) to give the title compound (193 mg, 62%) as a white solid.

c) 1-Cyclopropyl-6-(1H-imidazol-4-yl)-3,3-dimethyl-1H-pyrrolo[3,2-c]pyridin-2(3H)-one A suspension of 4-(1-cyclopropyl-3,3-dimethyl-2-oxo-2,3-dihydro-1H-pyrrolo[3,2-c]pyridin-6-yl)-N,N-dimethyl-1H-imidazole-1-sulfonamide (193 mg) in aqueous hydrochloric acid (2 M, 8 ml) was heated to 100° C. for 2 h. The mixture was evaporated and the residue purified by flash chromatography (silica gel, 0% to 10% MeOH in dichloromethane containing NH4OH) to give the title compound (123 mg, 89%) as a white foam. MS (ESI, m/z): 269.2 [(M+H)+].

d) 1-Cyclopropyl-3,3-dimethyl-6-(1-(2-methylpyridin-4-yl)-1H-imidazol-4-yl)-1H-pyrrolo[3,2-c]pyridin-2(3H)-one (Example 90)

A suspension of 1-cyclopropyl-6-(1H-imidazol-4-yl)-3,3-dimethyl-1H-pyrrolo[3,2-c]pyridin-2(3H)-one (80 mg), 4-fluoro-2-methylpyridine (42 mg) and cesium carbonate (185 mg) in acetonitrile (1 ml) was heated to reflux temperature for 3 h. The mixture was evaporated and the residue purified by flash chromatography (silica gel, 0% to 10% MeOH in dichloromethane) to give the title compound (59 mg, 55%) as a white foam. MS (ESI, m/z): 360.3 [(M+H)+].

Example 91

1-Cyclopropyl-6-(1-(3-fluoropyridin-4-yl)-1H-imidazol-4-yl)-3,3-dimethyl-1H-pyrrolo[3,2-c]pyridin-2(3H)-one

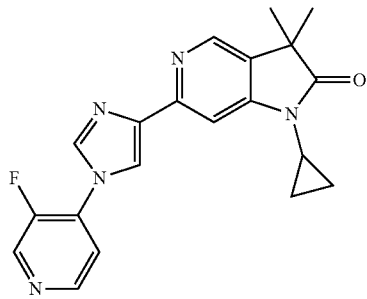 [SMILES: CC1(C)C(=O)N(C2CC2)c2cc(-c3cn(-c4ccncc4F)cn3)ncc21]

Example 91 was prepared analogy to example 90d using 3,4-difluoropyridine to give the title compound (87%) as a white foam. MS (ESI, m/z): 364.2 [(M+H)+].

Example 92

3,3-Dimethyl-6-(1-(2-methylpyridin-4-yl)-1H-imidazol-4-yl)indolin-2-one

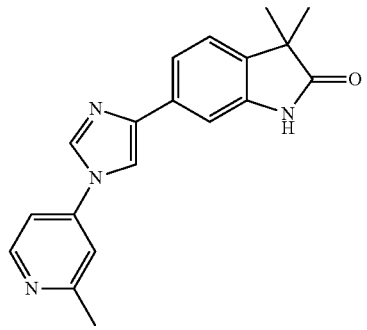 [SMILES: Cc1cc(-n2cnc(-c3ccc4c(c3)NC(=O)C4(C)C)c2)ccn1]

a) 6-(2-Bromoacetyl)-3,3-dimethylindolin-2-one

The title compound was prepared from 6-bromo-3,3-dimethylindolin-2-one from example 1a in analogy to example 3a-b and obtained as a white solid. MS (ESI, m/z): 282/284 [(M+H)$^+$].

b) 6-(1H-Imidazol-4-yl)-3,3-dimethylindolin-2-one

A solution of 6-(2-bromoacetyl)-3,3-dimethylindolin-2-one (1.00 g) in formamide (24 ml) was heated to 190° C. for 5 h. The mixture was partitioned between water and EtOAc, the organic layer was dried, evaporated and the residue purified by flash chromatography (silica gel, 0% to 15% MeOH in dichloromethane) to give the impure title compound (967 mg) as a brown solid, which was used without further purification. MS (ESI, m/z): 228.1 [(M+H)$^+$].

c) 3,3-Dimethyl-6-(1-(2-methylpyridin-4-yl)-1H-imidazol-4-yl)indolin-2-one (Example 92)

A mixture of 6-(1H-imidazol-4-yl)-3,3-dimethylindolin-2-one (100 mg), 4-fluoro-2-methylpyridine (86 mg) and cesium carbonate (186 mg) in acetonitrile (1 ml) was heated to 110° C. for 16 h. The mixture was evaporated and the residue purified by flash chromatography (silica gel, 0% to 10% MeOH in dichloromethane) followed by second flash chromatography (basic alumina, 0% to 10% MeOH in dichloromethane) to give the title compound (59 mg, 57%) as an off-white solid. MS (ESI, m/z): 319.3 [(M+H)$^+$].

Example 93

3,3-Dimethyl-6-(1-(pyridin-3-yl)-1H-imidazol-4-yl)indolin-2-one

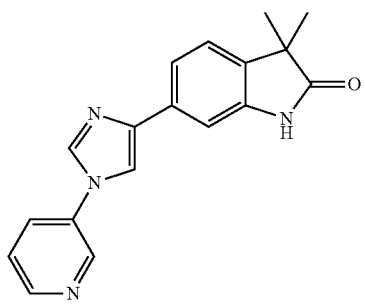 [SMILES: CC1(C)C(=O)Nc2cc(-c3cn(-c4cccnc4)cn3)ccc21]

a) 6-(1H-Imidazol-5-yl)-3,3-dimethylindolin-2-one

The title compound was prepared from 6-bromo-3,3-dimethylindolin-2-one in analogy to example 3a-b and using formamide in example 3c and obtained as a brown solid. MS (ESI, m/z): 228.1 [(M+H)$^+$].

b) 3,3-Dimethyl-6-(1-(pyridin-3-yl)-1H-imidazol-4-yl)indolin-2-one (Example 93)

A suspension of 6-(1H-imidazol-5-yl)-3,3-dimethylindolin-2-one (120 mg), 3-bromopyridine (200 mg), potassium carbonate (219 mg) and 2-acetylcyclohexanone (37 mg) in DMSO (2.5 ml) was flushed with argon, then copper(I) chloride (26 mg) was added and stirring was continued at 130° C. for 9 h. The mixture was partitioned between water and EtOAc, the organic layer was dried, evaporated and the residue purified by flash chromatography (silica gel, 0% to 10% MeOH in dichloromethane) followed by HPLC chromatography (RP-18, gradient, acetonitrile/water) to give the title compound (19 mg, 12%) as a white solid. MS (ESI, m/z): 305.1 [(M+H)$^+$].

Example 94

1-Cyclopropyl-3,3-dimethyl-6-[2-(2-methyl-pyridin-4-yl)-oxazol-5-yl]-1,3-dihydro-pyrrolo[3,2-c]pyridin-2-one

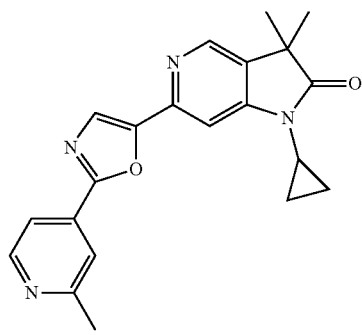 [SMILES: Cc1cc(-c2ncc(-c3cc4c(cn3)C(C)(C)C(=O)N4C3CC3)o2)ccn1]

A mixture of 2-(2-methylpyridin-4-yl)oxazole (0.13 g) from example 22a, 6-chloro-1-cyclopropyl-3,3-dimethyl-1H-pyrrolo[3,2-c]pyridin-2(3H)-one (0.384 g) from example 90a and cesium carbonate (0.52 g) in dioxane (5 ml) was flushed with argon, then Pd(OAc)2 (18 mg) and 2-(dicyclohexylphosphino)biphenyl (57 mg) were added and stirring was continued at 110° C. for 16 h. The mixture was partitioned between water and EtOAc, the organic layer was dried, evaporated and the residue purified by flash chromatography (silica gel, gradient, 0% to 30% EtOAc in n-heptane) to give the title compound (70 mg, 24%) as a light yellow solid. MS (ESI, m/z): 361.2 [(M+H)$^+$].

Example 95

6-(1-(5-Fluoro-2-methylpyridin-4-yl)-1H-imidazol-4-yl)-1,3,3-trimethylindolin-2-one

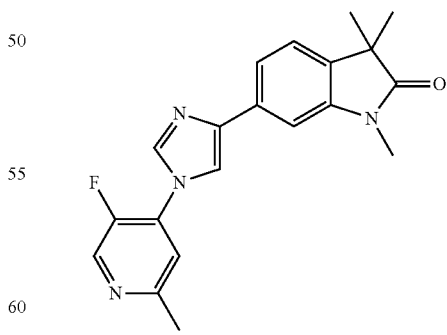

Example 95 was prepared from 6-(1H-imidazol-5-yl)-1,3,3-trimethylindolin-2-one from example 59d and 4-bromo-5-fluoro-2-methylpyridine in analogy to example 59e to give the title compound (58%) as a light brown oil. MS (ESI, m/z): 351.2 [(M+H)$^+$].

Example 96

6-(2-(5-Fluoro-2-methylpyridin-4-yl)oxazol-5-yl)-1,3,3-trimethylindolin-2-one

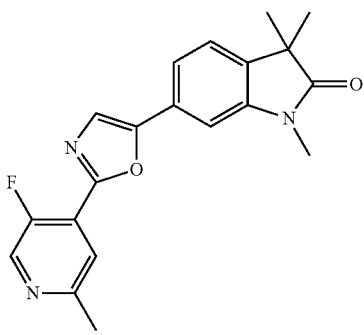 [SMILES: Cc1cc(-c2ncc(-c3ccc4c(c3)N(C)C(=O)C4(C)C)o2)c(F)cn1]

a) 6-(2-Azidoacetyl)-1,3,3-trimethylindolin-2-one

To a solution of 6-(2-bromoacetyl)-1,3,3-trimethylindolin-2-one (1.75 g) from example 3b in acetone (18 ml) was added at 22° C. sodium azide (767 mg) and stirring was continued for 6 h. The mixture was partitioned between water and dichloromethane, the organic layer was dried and evaporated to give the crude title compound (1.51 g, 99%) as a light yellow solid, which was used without further purification. MS (ESI, m/z): 259.1 [(M+H)$^+$].

b) 6-(2-(5-Fluoro-2-methylpyridin-4-yl)oxazol-5-yl)-1,3,3-trimethylindolin-2-one (Example 96)

To a solution of triphenylphosphine (570 mg) in toluene (4 ml) was subsequently added at 22° C. 6-(2-azidoacetyl)-1,3,3-trimethylindolin-2-one (330 mg) and a solution of 5-fluoro-2-methylisonicotinoyl chloride (222 mg) in toluene (2 ml) and stirring was continued for 2 h. The mixture was evaporated and the residue purified by flash chromatography (silica gel, gradient, 20% to 100% EtOAc in n-heptane) and by preparative HPLC (RP-18, gradient, acetonitrile/water) to give the title compound (50 mg, 11%) as light yellow solid. MS (ESI, m/z): 352.2 [(M+H)$^+$].

Example 97

3,3-Dimethyl-6-[5-(2-methyl-pyridin-4-yl)-[1,3,4]oxadiazol-2-yl]-1-oxetan-3-yl-1,3-dihydro-pyrrolo[3,2-c]pyridin-2-one

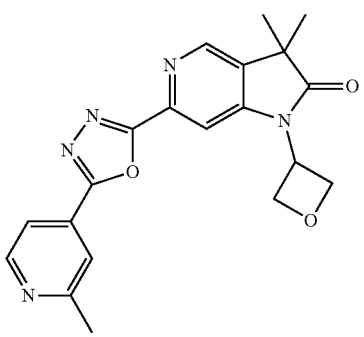 [SMILES: Cc1cc(-c2nnc(-c3cc4c(cn3)C(C)(C)C(=O)N4C3COC3)o2)ccn1]

a) 6-Chloro-3,3-dimethyl-1-oxetan-3-yl-1,3-dihydro-pyrrolo[3,2-c]pyridin-2-one A mixture of 6-chloro-3,3-dimethyl-1H-pyrrolo[3,2-c]pyridin-2(3H)-one (2.65 g, prepared according to Woolford et al., WO 2012143726), 3-bromooxetane (1.85 ml) and cesium carbonate (8.78 g) in DMF (20 ml) was heated to 60° C. for 16 h. The mixture was partitioned between saturated aqueous ammonium chloride and EtOAc, the organic layer was dried, evaporated and the residue purified by flash chromatography (silica gel, gradient, 0% to 30% EtOAc in n-heptane) to give the title compound (2.90 g, 85%) as a white solid. MS (ESI, m/z): 252.8 [(M+H)$^+$].

b) 3,3-Dimethyl-1-oxetan-3-yl-2-oxo-2,3-dihydro-1H-pyrrolo[3,2-c]pyridine-6-carboxylic acid methyl ester To a solution of 6-chloro-3,3-dimethyl-1-oxetan-3-yl-1,3-dihydro-pyrrolo[3,2-c]pyridin-2-one (2.90 g) in MeOH (30 ml) and DMF (3 ml) was added 1,1'-bis(diphenylphosphino)ferrocene-palladium(II)dichloride dichloromethane adduct (0.87 g) and the mixture was carbonylated at 100° C. and 150 psi CO pressure for 16 h. The mixture was evaporated and the residue partitioned between water and EtOAc, the organic layer was dried, evaporated and the residue purified by flash chromatography (silica gel, gradient, 0% to 100% EtOAc in n-heptane) to give the title compound (2.90 g, 92%) as a brown gum. MS (ESI, m/z): 276.8 [(M+H)$^+$].

c) 3,3-Dimethyl-1-oxetan-3-yl-2-oxo-2,3-dihydro-1H-pyrrolo[3,2-c]pyridine-6-carboxylic acid hydrazide To a solution of 3,3-dimethyl-1-oxetan-3-yl-2-oxo-2,3-dihydro-1H-pyrrolo[3,2-c]pyridine-6 carboxylic acid methyl ester (0.50 g) in MeOH (10 ml) was added at 22° C. hydrazinehydrate (0.88 ml) and stirring was continued for 3 h. The mixture was evaporated and the residue partitioned between water and dichloromethane, the organic layer was dried, evaporated and the residue triturated with n-pentane to give the crude title compound (0.34 g, 68%) as a brown solid, which was used without further purification. MS (ESI, m/z): 276.8 [(M+H)$^+$].

d) 2-Methyl-isonicotinic acid N'-(3,3-dimethyl-1-oxetan-3-yl-2-oxo-2,3-dihydro-1H-pyrrolo[3,2-c]pyridine-6-carbonyl)-hydrazide To a solution of 2-methyl-isonicotinic acid (100 mg) and thionyl chloride (3.0 ml) was added DMF (0.05 ml) and stirring was continued at 80° C. for 4 h. The mixture was evaporated, the residue dissolved in dichloromethane (5 ml), then 3,3-dimethyl-1-oxetan-3-yl-2-oxo-2,3-dihydro-1H-pyrrolo[3,2-c]pyridine-6-carboxylic acid hydrazide (180 mg) was added at 22° C. followed by triethylamine (0.2 ml) and stirring was continued 12 h. The mixture was partitioned between aqueous sodium hydrogencarbonate and dichloromethane, the organic layer was dried, evaporated and the residue purified by flash chromatography (silica gel, dichloromethane/MeOH 99:1)) to give the title compound (100 mg, 35%) as a brown solid. MS (ESI, m/z): 396.0 [(M+H)$^+$].

e) 3,3-Dimethyl-6-[5-(2-methyl-pyridin-4-yl)-[1,3,4]oxadiazol-2-yl]-1-oxetan-3-yl-1,3-dihydro-pyrrolo[3,2-c]pyridin-2-one (Example 97)

Example 97 was prepared from 2-methyl-isonicotinic acid N'-(3,3-dimethyl-1-oxetan-3-yl-2-oxo-2,3-dihydro-1H- pyrrolo[3,2-c]pyridine-6-carbonyl)-hydrazide in analogy to example 11b to give the title compound (63%) as a white solid. MS (ESI, m/z): 378.3 [(M+H)⁺].

Example 98

6-(1-(2-Fluoro-5-methylpyridin-4-yl)-1H-imidazol-4-yl)-1,3,3-trimethylindolin-2-one

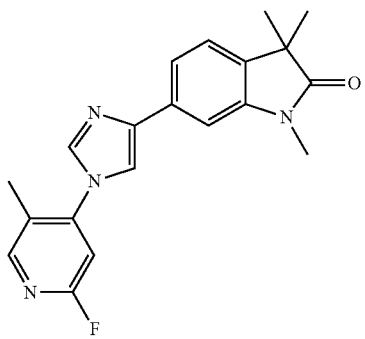 [SMILES: Cc1cnc(F)cc1-n1cnc(-c2ccc3c(c2)N(C)C(=O)C3(C)C)c1]

Example 98 was prepared from 6-(1H-imidazol-5-yl)-1,3,3-trimethylindolin-2-one from example 59d and 2-fluoro-4-iodo-5-methylpyridine in analogy to example 59e to give the title compound (12%) as a light yellow solid. MS (ESI, m/z): 351.2 [(M+H)⁺].

Example 99

6-(2-(2-Fluoro-5-methylpyridin-4-yl)oxazol-5-yl)-1,3,3-trimethylindolin-2-one

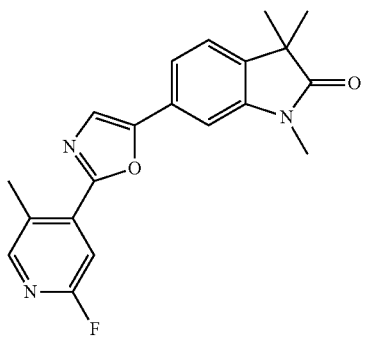 [SMILES: Cc1cnc(F)cc1-c1ncc(-c2ccc3c(c2)N(C)C(=O)C3(C)C)o1]

Example 99 was prepared from 6-(2-azidoacetyl)-1,3,3-trimethylindolin-2-one from example 96a and 2-fluoro-5-methylisonicotinoyl chloride in analogy to example 96b to give the title compound (21%) as a white solid. MS (ESI, m/z): 352.2 [(M+H)⁺].

Example 100

6-(5-(5-Fluoro-2-methylpyridin-4-yl)-1,3,4-oxadiazol-2-yl)-1,3,3-trimethylindolin-2-one

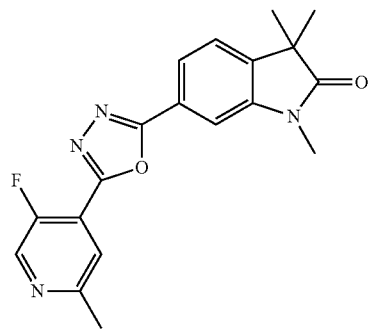 [SMILES: Cc1cc(-c2nnc(-c3ccc4c(c3)N(C)C(=O)C4(C)C)o2)c(F)cn1]

a) Methyl 1,3,3-trimethyl-2-oxoindoline-6-carboxylate

To a solution of methyl 2-oxoindoline-6-carboxylate (4.08 g) and MeI (6.12 g) in DMF (61 ml) was added at 22° C. NaH (1.71 g) over a period of 1.5 h and stirring was continued for 4 h. The mixture was partitioned between aqueous hydrochloric acid (1 M) and EtOAc, the organic layer was dried, evaporated and the residue purified by flash chromatography (silica gel, gradient, 0% to 100% EtOAc in n-heptane) to give the title compound (0.64 g, 13%) as a brown solid. MS (ESI, m/z): 234.5 [(M+H)⁺]. The second fraction contained 3,3-dimethyl-2-oxo-2,3-dihydro-1H-indole-6-carboxylic acid methyl ester (3.82 g, 82%) as brown solid. MS (ESI, m/z): 220.5 [(M+H)⁺].

b) 1,3,3-Trimethyl-2-oxoindoline-6-carbohydrazide

A solution of methyl 1,3,3-trimethyl-2-oxoindoline-6-carboxylate (350 mg) in methanol (4 ml) and hydrazine monohydrate (751 mg) was stirred at 22° C. for 20 h. The mixture was evaporated and the residue partitioned between water and dichloromethane, the organic layer was dried and evaporated to give the crude title compound (340 mg, 97%) as a white foam, which was used without further purification. MS (ESI, m/z): 234.1 [(M+H)⁺].

c) N'-(5-Fluoro-2-methylisonicotinoyl)-1,3,3-trimethyl-2-oxoindoline-6-carbohydrazide To a mixture of 5-fluoro-2-methylisonicotinic acid (200 mg) in dichloromethane (7 ml) and DMF (1 ml) was subsequently added at 22° C. EDCI (198 mg), HOBT (158 mg) and triethylamine (163 mg) and stirring was continued for 15 min. 1,3,3-Trimethyl-2-oxoindoline-6-carbohydrazide (165 mg) was added and stirring was continued for 18 h. The mixture was evaporated and the residue purified by flash chromatography (silica gel, gradient, 0% to 10% MeOH in dichloromethane) to give the title compound (186 mg, 62%) as yellow oil. MS (ESI, m/z): 371.1 [(M+H)⁺].

d) 6-(5-(5-Fluoro-2-methylpyridin-4-yl)-1,3,4-oxadiazol-2-yl)-1,3,3-trimethylindolin-2-one (Example 100)

Example 100 was prepared from N'-(5-fluoro-2-methylisonicotinoyl)-1,3,3-trimethyl-2-oxoindoline-6-carbohydrazide in analogy to example 11b to give the title compound (43%) as a white solid. MS (ESI, m/z): 353.1 [(M+H)+].

Example 101

1,3,3-Trimethyl-6-(2-(6-methylpyridin-3-yl)pyrimidin-5-yl)indolin-2-one

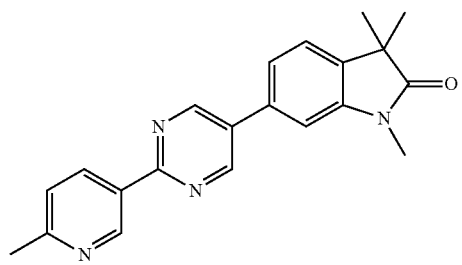 [SMILES: Cc1ccc(-c2ncc(-c3ccc4c(c3)N(C)C(=O)C4(C)C)cn2)cn1]

a) 6-(2-Chloropyrimidin-5-yl)-1,3,3-trimethylindolin-2-one

Example 101a was prepared from 1,3,3-trimethyl-6-(4,4,5,5-tetramethyl-1,3,2-dioxaborolan-2-yl)indolin-2-one from example 82a and 5-bromo-2-chloropyrimidine in analogy to example 82b to give the title compound as white solid (195 mg, 58%). MS (ESI, m/z): 288.5 [(M+H)+].

b) 1,3,3-Trimethyl-6-(2-(6-methylpyridin-3-yl)pyrimidin-5-yl)indolin-2-one (Example 101)

Example 101 was prepared from 6-(2-chloropyrimidin-5-yl)-1,3,3-trimethylindolin-2-one and 6-methylpyridin-3-yl-boronic acid in analogy to example 82c to give the title compound as white solid (85 mg 64%). MS (ESI, m/z): 345.5 [(M+H)+].

Example 102

6-[1-(3-Fluoro-4-pyridyl)imidazol-4-yl]-3,3-dimethyl-1-(6-methyl-3-pyridyl)indolin-2-one

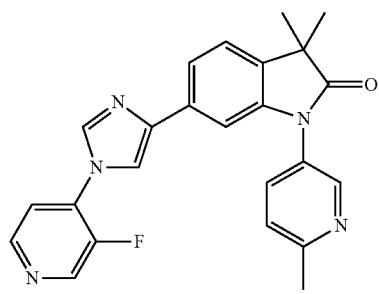 [SMILES: Cc1ccc(N2C(=O)C(C)(C)c3ccc(-c4cn(-c5ccncc5F)cn4)cc32)cn1]

a) 6-(1H-Imidazol-4-yl)-1-(4-methoxybenzyl)-3,3-dimethylindolin-2-one

Example 102a was prepared from 6-bromo-1-(4-methoxybenzyl)-3,3-dimethylindolin-2-one (example 25a) in analogy to example 3a-b, 92b. The title compound was obtained as brown semi solid and was used without further purification. MS (ESI, m/z): 348.3 [(M+H)+].

b) 6-[1-(3-Fluoro-4-pyridyl)imidazol-4-yl]-3,3-dimethyl-indolin-2-one

Example 102b was prepared from 6-(1H-imidazol-4-yl)-1-(4-methoxybenzyl)-3,3-dimethylindolin-2-one in analogy to example 92c (using 3,4-difluoropyridine) and 63 h. The title compound was obtained as off white solid. MS (ESI, m/z): 321.1 [(M+H)+].

c) 6-[1-(3-Fluoro-4-pyridyl)imidazol-4-yl]-3,3-dimethyl-1-(6-methyl-3-pyridyl)indolin-2-one (Example 102)

To a stirred solution of 6-[1-(3-fluoro-4-pyridyl)imidazol-4-yl]-3,3-dimethyl-indolin-2-one (150 mg) in acetonitrile (10 ml) were added potassium carbonate (141.4 mg) and 5-bromo-2-methyl-pyridine (96.7 mg). The apparatus was evacuated and flushed with argon 3 times. The resulting mixture was stirred at room temperature for ~2 minutes. Then the mixture was sparged with argon for 10 minutes, CuI (10.0 mg) and N,N'-dimethylethylen-1,2-diamine (13.1 mg) were added and sparging continued for 10 minutes. Then the reaction mixture was heated to 110° C. for 5 hours. The reaction was poured into ice water and ethyl acetate. The layers were separated and the aqueous layer extracted with ethyl acetate. The combined organic layers were dried over sodium sulfate, filtered and concentrated under vacuum and the residue purified by flash column chromatography (silica gel, 0% to 10% MeOH in ethyl acetate). The title compound was obtained as off white solid (60 mg, 31%). MS (ESI, m/z): 414.2 [(M+H)+].

Example 103

6-[1-(3-fluoro-4-pyridyl)imidazol-4-yl]-3,3-dimethyl-1-(2-methyl-4-pyridyl)indolin-2-one

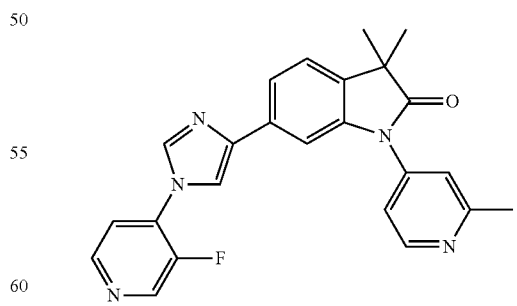

Example 103 was prepared in analogy to example 102 using 3,4-difluoropyridine for imidazole arylation and 4-bromo-2-methylpyridine for lactam arylation. The title compound was obtained as white solid (70 mg). MS (ESI, m/z): 414.4 [(M+H)+].

Example 104

3,3-Dimethyl-1-(6-methyl-3-pyridyl)-6-[1-(2-methyl-4-pyridyl)imidazol-4-yl]indolin-2-one

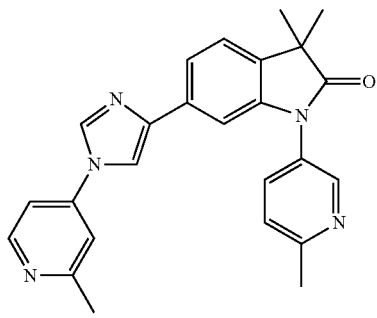 [SMILES: Cc1ccc(N2C(=O)C(C)(C)c3ccc(-c4cn(-c5ccnc(C)c5)cn4)cc32)cn1]

Example 104 was prepared in analogy to example 102 using 4-fluoro-2-methylpyridine for imidazole arylation and 5-bromo-2-methyl-pyridine for lactam arylation. The title compound was obtained as yellow solid (60 mg). MS (ESI, m/z): 410.0 [(M+H)$^+$].

Example 105

3,3-Dimethyl-1-(6-methyl-3-pyridyl)-6-[1-(3-methyl-4-pyridyl)imidazol-4-yl]indolin-2-one

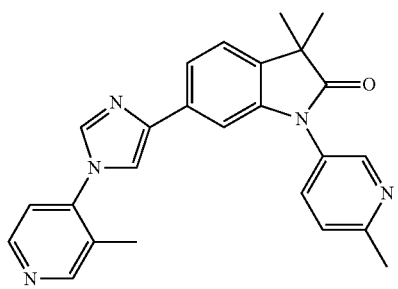 [SMILES: Cc1ccc(N2C(=O)C(C)(C)c3ccc(-c4cn(-c5ccncc5C)cn4)cc32)cn1]

Example 105 was prepared in analogy to example 102 using 4-fluoro-3-methylpyridine for imidazole arylation and 5-bromo-2-methyl-pyridine for lactam arylation. The title compound was obtained as off white solid (55 mg). MS (ESI, m/z): 409.9 [(M+H)$^+$].

Example 106

3,3-Dimethyl-1-(2-methyl-4-pyridyl)-6-[1-(3-methyl-4-pyridyl)imidazol-4-yl]indolin-2-one

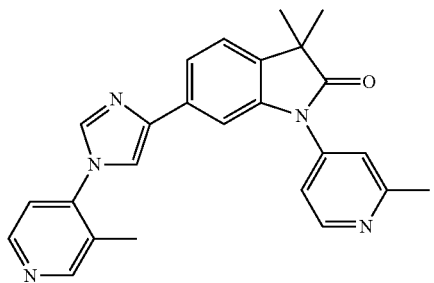 [SMILES: Cc1cc(N2C(=O)C(C)(C)c3ccc(-c4cn(-c5ccncc5C)cn4)cc32)ccn1]

Example 106 was prepared in analogy to example 102 using 4-fluoro-3-methylpyridine for imidazole arylation and 4-bromo-2-methyl-pyridine for lactam arylation. The title compound was obtained as off white solid (52 mg). MS (ESI, m/z): 410.0 [(M+H)$^+$].

Example 107

3,3-Dimethyl-1-(2-methylpyridin-4-yl)-6-(1-(2-methylpyridin-4-yl)-1H-imidazol-4-yl)indolin-2-one

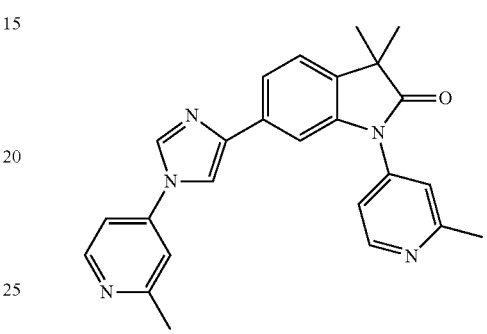

Example 107 was prepared in analogy to example 102 using 4-fluoro-2-methylpyridine for imidazole arylation and 4-bromo-2-methyl-pyridine for lactam arylation. The title compound was obtained as colorless amorphous solid (35 mg). MS (ESI, m/z): 410.2 [(M+H)$^+$].

Example 108

6-(1-(3-Fluoropyridin-4-yl)-1H-imidazol-4-yl)-3,3-dimethyl-1-(1-methyl-1H-imidazol-4-yl)indolin-2-one

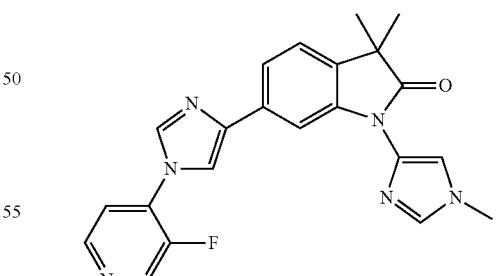

Example 108 was prepared in analogy to example 102 using 3,4-difluoropyridine for imidazole arylation and 4-bromo-1-methyl-1H-imidazole for lactam arylation. The title compound was obtained as brown amorphous solid (25 mg). MS (ESI, m/z): 403.2 [(M+H)$^+$].

Example 109

6-(1-(3-Fluoropyridin-4-yl)-1H-imidazol-4-yl)-3,3-dimethyl-1-(1-methyl-1H-pyrazol-3-yl)indolin-2-one

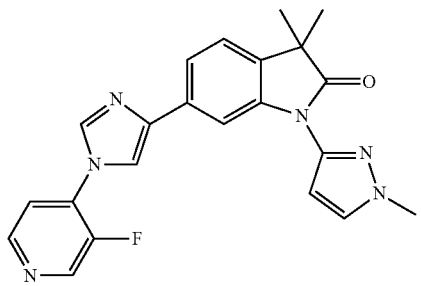 [SMILES: Cn1ccc(N2C(=O)C(C)(C)c3ccc(-c4cn(-c5ccncc5F)cn4)cc32)n1]

Example 109 was prepared in analogy to example 102 using 3,4-difluoropyridine for imidazole arylation and 3-bromo-1-methyl-1H-pyrazole for lactam arylation. The title compound was obtained as off white solid (18 mg). MS (ESI, m/z): 403.2 [(M+H)$^+$].

Example 110

6-[1-(3-Fluoro-4-pyridyl)imidazol-4-yl]-3,3-dimethyl-1-(2-methylpyrimidin-5-yl)indolin-2-one

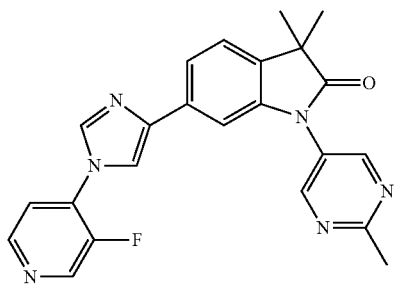

Example 110 was prepared in analogy to example 102 using 3,4-difluoropyridine for imidazole arylation and 5-bromo-2-methyl-pyrimidine for lactam arylation The title compound was obtained as light brown solid (65 mg). MS (ESI, m/z): 415.2 [(M+H)$^+$].

Example 111

3,3-Dimethyl-1-(1-methylimidazol-4-yl)-6-[1-(2-methyl-4-pyridyl)imidazol-4-yl]indolin-2-one

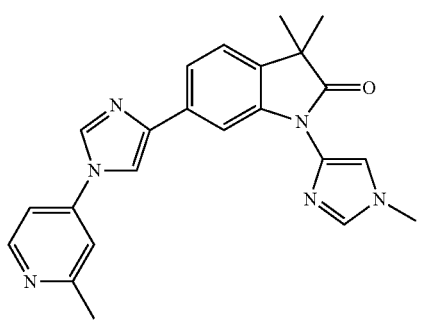 [SMILES: Cc1cc(-n2cnc(-c3ccc4c(c3)N(c3cn(C)cn3)C(=O)C4(C)C)c2)ccn1]

Example 111 was prepared in analogy to example 102 using 4-fluoro-2-methylpyridine for imidazole arylation and 4-bromo-1-methyl-1H-imidazole for lactam arylation The title compound was obtained as light yellow solid (60 mg). MS (ESI, m/z): 399.0 [(M+H)$^+$].

Example 112

3,3-Dimethyl-1-(1-methylpyrazol-3-yl)-6-[1-(2-methyl-4-pyridyl)imidazol-4-yl]indolin-2-one

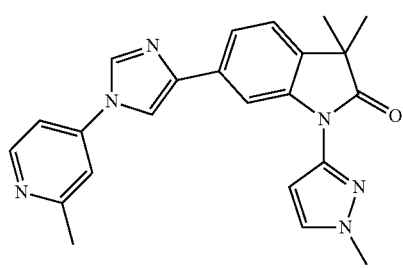 [SMILES: Cc1cc(-n2cnc(-c3ccc4c(c3)N(c3ccn(C)n3)C(=O)C4(C)C)c2)ccn1]

Example 112 was prepared in analogy to example 102 using 4-fluoro-2-methylpyridine for imidazole arylation and 3-bromo-1-methyl-1H-pyrazole for lactam arylation The title compound was obtained as orange solid (50 mg). MS (ESI, m/z): 399.4 [(M+H)$^+$].

Example 113

3,3-Dimethyl-6-[1-(2-methyl-4-pyridyl)imidazol-4-yl]-1-(2-methylpyrimidin-5-yl)indolin-2-one

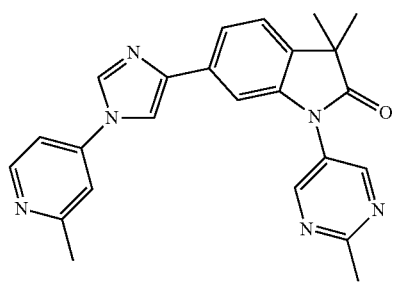 [SMILES: Cc1cc(-n2cnc(-c3ccc4c(c3)N(c3cnc(C)nc3)C(=O)C4(C)C)c2)ccn1]

Example 113 was prepared in analogy to example 102 using 4-fluoro-2-methylpyridine for imidazole arylation and 5-bromo-2-methyl-pyrimidine for lactam arylation The title compound was obtained as light yellow solid (50 mg). MS (ESI, m/z): 411.3 [(M+H)$^+$].

Example 114

3,3-Dimethyl-1-(1-methylimidazol-4-yl)-6-[1-(3-methyl-4-pyridyl)imidazol-4-yl]indolin-2-one

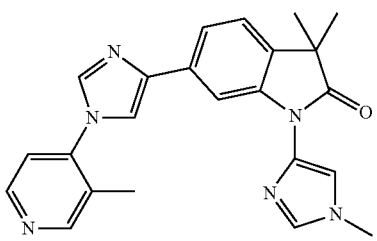 [SMILES: Cc1cnccc1-n1cnc(-c2ccc3c(c2)N(c2cn(C)cn2)C(=O)C3(C)C)c1]

Example 114 was prepared in analogy to example 102 using 4-fluoro-3-methylpyridine for imidazole arylation and 4-bromo-1-methyl-1H-imidazole for lactam arylation The title compound was obtained as off white solid (45 mg). MS (ESI, m/z): 399.4 [(M+H)$^+$].

Example 115

3,3-Dimethyl-1-(1-methylpyrazol-3-yl)-6-[1-(3-methyl-4-pyridyl)imidazol-4-yl]indolin-2-one

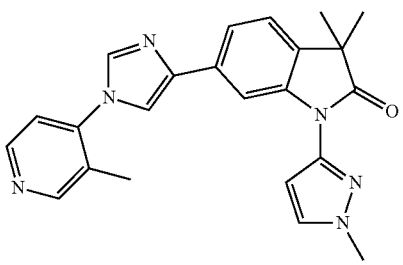 [SMILES: Cc1cnccc1-n1cnc(-c2ccc3c(c2)N(c2ccn(C)n2)C(=O)C3(C)C)c1]

Example 115 was prepared in analogy to example 102 using 4-fluoro-3-methylpyridine for imidazole arylation and 3-bromo-1-methyl-1H-pyrazole for lactam arylation The title compound was obtained as off white solid (45 mg). MS (ESI, m/z): 399.2 [(M+H)$^+$].

Example 116

3,3-Dimethyl-6-[1-(3-methyl-4-pyridyl)imidazol-4-yl]-1-(2-methylpyrimidin-5-yl)indolin-2-one

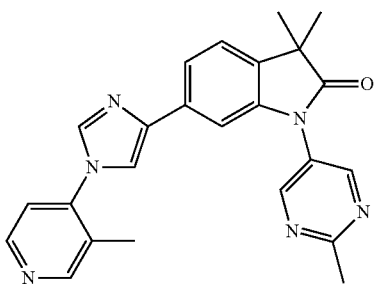 [SMILES: Cc1ncc(N2C(=O)C(C)(C)c3ccc(-c4cn(-c5ccncc5C)cn4)cc32)cn1]

Example 116 was prepared in analogy to example 102 using 4-fluoro-3-methylpyridine for imidazole arylation and 5-bromo-2-methyl-pyrimidine for lactam arylation The title compound was obtained as orange solid (70 mg). MS (ESI, m/z): 399.2 [(M+H)$^+$].

Example 117

1-Cyclopropyl-3,3-dimethyl-6-(1-(2-methylpyrimidin-5-yl)-1H-imidazol-4-yl)indolin-2-one

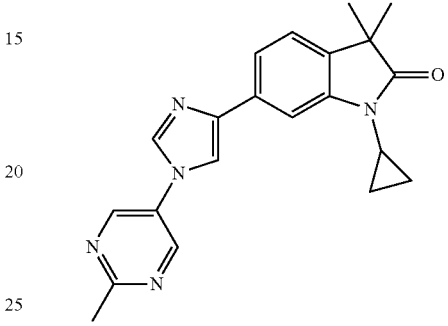

Example 117 was prepared from 1-cyclopropyl-6-(1H-imidazol-5-yl)-3,3-dimethylindolin-2-one from example 71a in analogy to example 59e using 5-bromo-2-methylpyrimidine. The title compound was obtained as brown solid (164 mg, 81%). MS (ESI, m/z): 360.2 [(M+H)$^+$].

Example 118

1-Cyclopropyl-3,3-dimethyl-6-(1-(5-methylpyrimidin-2-yl)-1H-imidazol-4-yl)indolin-2-one

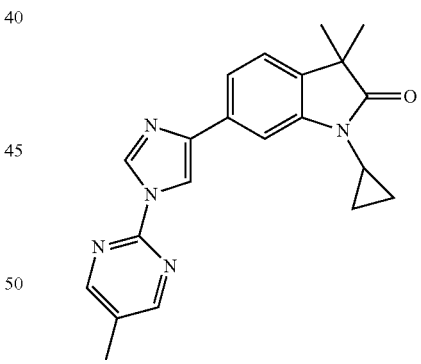

In a sealed glass tube a suspension of 1-cyclopropyl-6-(1H-imidazol-5-yl)-3,3-dimethylindolin-2-one (example 71a, 70 mg), 2-chloro-5-methylpyrimidine (37.0 mg) and cesium carbonate (158 mg) in acetonitrile (1.05 ml) was heated to 120° C. for 30 minutes under microwave irradiation. Then again 18 mg 2-chloro-5-methylpyrimidine and 89 mg cesium carbonate were added and the reaction mixture heated to 120° C. under conventional heating for 2 hours. The reaction mixture was concentrated in vacuo and purified by flash chromatography (silica gel, gradient, 0% to 100% EtOAc in n-heptane). The title compound was obtained as off white solid (75 mg, 80%). MS (ESI, m/z): 360.2 [(M+H)+].

Example 119

1,3,3-Trimethyl-6-(1-(5-methylpyrimidin-2-yl)-1H-imidazol-4-yl)indolin-2-one

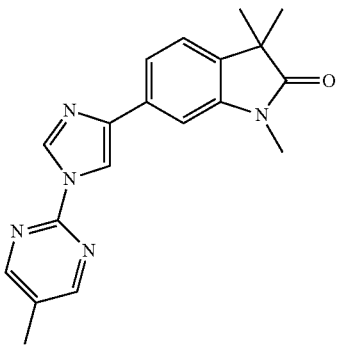 [SMILES: Cc1cnc(-n2cnc(-c3ccc4c(c3)N(C)C(=O)C4(C)C)c2)nc1]

Example 119 was prepared from 6-(1H-imidazol-5-yl)-1,3,3-trimethylindolin-2-one from example 59d in analogy to example 118. The title compound was obtained as white solid (71 mg, 86%). MS (ESI, m/z): 334.2 [(M+H)+].

Example 120

1,3,3-Trimethyl-6-(1-(2-methylpyrimidin-5-yl)-1H-imidazol-4-yl)indolin-2-one

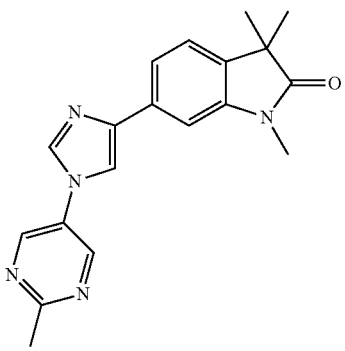 [SMILES: Cc1ncc(-n2cnc(-c3ccc4c(c3)N(C)C(=O)C4(C)C)c2)cn1]

Example 120 was prepared from 6-(1H-imidazol-5-yl)-1,3,3-trimethylindolin-2-one from example 59d in analogy to example 59e using 5-bromo-2-methylpyrimidine. The title compound was obtained as white solid (109 mg, 53%). MS (ESI, m/z): 334.2 [(M+H)+].

Example 121

3,3-Dimethyl-6-(1-(2-methylpyrimidin-5-yl)-1H-imidazol-4-yl)indolin-2-one

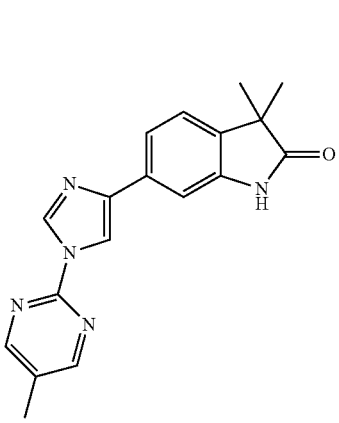 [SMILES: Cc1cnc(-n2cnc(-c3ccc4c(c3)NC(=O)C4(C)C)c2)nc1]

Example 121 was prepared from 6-(1H-imidazol-4-yl)-1-(4-methoxybenzyl)-3,3-dimethylindolin-2-one (example 102a) in analogy to example 59e (using 5-bromo-2-methylpyrimidine) and example 63h. The title compound was obtained as light yellow solid (27 mg). MS (ESI, m/z): 320.2 [(M+H)+].

Example 122

3,3-Dimethyl-6-(1-(5-methylpyrimidin-2-yl)-1H-imidazol-4-yl)indolin-2-one

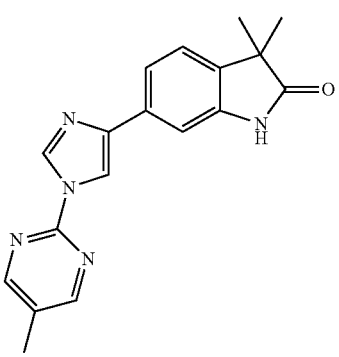 [SMILES: Cc1cnc(-n2cnc(-c3ccc4c(c3)NC(=O)C4(C)C)c2)nc1]

Example 122 was prepared from 6-(1H-imidazol-4-yl)-1-(4-methoxybenzyl)-3,3-dimethylindolin-2-one from example 102a in analogy to example 118 and 63 h. The title compound was obtained as light yellow solid (30 mg). MS (ESI, m/z): 320.2 [(M+H)+].

Example 123

3,3-Dimethyl-6-(1-(6-methylpyridin-2-yl)-1H-imidazol-4-yl)indolin-2-one

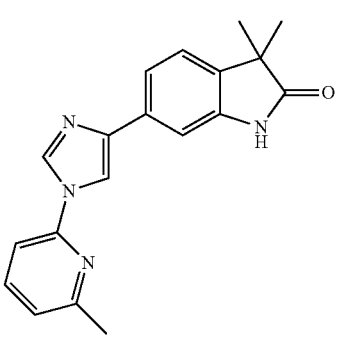 [SMILES: Cc1cccc(-n2cnc(-c3ccc4c(c3)NC(=O)C4(C)C)c2)n1]

Example 123 was prepared in analogy to example 102a-b using 2-fluoro-6-methylpyridine for the imidazole arylation. The title compound was obtained as light yellow solid (41 mg). MS (ESI, m/z): 319.2 [(M+H)+].

Example 124

6-[4-(5-Fluoro-2-methyl-4-pyridyl)imidazol-1-yl]-1,3,3-trimethyl-indolin-2-one

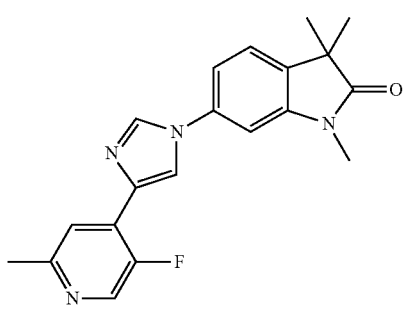 [SMILES: Cc1cc(-c2cn(-c3ccc4c(c3)N(C)C(=O)C4(C)C)cn2)c(F)cn1]

a) 6-(4-Bromoimidazol-1-yl)-1,3,3-trimethyl-indolin-2-one

To a stirred solution of 6-Bromo-1,3,3-trimethylindolin-2-one (example 2a, 1 g) in NMP (9 ml) were added 4-bromo-1H-imidazole (0.578 g), potassium carbonate (1.71 g) and 2-acetylcyclohexanone (0.26 ml) and the mixture was sparged with argon for 15 minutes. Then CuCl (0.08 g) was added to the mixture and sparging was continued for another 10 minutes. The reaction vessel was sealed and the reaction then heated to 130° C. for 14 hours. The reaction mixture was diluted with water and extracted with ethyl acetate. The combined organic layers were washed with water followed by brine. The organic layer was dried with sodium sulfate and concentrated under vacuum. The crude material was purified by flash chromatography (silica gel, gradient 0-30% ethyl acetate in hexane). The title compound was obtained as off white solid (300 mg, 42%). MS (ESI, m/z): 320.1 [(M+H)$^+$].

b) 6-[4-(5-Fluoro-2-methyl-4-pyridyl)imidazol-1-yl]-1,3,3-trimethyl-indolin-2-one (Example 124)

In a microwave vessel to a stirred solution of 6-(4-Bromoimidazol-1-yl)-1,3,3-trimethyl-indolin-2-one (100 mg) in a mixture of DME (3 ml) and water (0.8 ml) were added 5-fluoro-2-methyl-4-(tetramethyl-1,3,2-dioxaborolan-2-yl)pyridine (111 mg) and potassium carbonate (259 mg). The reaction mixture was sparged with argon for 15 minutes. Then PdCl$_2$(PPh$_3$)$_2$ (11 mg) was then added to the reaction mixture and sparging was continued for another 10 minutes. The reaction mixture heated to 130° C. for 30 minutes under microwave irradiation. The resulting suspension was filtered and the filtrate was concentrated under vacuum. The crude material was purified by flash chromatography (silica gel, gradient 70-80% ethyl acetate in hexane) followed by purification using preparative TLC using ethyl acetate as the mobile phase. The title compound was obtained as off white solid (22 mg, 26%). MS (ESI, m/z): 350.9 [(M+H)$^+$].

Example 125

1,3,3-Trimethyl-6-[5-(3-methyl-4-pyridyl)isoxazol-3-yl]indolin-2-one

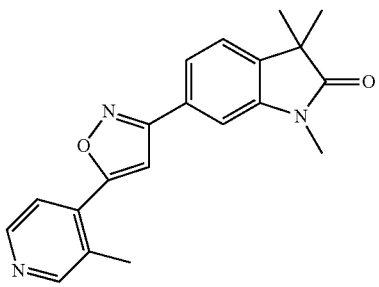 [SMILES: Cc1cnccc1-c1cc(-c2ccc3c(c2)N(C)C(=O)C3(C)C)no1]

a) 1-(3-Methyl-4-pyridyl)-3-(1,3,3-trimethyl-2-oxo-indolin-6-yl)propane-1,3-dione To a stirred solution of 6-acetyl-1,3,3-trimethyl-2,3-dihydro-1H-indol-2-one (example 3a, 100 mg) in THF (2 ml) was added NaH (60% in oil, 39 mg) at 0° C. and stirred for 30 minutes at room temperature. Then methyl 3-methylpyridine-4-carboxylate (63 mg) in THF (1 ml) was added and stirring at room temperature continued for 21 hours. Then the reaction mixture was heated for 1 hour to 50° C. The reaction mixture was quenched with aqueous saturated ammonium chloride solution and extracted with EtOAc. The combined organic layers were washed with brine, dried over anhydrous sodium sulfate and concentrated under vacuum. The crude material was purified by flash chromatography (silica gel, EtOAc in n-hexane 20%). The title compound was obtained as off white solid (60 mg, 52% based on recovered starting material). MS (ESI, m/z): 337.0 [(M+H)$^+$].

b) 1,3,3-trimethyl-6-[5-(3-methyl-4-pyridyl)isoxazol-3-yl]indolin-2-one (Example 125)

Example 125 was prepared from 1-(3-methyl-4-pyridyl)-3-(1,3,3-trimethyl-2-oxo-indolin-6-yl)propane-1,3-dione in analogy to example 42a. The title compound was obtained as off white solid (45 mg, 46%). Only the given isomer was obtained. MS (ESI, m/z): 334.1 [(M+H)$^+$].

Example 126

1,3,3-Trimethyl-6-[4-(3-methyl-4-pyridyl)imidazol-1-yl]indolin-2-one

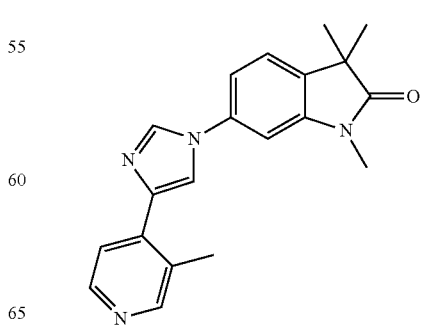

In a microwave vessel to a stirred solution of 6-(4-bromoimidazol-1-yl)-1,3,3-trimethyl-indolin-2-one (example 124a, 500 mg) in dioxane (5 ml) were added (3-methyl-4-pyridyl)boronic acid (256 mg) and NaOtBu (180 mg) and the mixture sparged with argon. Then Brettphos (84 mg) and Brettphos palladacycle (125 mg) were added and again sparged with argon. The reaction mixture was heated to 130° C. under microwave irradiation for 1 hour. Then the reaction mixture was cooled to room temperature, filtered and concentrated under vacuum. The crude material was purified by flash chromatography (80% ethyl acetate in hexane). The title compound was obtained as off white solid (21.6 mg, 10% based on recovered starting material). MS (ESI, m/z): 333.1 [(M+H)$^+$].

Example 127

1,3,3-Trimethyl-6-[4-(2-methyl-4-pyridyl)imidazol-1-yl]indolin-2-one

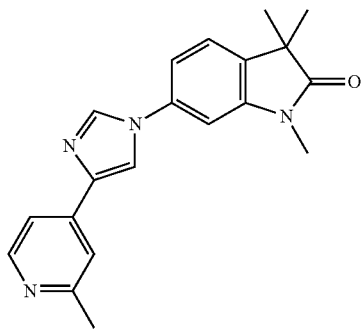 [SMILES: Cc1cc(-c2cn(-c3ccc4c(c3)N(C)C(=O)C4(C)C)cn2)ccn1]

Example 127 was prepared in analogy to example 126. The title compound was obtained as off white solid (20 mg, 9%). MS (ESI, m/z): 333.3 [(M+H)$^+$].

Example 128

6-[4-(2-Fluoro-4-pyridyl)imidazol-1-yl]-1,3,3-trimethyl-indolin-2-one

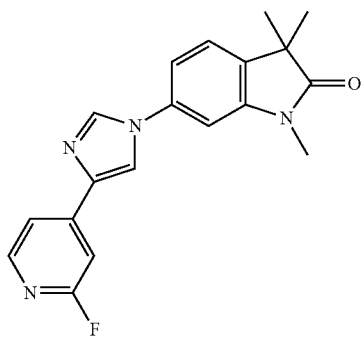 [SMILES: CN1C(=O)C(C)(C)c2ccc(-n3cnc(-c4ccnc(F)c4)c3)cc21]

Example 128 was prepared in analogy to example 126. The title compound was obtained as off white solid (8 mg, 14%). MS (ESI, m/z): 337.2 [(M+H)$^+$].

Example 129

1-(3-Cyclopropylsulfonylpropyl)-6-[1-(3-fluoro-4-pyridyl)imidazol-4-yl]-3,3-dimethyl-indolin-2-one

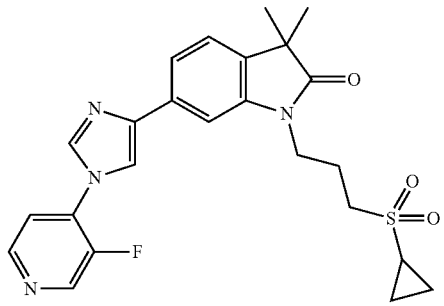 [SMILES: CC1(C)C(=O)N(CCCS(=O)(=O)C2CC2)c2cc(-c3cn(-c4ccncc4F)cn3)ccc21]

a) 6-Bromo-1-(3-cyclopropylsulfonylpropyl)-3,3-dimethyl-indolin-2-one

Example 129a was prepared from 6-bromo-3,3-dimethyl-indolin-2-one (example 1a) in analogy to WO2014/40969 A1, examples 65b and 70e. The title compound was obtained as off white solid (1.01 g). MS (ESI, m/z): 385.8, 387.8 [(M+H)$^+$].

b) 1-(3-Cyclopropylsulfonylpropyl)-6-(1H-imidazol-4-yl)-3,3-dimethyl-indolin-2-one Example 129b was prepared in analogy to example 3a-b and 92b. The title compound was obtained as brown solid (0.6 g). MS (ESI, m/z): 374.1 [(M+H)$^+$].

c) 1-(3-Cyclopropylsulfonylpropyl)-6-[1-(3-fluoro-4-pyridyl)imidazol-4-yl]-3,3-dimethyl-indolin-2-one (Example 129)

Example 129 was prepared in analogy to example 92c using 3,4-difluoropyridine. The title compound was obtained as brown sticky solid (22 mg, 18%). MS (ESI, m/z): 469.3 [(M+H)$^+$].

Example 130

6-[1-(3-Fluoro-4-pyridyl)imidazol-4-yl]-1-(2-hydroxyethyl)-3,3-dimethyl-indolin-2-one

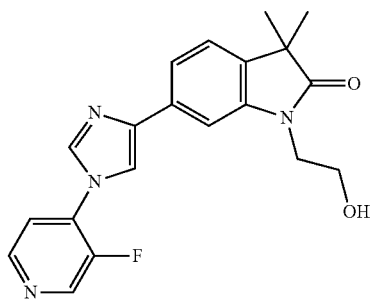 [SMILES: CC1(C)C(=O)N(CCO)c2cc(-c3cn(-c4ccncc4F)cn3)ccc21]

a) (2-Bromoethoxy)(tert-butyl)dimethylsilane

To a stirred solution of TBDMSCl (3.5 g) in DMF (10 ml) was added imidazole (1.77 g). Then 2-bromoethan-1-ol (2.5 g) was added slowly dropwise and the reaction mixture was stirred at room temperature for 16 hours. The reaction was quenched with water and extracted with hexane. The combined organic layers were dried over anhydrous sodium sulfate and concentrated under reduced pressure. The crude material was purified by flash chromatography (silica gel, gradient 0-3% ethyl acetate in hexane). The title compound was obtained as colourless oil (3.96 g, 83%). NMR complied with literature data.

b) 1-[2-[tert-Butyl(dimethyl)silyl]oxyethyl]-6-[1-(3-fluoro-4-pyridyl)imidazol-4-yl]-3,3-dimethyl-indolin-2-one To a solution of compound 6-[1-(3-gluoro-4-pyridyl)imidazol-4-yl]-3,3-dimethyl-indolin-2-one (example 102b, 430 mg) in DMF (3 ml) was added $Cs_2CO_3$ (869.3 mg) and a solution of 2-(2-bromoethoxy)(tert-butyl)dimethylsilane (638.3 mg) in DMF (2 ml). The tube was sealed and the reaction mixture heated to 70° C. for 5 hours. The reaction mixture was poured into ice water and ethyl acetate. The layers were separated and the aqueous layer extracted with ethyl acetate. The combined organic layers were washed with water, dried over anhydrous sodium sulfate and concentrated under reduced pressure. The crude material was purified by flash chromatography (silica gel, gradient 0-50% EtOAc in hexane). The title compound was obtained as brown solid (260 mg, 33%). MS (ESI, m/z): 481.0 [(M+H)$^+$].

c) 6-[1-(3-Fluoro-4-pyridyl)imidazol-4-yl]-1-(2-hydroxyethyl)-3,3-dimethyl-indolin-2-one (Example 130)

To a solution of 1-[2-[tert-Butyl(dimethyl)silyl]oxyethyl]-6-[1-(3-fluoro-4-pyridyl)imidazol-4-yl]-3,3-dimethyl-indolin-2-one (250 mg) in THF (10 ml) was added TBAF solution (1 M in THF, 0.5 ml) at 0° C. After 15 minutes the reaction mixture was allowed to reach room temperature and was stirred for 3 hours. The reaction mixture was diluted with water (30 ml) and extracted with ethyl acetate. The combined organic layers were dried over anhydrous sodium sulfate and concentrated under reduced pressure. The crude material was purified by flash chromatography (silica gel, gradient 0-3% methanol in dichloromethane). The title compound was obtained as off white solid (71 mg, 37%). MS (ESI, m/z): 367.3 [(M+H)$^+$].

Example 131

1-(3-Cyclopropylsulfonylpropyl)-6-[1-(5-fluoro-2-methyl-4-pyridyl)imidazol-4-yl]-3,3-dimethyl-indolin-2-one

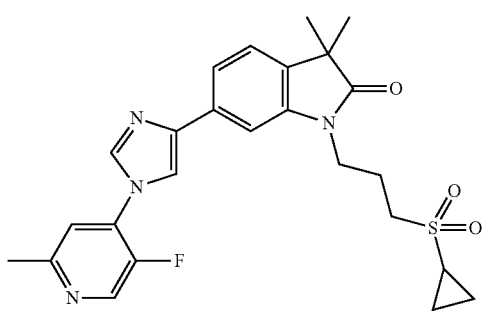 [SMILES: Cc1cc(-n2cnc(-c3ccc4c(c3)N(CCCS(=O)(=O)C3CC3)C(=O)C4(C)C)c2)c(F)cn1]

In a sealed tube to a mixture of 4-bromo-5-fluoro-2-methylpyridine (66 mg), CsF (106 mg) and tetramethylammonium fluoride (5 mg) in DMSO (1 ml) was heated to 120° C. for 24 hours. Then the reaction mixture was cooled to room temperature, 1-(3-cyclopropylsulfonylpropyl)-6-(1H-imidazol-4-yl)-3,3-dimethyl-indolin-2-one (example 129b, 100 mg) and $Cs_2CO_3$ (131 mg) were added, the tube resealed and the reaction mixture heated to 50° C. for 12 hours. The reaction mixture was diluted with water and extracted with ethyl acetate. The combined organic layers were washed with water and brine, dried over anhydrous sodium sulfate and concentrated under vacuum. The crude material was purified by flash chromatography (silica gel, gradient 0-80% ethyl acetate in hexane) followed by purification by preparative TLC. The title compound was obtained as white solid (31 mg, 16%). MS (ESI, m/z): 483.1 [(M+H)$^+$].

Example 132

6-[1-(5-Fluoro-2-methyl-4-pyridyl)imidazol-4-yl]-3,3-dimethyl-indolin-2-one trifluoroacetate

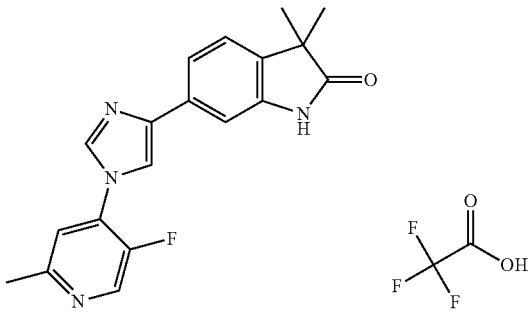 [SMILES: Cc1cc(-n2cnc(-c3ccc4c(c3)NC(=O)C4(C)C)c2)c(F)cn1 ; O=C(O)C(F)(F)F]

a) 6-[1-(5-Fluoro-2-methyl-4-pyridyl)imidazol-4-yl]-1-[(4-methoxyphenyl)methyl]-3,3-dimethyl-indolin-2-one Example 132a was prepared in analogy to example 131 from 6-(1H-imidazol-4-yl)-1-(4-methoxybenzyl)-3,3-dimethylindolin-2-one from example 102a. The title compound was obtained as brown solid (57 mg, 31%). MS (ESI, m/z): 457.0 [(M+H)$^+$].

b) 6-[1-(5-Fluoro-2-methyl-4-pyridyl)imidazol-4-yl]-3,3-dimethyl-indolin-2-one trifluoroacetate

Example 132

In a sealed tube a solution of 6-[1-(5-fluoro-2-methyl-4-pyridyl)imidazol-4-yl]-1-[(4-methoxyphenyl)methyl]-3,3-dimethyl-indolin-2-one (50 mg) in TFA (3 ml) was heated to 110° C. for 48 hours. The reaction mixture was concentrated in vacuo and the residue triturated with ether and pentante to afford the title compound as green sticky solid. MS (ESI, m/z): 337.1 [(M+H)$^+$].

Biological Assays and Data

Now it has been found that the compounds of formula I may be used for the treatment of CNS diseases.

The described compounds of formula I reduce L-687,414-induced hyperlocomotion. This was assessed by using a computerized Digiscan 16 Animal Activity Monitoring System (Omnitech Electronics, Columbus, Ohio) to quantify locomotor activity. Animals were kept under a 12 h light/dark cycle and experiments were performed during the light period. Each activity monitoring chamber consisted of a Plexiglas box (41×41×28 cm; W×L×H) with sawdust bedding on the floor surrounded by invisible horizontal and vertical infrared sensor beams. The test boxes were divided by a Plexiglas cross providing each mouse with 20×20 cm of moving space. Cages were connected to a Digi scan Analyzer linked to a computer that constantly collected the beam status information. Records of photocell beam interruptions for individual animals were taken every 5 min over the duration of the experimental session and the sum of the first 6 periods was used as the final parameter. Compounds were administered either p.o. 15 min before a s.c. injection of 50 mg/kg of L-687,414, or i.p. at the same time as a s.c. injection of 50 mg/kg of L-687,414. Mice were then transferred from their home cage to the recording chambers for a 15-min habituation phase allowing free exploration of the new environment. Horizontal activity was then recorded for a 30-min time period. The % inhibition of L-687,414-induced hyperlocomotion was calculated according to the equation:

((*Veh*+L-687,414 horizontal activity−drug+L-687,414 horizontal activity)/*Veh*+L-687,414 horizontal activity)×100

$ID_{50}$ values, defined as doses of each compound producing 50% inhibition of L-687,414-induced hyperlocomotion, were calculated by linear regression analysis of a dose-response data using an Excel-based computer-fitting program.

As data was not presupposed to be normally distributed, groups treated with test compounds were statistically compared with the control (vehicle-treated) group using one-tailed Mann Whitney U tests. In statistics, the Mann-Whitney Utest (also called the Mann-Whitney-Wilcoxon (MWW) or Wilcoxon rank-sum test) is a non-parametric statistical hypothesis test for assessing whether one of two samples of independent observations tends to have larger values than the other. It is one of the most well-known non-parametric significance tests. A p value gives the probability that two groups are significantly different from each other and the value of <0.05 is generally accepted as a criterion, it implies that there is >95% chance that two groups are really different from each other. P values given in table 1 are one-tailed since only decreases in locomotion were expected and tested for (Mann, H. B., Whitney, D. R. (1947), "On a Test of Whether one of Two Random Variables is Stochastically Larger than the Other", Annals of Mathematical Statistics, 18 (1), 50-60).

TABLE 1

Effects of compounds of formula I on L-687,414-induced hyperlocomotion

| Expl. | structure | Doses po [mg/kg] | $ID_{50}$ po [mg/kg] | Lowest P value | Dose ip [mg/kg] | Inhibition, ip [%] | P value |
|---|---|---|---|---|---|---|---|
| 2 | 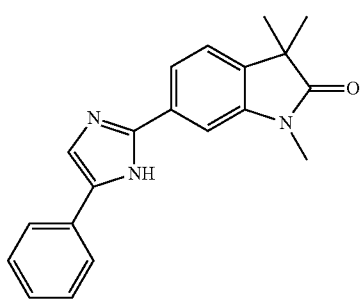 [SMILES: CN1C(=O)C(C)(C)c2ccc(-c3ncc(-c4ccccc4)[nH]3)cc21] | 3-10-30 | 10.71 | 0.00131 | | | |
| 3 | 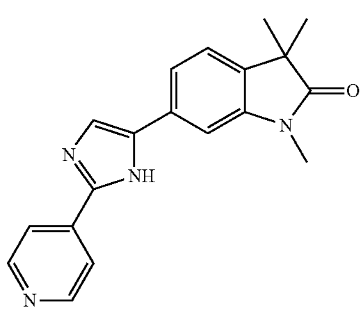 [SMILES: CN1C(=O)C(C)(C)c2ccc(-c3cnc(-c4ccncc4)[nH]3)cc21] | | | | 30 | 58.9 | 0.00738 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 7 | 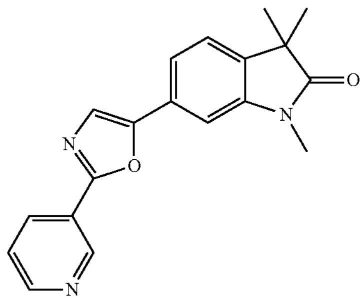 [SMILES: CN1C(=O)C(C)(C)c2ccc(-c3cnc(-c4cccnc4)o3)cc21] | | | | 30 | 83.9 | 0.000932 |
| 8 | 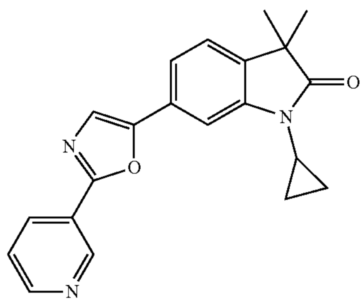 [SMILES: CC1(C)C(=O)N(C2CC2)c2cc(-c3cnc(-c4cccnc4)o3)ccc21] | | | | 30 | 80.5 | 0.00521 |
| 10 | 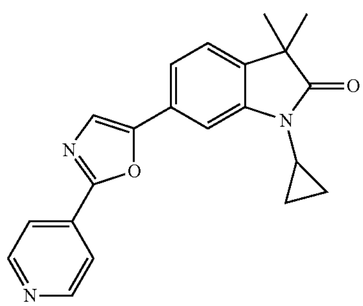 [SMILES: CC1(C)C(=O)N(C2CC2)c2cc(-c3cnc(-c4ccncc4)o3)ccc21] | | | | 30 | 78.8 | 0.00054 |
| 11 | 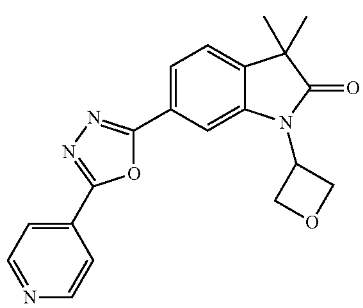 [SMILES: CC1(C)C(=O)N(C2COC2)c2cc(-c3nnc(-c4ccncc4)o3)ccc21] | | | | 30 | 80.9 | 0.003497 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 12 | 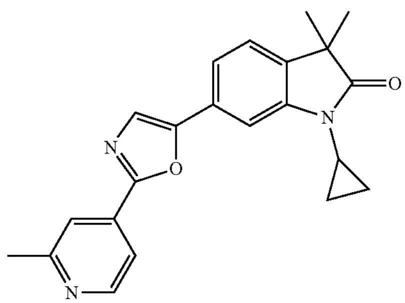 [SMILES: Cc1cc(-c2ncc(-c3ccc4c(c3)N(C3CC3)C(=O)C4(C)C)o2)ccn1] | | | | 30 | 49.1 | 0.01896 |
| 19 | 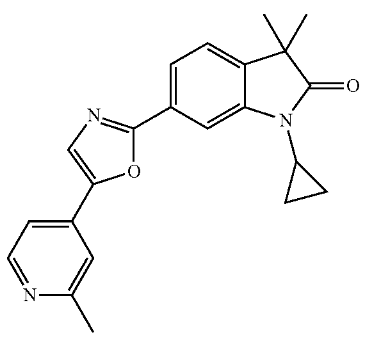 [SMILES: Cc1cc(-c2cnc(-c3ccc4c(c3)N(C3CC3)C(=O)C4(C)C)o2)ccn1] | | | | 30 | 55.9 | 0.03248 |
| 20 | 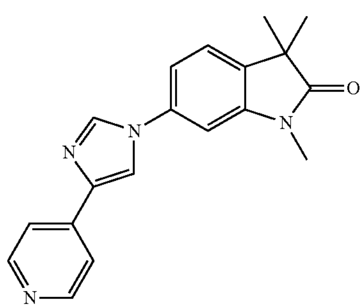 | | | | 30 | 64.4 | 0.01406 |
| 22 | 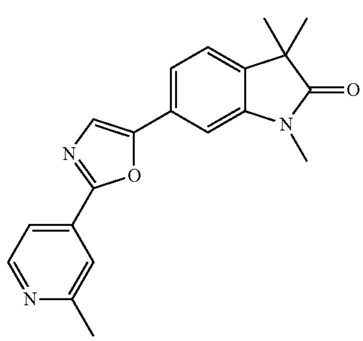 | | | | 30 | 55.9 | 0.03247 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 29 | 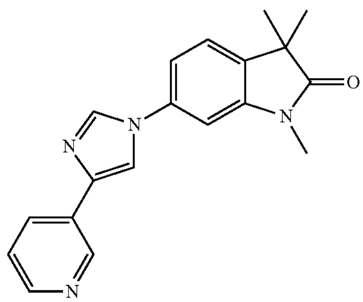 [SMILES: CN1C(=O)C(C)(C)c2ccc(-n3cnc(-c4cccnc4)c3)cc21] | | | | 30 | 80.3 | 0.000932 |
| 33 | 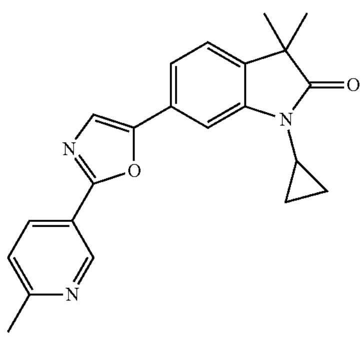 [SMILES: Cc1ccc(-c2ncc(-c3ccc4c(c3)N(C3CC3)C(=O)C4(C)C)o2)cn1] | 1-3-10 po | 3.36 | 0.01405 | | | |
| 35 | 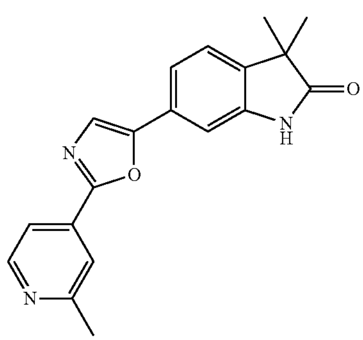 [SMILES: Cc1cc(-c2ncc(-c3ccc4c(c3)NC(=O)C4(C)C)o2)ccn1] | 1-3-10 po | 5.82 | 0.0189 | | | |
| 41 | 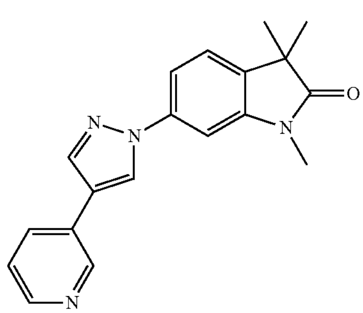 | | | | 30 | 50.3 | 0.05244 |

TABLE 1-continued
Effects of compounds of formula I on L-687,414-induced hyperlocomotion
| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 42 | 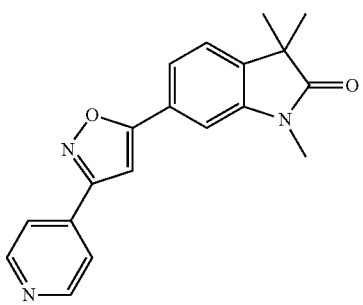 [SMILES: CN1C(=O)C(C)(C)c2ccc(-c3cc(-c4ccncc4)no3)cc21] | | | | 30 | 58.4 | 0.00738 |
| 43 | 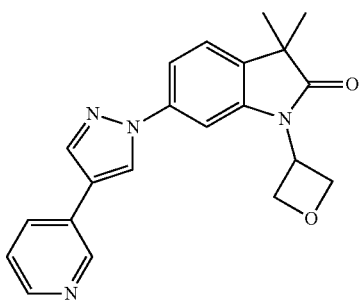 | | | | 30 | 47.3 | 0.03248 |
| 44 | 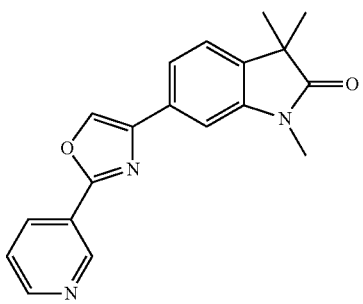 [SMILES: CN1C(=O)C(C)(C)c2ccc(-c3coc(-c4cccnc4)n3)cc21] | | | | 30 | 52.1 | 0.03248 |
| 49 | 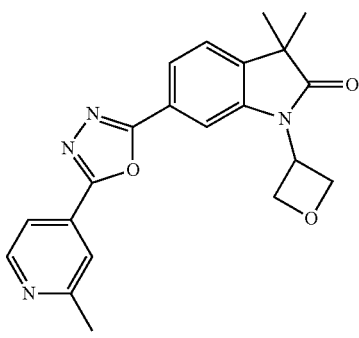 [SMILES: Cc1cc(-c2nnc(-c3ccc4c(c3)N(C3COC3)C(=O)C4(C)C)o2)ccn1] | 1-3-10 po | 5.02 | 0.00349 (10 mg dose) | | | |

TABLE 1-continued

Effects of compounds of formula I on L-687,414-induced hyperlocomotion

| Expl. | structure | Doses po [mg/kg] | $ID_{50}$ po [mg/kg] | Lowest P value | Dose ip [mg/kg] | Inhibition, ip [%] | P value |
|---|---|---|---|---|---|---|---|
| 50 | 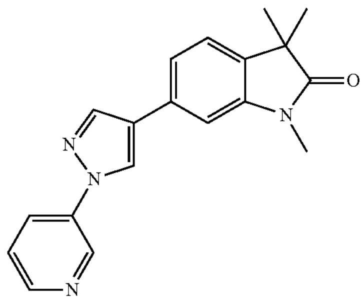 [SMILES: CN1C(=O)C(C)(C)c2ccc(-c3cnn(-c4cccnc4)c3)cc21] | | | | 30 | 44 | 0.04693 |
| 51 | 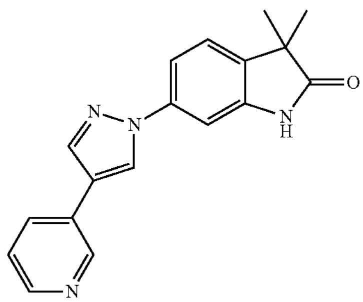 [SMILES: CC1(C)C(=O)Nc2cc(-n3cc(-c4cccnc4)cn3)ccc21] | | | | 30 | 61 | 0.0035 |
| 52 | 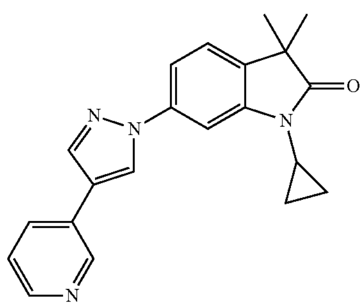 [SMILES: CC1(C)C(=O)N(C2CC2)c2cc(-n3cc(-c4cccnc4)cn3)ccc21] | | | | 30 | 82.1 | 0.00008 |
| 54 | 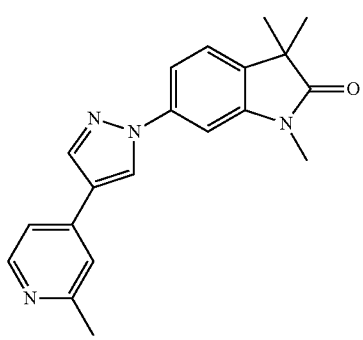 [SMILES: Cc1cc(-c2cnn(-c3ccc4c(c3)N(C)C(=O)C4(C)C)c2)ccn1] | | | | 30 | 41.6 | 0.05245 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 55 | 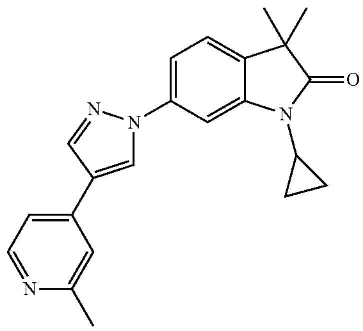 [SMILES: Cc1cc(-c2cnn(-c3ccc4c(c3)N(C3CC3)C(=O)C4(C)C)c2)ccn1] | | | | 30 | 42.7 | 0.03248 |
| 57 | 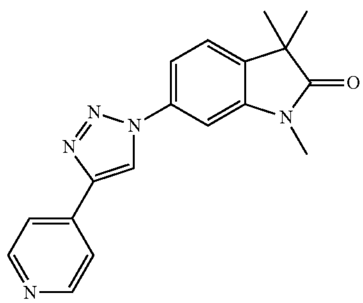 | | | | 30 | 89.2 | 0.00008 |
| 62 | 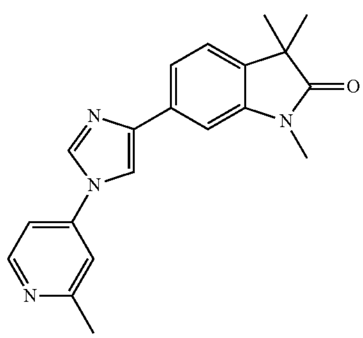 [SMILES: Cc1cc(-n2cnc(-c3ccc4c(c3)N(C)C(=O)C4(C)C)c2)ccn1] | 1-3-10 po | 8.8 | 0.01409 | | | |
| 63 | 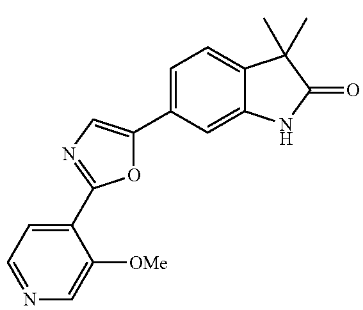 [SMILES: COc1cnccc1-c1ncc(-c2ccc3c(c2)NC(=O)C3(C)C)o1] | | | | 30 | 75 | 0.001476 |

TABLE 1-continued
Effects of compounds of formula I on L-687,414-induced hyperlocomotion
| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 69 | 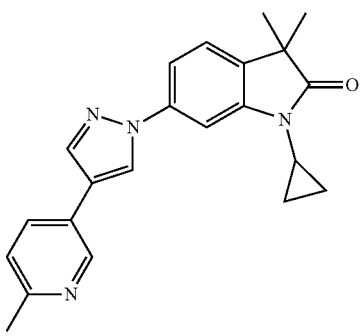 [SMILES: Cc1ccc(-c2cnn(-c3ccc4c(c3)N(C3CC3)C(=O)C4(C)C)c2)cn1] | | | | 30 | 53.3 | 0.02424 |
| 73 | 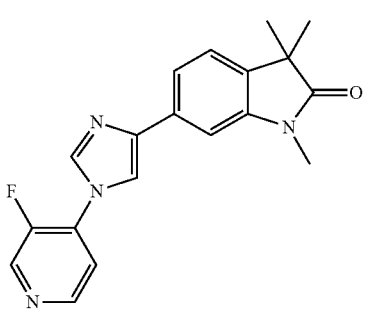 | 1-3-10 po | 2.97 | 0.0052 | | | |
| 74 | 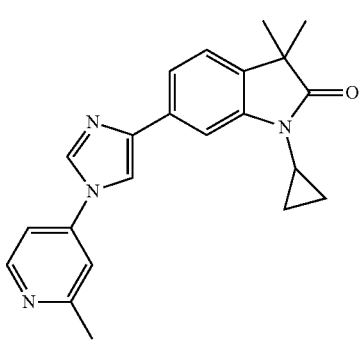 | | | | 30 | 71.4 | 0.0035 |
| 76 | 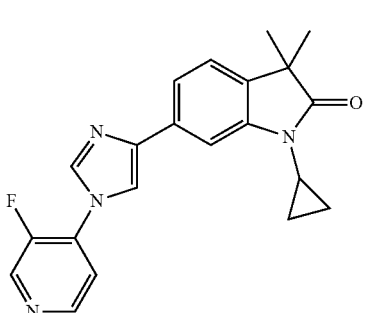 | 1-3-10 po | <1 | 0.01033 | | | |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 77 | 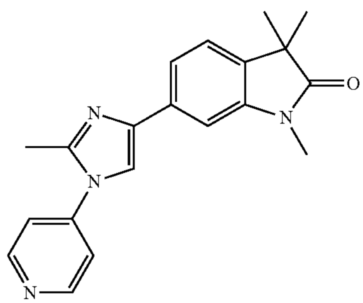 [SMILES: Cc1nc(-c2ccc3c(c2)N(C)C(=O)C3(C)C)cn1-c1ccncc1] | | | | 30 | 89.4 | 0.00008 |
| 80 | 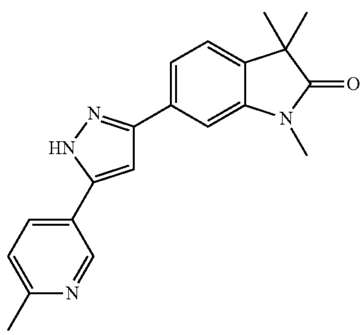 [SMILES: Cc1ccc(-c2cc(-c3ccc4c(c3)N(C)C(=O)C4(C)C)n[nH]2)cn1] | | | | 30 | 62.6 | 0.00738 |
| 88 | 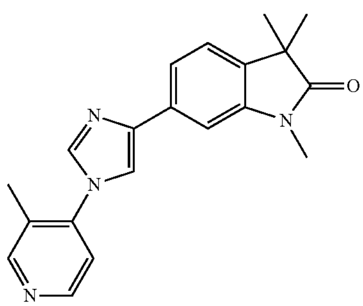 [SMILES: Cc1cnccc1-n1cnc(-c2ccc3c(c2)N(C)C(=O)C3(C)C)c1] | | | | 30 | 93.1 | 0.00008 |
| 89 | 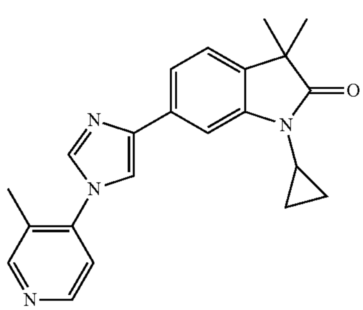 [SMILES: Cc1cnccc1-n1cnc(-c2ccc3c(c2)N(C2CC2)C(=O)C3(C)C)c1] | | | | 30 | 58.5 | 0.01896 |
| 101 | 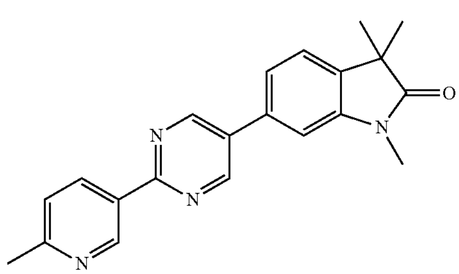 [SMILES: Cc1ccc(-c2ncc(-c3ccc4c(c3)N(C)C(=O)C4(C)C)cn2)cn1] | | | | 30 | 78.4 | 0.00194 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 102 | 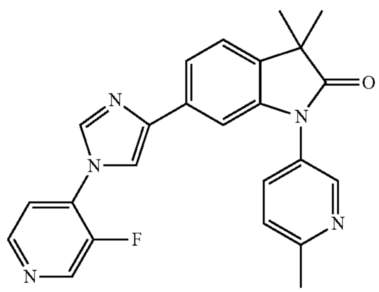 [SMILES: Cc1ccc(N2C(=O)C(C)(C)c3ccc(-c4cn(-c5ccncc5F)cn4)cc32)cn1] | | | | 30 | 65.6 | 0.0037 |
| 104 | 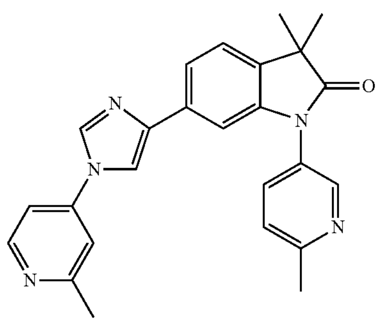 [SMILES: Cc1ccc(N2C(=O)C(C)(C)c3ccc(-c4cn(-c5ccnc(C)c5)cn4)cc32)cn1] | | | | 30 | 64.8 | 0.00194 |
| 105 | 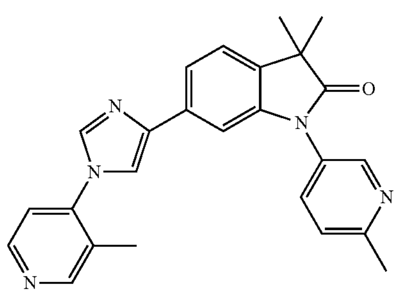 [SMILES: Cc1ccc(N2C(=O)C(C)(C)c3ccc(-c4cn(-c5ccncc5C)cn4)cc32)cn1] | | | | 30 | 40.6 | 0.02028 |
| 106 | 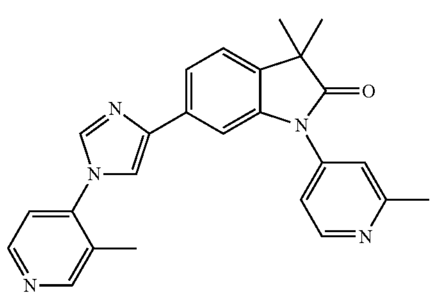 [SMILES: Cc1cc(N2C(=O)C(C)(C)c3ccc(-c4cn(-c5ccncc5C)cn4)cc32)ccn1] | | | | 30 | 68.4 | 0.0037 |
| 110 | 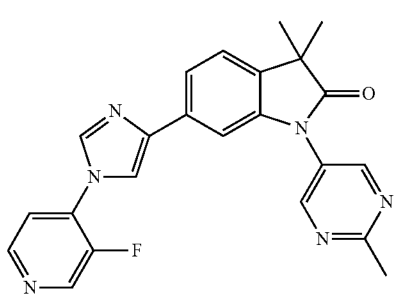 | | | | 30 | 85.4 | 0.00097 |

TABLE 1-continued

Effects of compounds of formula I on L-687,414-induced hyperlocomotion

| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 111 | 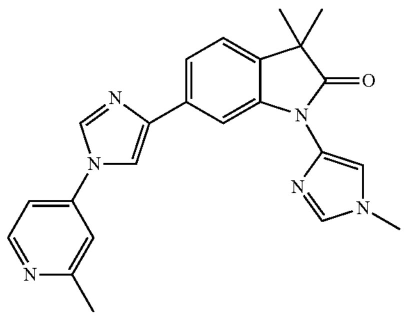 [SMILES: Cc1cc(-n2cnc(-c3ccc4c(c3)N(c3cn(C)cn3)C(=O)C4(C)C)c2)ccn1] | | | | 30 | 55.1 | 0.00906 |
| 112 | 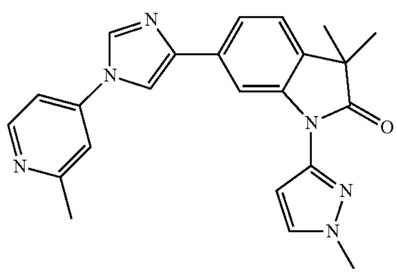 [SMILES: Cc1cc(-n2cnc(-c3ccc4c(c3)N(c3ccn(C)n3)C(=O)C4(C)C)c2)ccn1] | | | | 30 | 52.5 | 0.01197 |
| 113 | 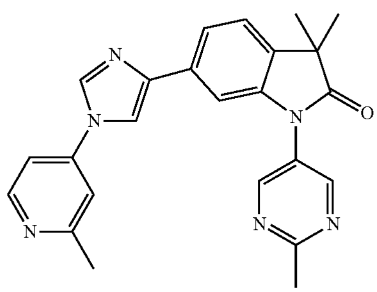 [SMILES: Cc1cc(-n2cnc(-c3ccc4c(c3)N(c3cnc(C)nc3)C(=O)C4(C)C)c2)ccn1] | | | | 30 | 69.9 | 0.00138 |
| 114 | 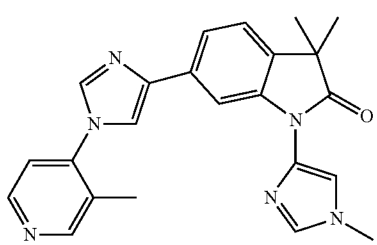 [SMILES: Cc1cnccc1-n1cnc(-c2ccc3c(c2)N(c2cn(C)cn2)C(=O)C3(C)C)c1] | | | | 30 | 64.9 | 0.00679 |
| 115 | 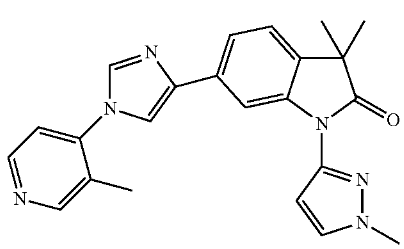 [SMILES: Cc1cnccc1-n1cnc(-c2ccc3c(c2)N(c2ccn(C)n2)C(=O)C3(C)C)c1] | | | | 30 | 74.1 | 0.00194 |

TABLE 1-continued
Effects of compounds of formula I on L-687,414-induced hyperlocomotion
| Expl. | structure | Doses po [mg/kg] | ID$_{50}$ po [mg/kg] | Lowest P value | Dose ip [mg/kg] | Inhibition, ip [%] | P value |
|---|---|---|---|---|---|---|---|
| 116 | 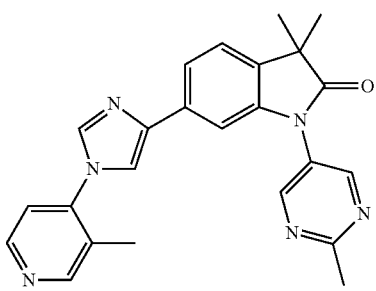 [SMILES: Cc1ncc(N2C(=O)C(C)(C)c3ccc(-c4cn(-c5ccncc5C)cn4)cc32)cn1] | | | | 30 | 74.3 | 0.00194 |
| 118 | 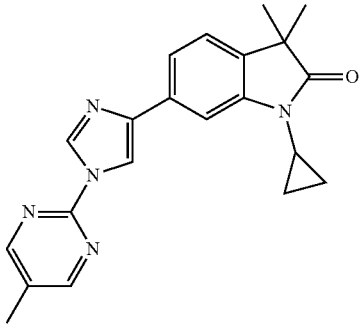 [SMILES: Cc1cnc(-n2cnc(-c3ccc4c(c3)N(C3CC3)C(=O)C4(C)C)c2)nc1] | | | | 30 | 50.3 | 0.03304 |
| 119 | 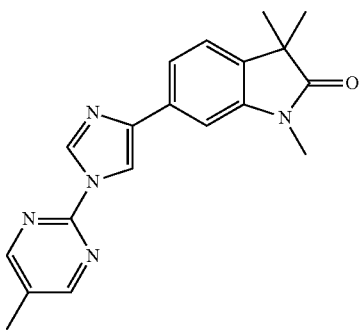 [SMILES: Cc1cnc(-n2cnc(-c3ccc4c(c3)N(C)C(=O)C4(C)C)c2)nc1] | | | | 30 | 48.1 | 0.02602 |
| 123 | 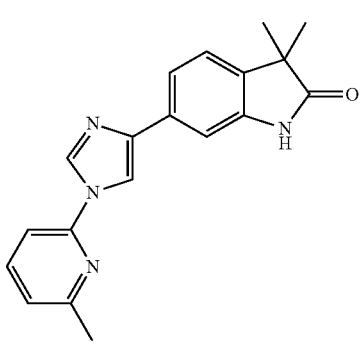 [SMILES: Cc1cccc(-n2cnc(-c3ccc4c(c3)NC(=O)C4(C)C)c2)n1] | | | | 30 | 30.6 | 0.18602 |

TABLE 1-continued

Effects of compounds of formula I on L-687,414-induced hyperlocomotion

| Expl. | structure | Doses po [mg/kg] | $ID_{50}$ po [mg/kg] | Lowest P value | Dose ip [mg/kg] | Inhibition, ip [%] | P value |
|---|---|---|---|---|---|---|---|
| 130 | 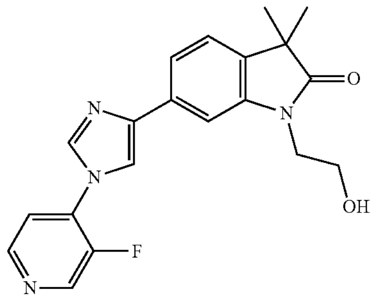 [SMILES: CC1(C)C(=O)N(CCO)c2cc(-c3cn(-c4ccncc4F)cn3)ccc21] | | | | 30 | 74.5 | 0.00679 |
| 132 | 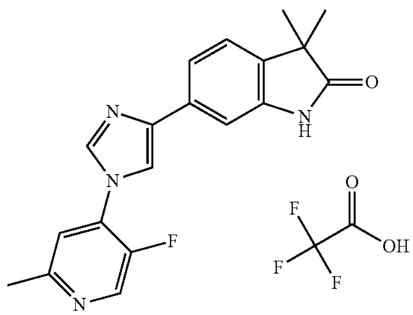 [SMILES: Cc1cc(-n2cnc(-c3ccc4c(c3)NC(=O)C4(C)C)c2)c(F)cn1 ; O=C(O)C(F)(F)F] | | | | 30 | 71.1 | 0.00906 |

As mentioned above, some compounds have been tested in SmartCube®, an analytical system developed by PsychoGenics Inc.

SmartCube® was used to compare the behavioral signature of a test compound to a database of behavioral signatures obtained from a large set of clinically approved reference drugs, grouped per indications. In this way, the neuropharmacological effects of a test compound can be predicted by similarity to major classes of compounds, such as antipsychotics, anxiolytics and antidepressants. This approach is ideally suited to screen collections of existing drugs or drug candidates with previously unknown neuropharmacology, which could expedite the development of new and unexpected treatments for psychiatric disorders.

Some compounds of the present invention were injected i.p. at different doses 15 minutes before the test. At least 8 mice were used in each treatment group. Digital videos of the subjects were processed with computer vision algorithms to extract over 2000 dependent measures including frequency and duration of many different behavioral states. The results of the classifications are presented as bar charts for each compound and dose (mg/kg), the Y-axis indicates the relative probability that the test compound will show efficacy in the specific CNS indication.

Figure 2:
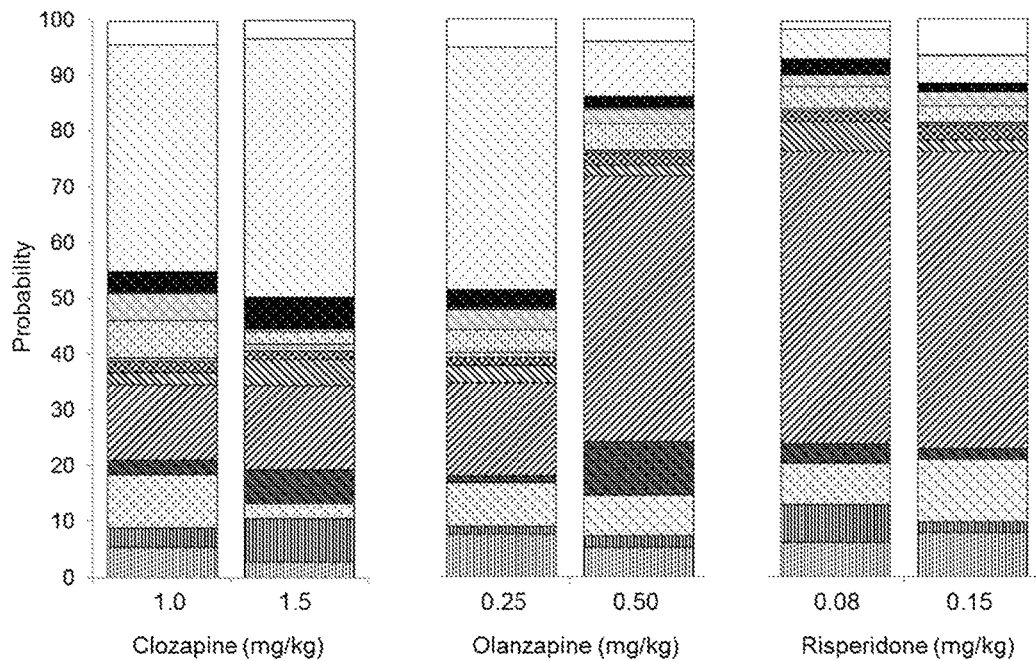
FIG. 2 depicts the SmartCube® signatures of atypical antipsychotics olanzapine and risperidone (each at two doses).

The bar charts of example compounds 35, 47, 62 and 93 at a dose of 25 mg/kg are shown in FIG. 1. For comparison, the behavioral signatures of the atypical antipsychotics olanzapine and risperidone are shown in FIG. 2. Compounds of the present invention show similar signatures to those of atypical antipsychotics. An independent analysis was performed on the unclassified data to determine the similarity of the example compounds to active doses of known atypical antipsychotics. For this analysis, we use discrimination rate as the measure of separability between the two drugs, i.e. one drug's "distinguishability" from another. A rate equal to 50% (or 0.5) corresponds to zero distinguishability. Empirical data has shown that a threshold rate for reliable separation lies above 70% i.e., two drugs showing a discrimination rate of 70% or lower are considered similar, whereas a discrimination rate higher than 70% indicates that two drugs are dissimilar. The table below shows the similarity analysis of selected compounds of the present invention to several atypical antipsychotics. In most cases, the example compounds show a similarity to risperidone, clozapine and olanzapine with a discrimination rate of 0.70.

TABLE 2

Similarity analysis of compounds of formula I (at 25 mg/kg) showing effects in SmartCube ®

| | Clozapine | Olanzapine | Risperidone |
|---|---|---|---|
| Example 35 | 0.69 | 0.75 | 0.60 |
| Example 47 | 0.70 | 0.68 | 0.64 |
| Example 62 | 0.59 | 0.62 | 0.58 |
| Example 93 | 0.63 | 0.68 | 0.60 |

Therefore, it can be assumed that the present compounds have similar efficacies as known atypical antipsychotics.

FIG. 1: SmartCube® signatures of compounds 35, 47, 62 and 93 (at 25 mg/kg)—are similar to those of atypical antipsychotics.

FIG. 2: SmartCube® signatures of atypical antipsychotics Clozapine, Olanzapine and Risperidone (each at two doses).

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers. The active compounds may also be used in form of their prodrugs.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult person weighing 70 kg accordingly lies between 0.7-1400 mg per day, preferably between 7 and 700 mg per day.

Preparation of Pharmaceutical Compositions Comprising Compounds of the Invention:

Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

We claim:

1. A compound of formula (I)

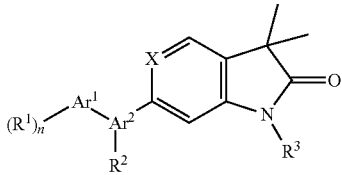

(I)

wherein

Ar¹ is phenyl, pyridinyl or pyrimidinyl;

Ar² is selected from the group consisting of (i), (ii), (iv), (v), (vi), (vii), (viii), (ix), (x) and (xi);

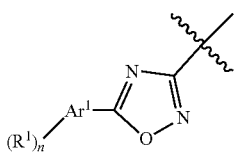

(i)

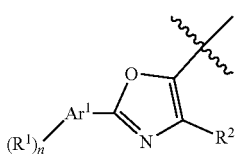

(ii)

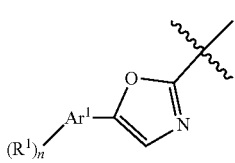

(iii)

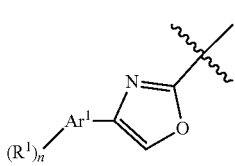

(iv)

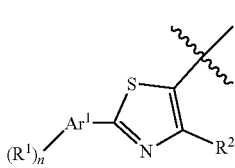

(v)

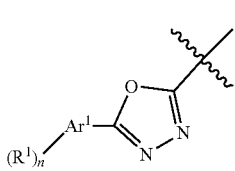

(vi)

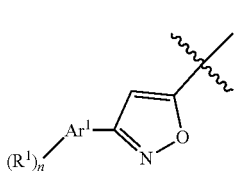

(vii)

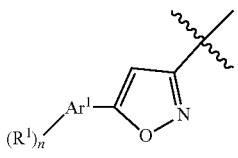

(viii)

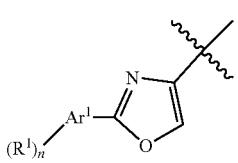

(ix)

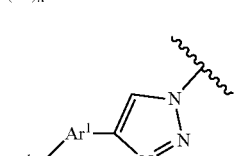

(x)

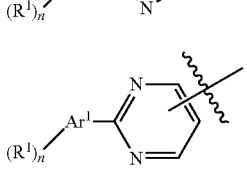

(xi)

;

$R^1$ is hydrogen, $C_{1-7}$-alkyl, halogen or $C_{1-7}$-alkoxy;

$R^3$ is hydrogen, $C_{1-7}$-alkyl, $C_{1-7}$-alkyl substituted by hydroxy, cycloalkyl, oxetan-3-yl, pyridinyl, imidazolyl, pyrazolyl, pyrimidinyl, which rings may optionally substituted by $C_{1-7}$-alkyl, or is $(CH_2)_3$—$S(O)_2$-cyclopropyl;

X is CH or N;

n is 1 or 2; or, or, a pharmaceutically acceptable salt thereof, a racemic mixture, an enantiomer, an optical isomer, a stereoisomer thereof.

2. The compound of claim 1 wherein said compound is of formula Id

Id (Structure Id shown)

3. The compound of claim 1 wherein said compound is of formula Ie

Ie (Structure Ie shown)

4. The compound of claim 1 wherein said compound is of formula If

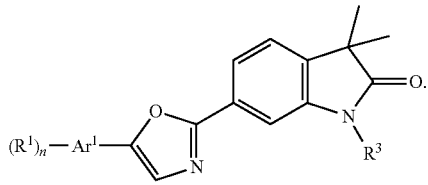

If

5. The compound of claim 1 wherein said compound is of formula Ig

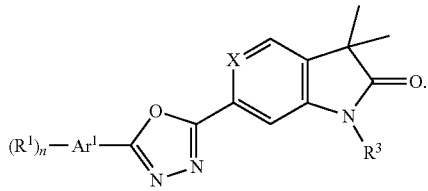

Ig

6. The compound of claim 1 wherein said compound is of formula Ih

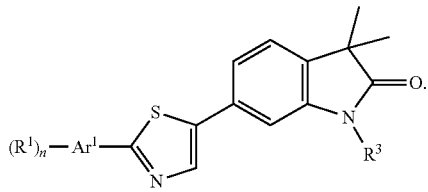

Ih

7. The compound of claim 1 wherein said compound is of formula Ii

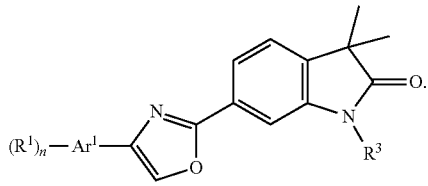

Ii

8. The compound of claim 1 wherein said compound is of formula Im or Im'

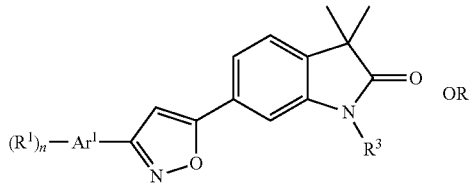

Im
OR

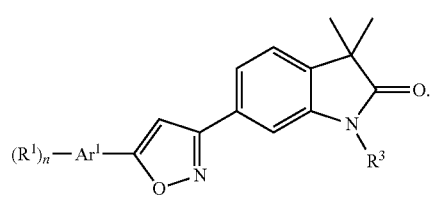

Im'

9. The compound of claim 1 wherein said compound is of formula In

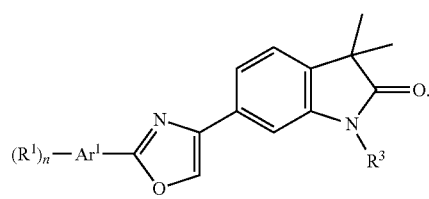

In

10. The compound of claim 1 wherein said compound is of formula Iq

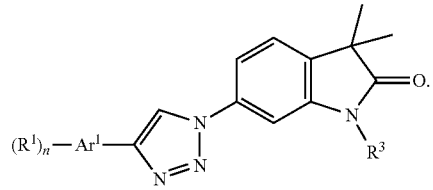

Iq

11. The compound of claim 1 wherein said compound is of formula Is

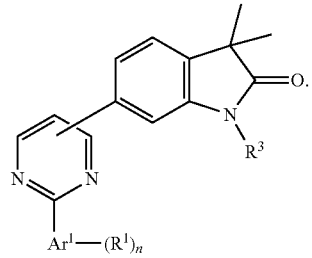

Is

12. The compound of claim 1 which compounds are selected from the group consisting of:
1-Cyclopropyl-3,3-dimethyl-6-(3-(pyridin-4-yl)-1,2,4-oxadiazol-5-yl)indolin-2-one;
1-Cyclopropyl-3,3-dimethyl-6-(5-(pyridin-4-yl)-1,2,4-oxadiazol-3-yl)indolin-2-one;
3,3-Dimethyl-1-oxetan-3-yl-6-(3-pyridin-4-yl-[1,2,4]oxadiazol-5-yl)-1,3-dihydro-indol-2-one;
1,3,3-Trimethyl-6-(2-(pyridin-3-yl)oxazol-5-yl)indolin-2-one;
1-Cyclopropyl-3,3-dimethyl-6-(2-(pyridin-3-yl)oxazol-5-yl)indolin-2-one;
1-Cyclopropyl-3,3-dimethyl-6-(5-(pyridin-3-yl)oxazol-2-yl)indolin-2-one 1-Cyclopropyl-3,3-dimethyl-6-(2-(pyridin-4-yl)oxazol-5-yl)indolin-2-one
3,3-Dimethyl-1-(oxetan-3-yl)-6-(5-(pyridin-4-yl)-1,3,4-oxadiazol-2-yl)indolin-2-one;
1-Cyclopropyl-3,3-dimethyl-6-(2-(2-methylpyridin-4-yl)oxazol-5-yl)indolin-2-one;
1,3,3-Trimethyl-6-(5-(pyridin-4-yl)-1,3,4-oxadiazol-2-yl)indolin-2-one;
1-Cyclopropyl-3,3-dimethyl-6-(2-(2-methylpyridin-4-yl)thiazol-5-yl)indolin-2-one;
1-Cyclopropyl-3,3-dimethyl-6-(4-(pyridin-3-yl)oxazol-2-yl)indolin-2-one;
1-Cyclopropyl-3,3-dimethyl-6-(4-(pyridin-4-yl)oxazol-2-yl)indolin-2-one;
1-Cyclopropyl-3,3-dimethyl-6-(4-(2-methylpyridin-4-yl)oxazol-2-yl)indolin-2-one;
1,3,3-Trimethyl-6-(2-(2-methylpyridin-4-yl)thiazol-5-yl)indolin-2-one;
1-Cyclopropyl-3,3-dimethyl-6-(5-(2-methylpyridin-4-yl)oxazol-2-yl)indolin-2-one;
1,3,3-Trimethyl-6-(4-(pyridin-3-yl)oxazol-2-yl)indolin-2-one;
1,3,3-Trimethyl-6-(2-(2-methylpyridin-4-yl)oxazol-5-yl)indolin-2-one;
3,3-Dimethyl-1-(oxetan-3-yl)-6-(2-(pyridin-3-yl)oxazol-5-yl)indolin-2-one;
3,3-Dimethyl-6-(2-(6-methylpyridin-3-yl)oxazol-5-yl)-1-(oxetan-3-yl)indolin-2-one;
3,3-Dimethyl-6-(2-(pyridin-3-yl)oxazol-5-yl)indolin-2-one;
3,3-Dimethyl-6-(2-(2-methylpyridin-4-yl)oxazol-5-yl)-1-(oxetan-3-yl)indolin-2-one;
3,3-Dimethyl-6-(2-(6-methylpyridin-3-yl)oxazol-5-yl)indolin-2-one;
1-(2-Hydroxyethyl)-3,3-dimethyl-6-(5-(pyridin-4-yl)-1,3,4-oxadiazol-2-yl)indolin-2-one;
1,3,3-Trimethyl-6-(4-methyl-2-(pyridin-3-yl)oxazol-5-yl)indolin-2-one;
1-Cyclopropyl-3,3-dimethyl-6-(2-(6-methylpyridin-3-yl)oxazol-5-yl)indolin-2-one;
3,3-Dimethyl-6-(2-(2-methylpyridin-4-yl)oxazol-5-yl)indolin-2-one;
1,3,3-Trimethyl-6-(4-methyl-2-(6-methylpyridin-3-yl)oxazol-5-yl)indolin-2-one;
1-Cyclopropyl-3,3-dimethyl-6-(4-methyl-2-(6-methylpyridin-3-yl)oxazol-5-yl)indolin-2-one;
1,3,3-Trimethyl-6-(4-methyl-2-(2-methylpyridin-4-yl)oxazol-5-yl)indolin-2-one;
1-Cyclopropyl-3,3-dimethyl-6-(4-methyl-2-(2-methylpyridin-4-yl)oxazol-5-yl)indolin-2-one;
1,3,3-Trimethyl-6-(3-pyridin-4-yl-isoxazol-5-yl)-1,3-dihydro-indol-2-one;
1,3,3-Trimethyl-6-(2-(pyridin-3-yl)oxazol-4-yl)indolin-2-one;
3,3-Dimethyl-6-(5-(2-methylpyridin-4-yl)-1,3,4-oxadiazol-2-yl)-1-(oxetan-3-yl)indolin-2-one;
1,3,3-Trimethyl-6-(4-(pyridin-4-yl)-1H-1,2,3-triazol-1-yl)indolin-2-one;
6-(2-(3-Methoxypyridin-4-yl)oxazol-5-yl)-3,3-dimethylindolin-2-one;
1,3,3-Trimethyl-6-(3-(2-methylpyridin-4-yl)isoxazol-5-yl)indolin-2-one;
1-Cyclopropyl-3,3-dimethyl-6-(3-(2-methylpyridin-4-yl)isoxazol-5-yl)indolin-2-one;
1,3,3-Trimethyl-6-(2-(2-methylpyridin-4-yl)pyrimidin-4-yl)indolin-2-one;
1,3,3-Trimethyl-6-(2-(6-methylpyridin-3-yl)pyrimidin-4-yl)indolin-2-one;
3,3-Dimethyl-6-(2-(6-methylpyridin-3-yl)pyrimidin-4-yl)-1-(oxetan-3-yl)indolin-2-one;
1-Cyclopropyl-3,3-dimethyl-6-[2-(2-methyl-pyridin-4-yl)-oxazol-5-yl]-1,3-dihydro-pyrrolo[3,2-c]pyridin-2-one;
6-(2-(5-Fluoro-2-methylpyridin-4-yl)oxazol-5-yl)-1,3,3-trimethylindolin-2-one;
3,3-Dimethyl-6-[5-(2-methyl-pyridin-4-yl)-[1,3,4]oxadiazol-2-yl]-1-oxetan-3-yl-1,3-dihydro-pyrrolo[3,2-c]pyridin-2-one;
6-(2-(2-Fluoro-5-methylpyridin-4-yl)oxazol-5-yl)-1,3,3-trimethylindolin-2-one;
6-(5-(5-Fluoro-2-methylpyridin-4-yl)-1,3,4-oxadiazol-2-yl)-1,3,3-trimethylindolin-2-one;
1,3,3-Trimethyl-6-(2-(6-methylpyridin-3-yl)pyrimidin-5-yl)indolin-2-one; and,
1,3,3-Trimethyl-6-[5-(3-methyl-4-pyridyl)isoxazol-3-yl]indolin-2-one; or,
a pharmaceutically acceptable salt thereof.

13. A pharmaceutical composition comprising a compound in accordance with claim 1 and at least one pharmaceutically acceptable carrier, diluent or excipient for the treatment of certain central nervous system disorders which are positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, autism, Parkinson's disease, chronic pain, borderline personality disorder, sleep disturbances, chronic fatigue syndrome, stiffness, antiinflammatory effects in arthritis and balance problems.

* * * * *